(12) United States Patent
Abdou

(10) Patent No.: US 9,901,458 B1
(45) Date of Patent: Feb. 27, 2018

(54) SPINAL FIXATION DEVICES AND METHODS OF USE

(71) Applicant: Samy Abdou, San Diego, CA (US)

(72) Inventor: Samy Abdou, San Diego, CA (US)

( * ) Notice: Subject to any disclaimer, the term of this patent is extended or adjusted under 35 U.S.C. 154(b) by 0 days.

(21) Appl. No.: 15/599,315

(22) Filed: May 18, 2017

Related U.S. Application Data

(60) Division of application No. 15/478,088, filed on Apr. 3, 2017, which is a division of application No. (Continued)

(51) Int. Cl.
*A61F 2/44* (2006.01)
*A61F 2/46* (2006.01)
(Continued)

(52) U.S. Cl.
CPC ............ *A61F 2/442* (2013.01); *A61F 2/4455* (2013.01); *A61F 2/4601* (2013.01); *A61F 2/4611* (2013.01); *A61F 2002/2835* (2013.01); *A61F 2002/30062* (2013.01); *A61F 2002/3093* (2013.01); *A61F 2002/30153* (2013.01); *A61F 2002/30433* (2013.01); *A61F 2002/30578* (2013.01); *A61F 2002/30774* (2013.01); *A61F 2002/448* (2013.01); *A61F 2002/4475* (2013.01); *A61F 2002/4623* (2013.01); *A61F 2002/4627* (2013.01); *A61F 2002/4629* (2013.01); *A61F 2310/00017* (2013.01); (Continued)

(58) Field of Classification Search
CPC ... A61F 2/46; A61F 2/4611; A61F 2002/4415
See application file for complete search history.

(56) References Cited

U.S. PATENT DOCUMENTS

| 824,983 A | 7/1906 | Charles |
|---|---|---|
| 2,248,054 A | 7/1941 | Becker |
| (Continued) | | |

FOREIGN PATENT DOCUMENTS

| EP | 1180348 A2 | 2/2002 |
|---|---|---|
| FR | 2781359 A1 | 1/2000 |
| (Continued) | | |

OTHER PUBLICATIONS

Abstract for French Patent Publication FR2781359, Published Jan. 28, 2000, entitled: "Osteosynthesis Frame for Spinal Surgery has Rod with Clamps to Hold Cross Bars with Anchor Screws". Accession No. 9867555 (Derwent Information Ltd.).
(Continued)

*Primary Examiner* — David Bates
(74) *Attorney, Agent, or Firm* — Gazdzinski & Associates, PC

(57) ABSTRACT

Placement apparatus and methods of use for implantation of spacers within an inter-vertebral disc space. In one embodiment, the load-bearing superstructure of the implant is subdivided and the bone forming material is positioned within an internal space of the placement instrument but external to the load bearing elements themselves. At least a portion of the bone graft material is freely contained within the disc space. A method of using the device is also described. In one embodiment, the placement device is used to place the implantable spacers at opposing ends of the disc space using a directly lateral surgical approach.

30 Claims, 44 Drawing Sheets

Related U.S. Application Data

15/132,095, filed on Apr. 18, 2016, now Pat. No. 9,610,176, which is a division of application No. 14/500,815, filed on Sep. 29, 2014, now Pat. No. 9,314,350, which is a continuation of application No. 13/624,792, filed on Sep. 21, 2012, now Pat. No. 8,845,728.

(60) Provisional application No. 61/626,340, filed on Sep. 23, 2011.

(51) Int. Cl.
    *A61F 2/28* (2006.01)
    *A61F 2/30* (2006.01)

(52) U.S. Cl.
    CPC ............ *A61F 2310/00023* (2013.01); *A61F 2310/00029* (2013.01); *A61F 2310/00131* (2013.01); *A61F 2310/00179* (2013.01)

(56) References Cited

U.S. PATENT DOCUMENTS

| | | |
|---|---|---|
| 2,329,398 A | 9/1943 | Duffy |
| 2,370,407 A | 2/1945 | McCartney |
| 2,574,352 A | 11/1951 | Senter |
| 3,236,141 A | 2/1966 | Smith |
| 3,604,487 A | 9/1971 | Richard |
| 3,659,595 A | 5/1972 | Edward |
| 3,867,728 A | 2/1975 | Stubstad et al. |
| 4,254,763 A | 3/1981 | McCready et al. |
| 4,399,813 A | 8/1983 | Barber |
| 4,636,217 A | 1/1987 | Ogilvie et al. |
| 4,820,305 A | 4/1989 | Harms et al. |
| 4,834,757 A | 5/1989 | Brantigan |
| 4,877,020 A | 10/1989 | Vich |
| 4,903,692 A | 2/1990 | Reese |
| 4,907,577 A | 3/1990 | Wu |
| 4,961,740 A | 10/1990 | Ray et al. |
| 5,015,247 A | 5/1991 | Michelson |
| 5,055,104 A | 10/1991 | Ray |
| 5,192,327 A | 3/1993 | Brantigan |
| 5,236,460 A | 8/1993 | Barber |
| 5,252,016 A | 10/1993 | Schmid et al. |
| 5,275,601 A | 1/1994 | Gogolewski et al. |
| 5,352,231 A | 10/1994 | Brumfield et al. |
| 5,354,292 A | 10/1994 | Braeuer et al. |
| 5,360,429 A | 11/1994 | Jeanson et al. |
| 5,361,766 A | 11/1994 | Nichols et al. |
| 5,397,364 A | 3/1995 | Kozak et al. |
| 5,439,339 A | 8/1995 | Batchelor |
| 5,443,514 A | 8/1995 | Steffee |
| 5,458,638 A | 10/1995 | Kuslich et al. |
| 5,484,440 A | 1/1996 | Allard |
| 5,487,742 A | 1/1996 | Cotrel |
| 5,489,308 A | 2/1996 | Kuslich et al. |
| 5,531,747 A | 7/1996 | Ray |
| 5,531,751 A | 7/1996 | Schultheiss et al. |
| 5,534,001 A | 7/1996 | Schlapfer et al. |
| 5,534,027 A | 7/1996 | Hodorek |
| 5,545,164 A | 8/1996 | Howland |
| 5,558,674 A | 9/1996 | Heggeness et al. |
| 5,591,166 A | 1/1997 | Bernhardt et al. |
| 5,599,279 A | 2/1997 | Slotman et al. |
| 5,607,426 A | 3/1997 | Ralph et al. |
| 5,609,635 A | 3/1997 | Michelson |
| 5,609,637 A | 3/1997 | Biedermann et al. |
| 5,616,142 A | 4/1997 | Yuan et al. |
| 5,649,931 A | 7/1997 | Bryant et al. |
| 5,672,176 A | 9/1997 | Biedermann et al. |
| 5,681,311 A | 10/1997 | Foley et al. |
| 5,681,312 A | 10/1997 | Yuan et al. |
| 5,681,313 A | 10/1997 | Diez |
| 5,683,394 A | 11/1997 | Rinner |
| 5,702,451 A | 12/1997 | Biedermann et al. |
| 5,704,936 A | 1/1998 | Mazel |
| 5,707,372 A | 1/1998 | Errico et al. |
| 5,709,686 A | 1/1998 | Talos et al. |
| 5,713,900 A | 2/1998 | Benzel et al. |
| 5,716,357 A | 2/1998 | Rogozinski |
| 5,735,853 A | 4/1998 | Olerud |
| 5,741,261 A | 4/1998 | Moskovitz et al. |
| 5,749,916 A | 5/1998 | Richelsoph |
| 5,776,199 A | 7/1998 | Michelson |
| 5,782,830 A | 7/1998 | Farris |
| 5,782,832 A | 7/1998 | Larsen et al. |
| 5,865,848 A | 2/1999 | Baker |
| 5,876,402 A | 3/1999 | Errico et al. |
| 5,888,222 A | 3/1999 | Coates et al. |
| 5,888,224 A | 3/1999 | Beckers et al. |
| 5,904,683 A | 5/1999 | Pohndorf et al. |
| 5,908,382 A | 6/1999 | Koros et al. |
| 5,954,722 A | 9/1999 | Bono |
| 5,964,763 A | 10/1999 | Incavo et al. |
| 5,971,987 A | 10/1999 | Huxel et al. |
| 5,976,140 A | 11/1999 | Haas |
| 5,980,522 A | 11/1999 | Koros et al. |
| 5,984,967 A | 11/1999 | Zdeblick et al. |
| 5,993,449 A | 11/1999 | Schlaepfer et al. |
| 6,004,326 A | 12/1999 | Castro et al. |
| 6,033,170 A | 3/2000 | Gold |
| 6,039,761 A | 3/2000 | Li et al. |
| 6,045,579 A | 4/2000 | Hochshuler et al. |
| 6,059,786 A | 5/2000 | Jackson |
| 6,071,310 A | 6/2000 | Picha et al. |
| 6,080,193 A | 6/2000 | Hochshuler et al. |
| 6,083,225 A | 7/2000 | Winslow et al. |
| 6,086,613 A | 7/2000 | Camino et al. |
| 6,099,531 A | 8/2000 | Bonutti |
| 6,117,135 A | 9/2000 | Schlaepfer |
| 6,126,689 A | 10/2000 | Brett |
| 6,139,316 A | 10/2000 | Sachdeva et al. |
| 6,139,549 A | 10/2000 | Keller |
| 6,156,037 A | 12/2000 | LeHuec et al. |
| 6,159,244 A | 12/2000 | Suddaby |
| 6,174,311 B1 | 1/2001 | Branch et al. |
| 6,176,882 B1 | 1/2001 | Biedermann et al. |
| 6,187,005 B1 | 2/2001 | Brace et al. |
| 6,193,757 B1 | 2/2001 | Foley et al. |
| 6,197,033 B1 | 3/2001 | Haid, Jr. et al. |
| 6,200,322 B1 | 3/2001 | Branch et al. |
| 6,206,922 B1 | 3/2001 | Zdeblick et al. |
| 6,210,412 B1 | 4/2001 | Michelson |
| 6,224,595 B1 | 5/2001 | Michelson |
| 6,228,022 B1 | 5/2001 | Friesem et al. |
| 6,245,072 B1 | 6/2001 | Zdeblick et al. |
| 6,248,110 B1 | 6/2001 | Reiley et al. |
| 6,251,112 B1 | 6/2001 | Jackson |
| 6,251,140 B1 | 6/2001 | Marino et al. |
| 6,258,125 B1 | 7/2001 | Paul et al. |
| 6,264,656 B1 | 7/2001 | Michelson |
| 6,270,498 B1 | 8/2001 | Michelson |
| 6,277,149 B1 | 8/2001 | Boyle et al. |
| 6,287,308 B1 | 9/2001 | Betz et al. |
| 6,302,843 B1 | 10/2001 | Lees et al. |
| 6,302,914 B1 | 10/2001 | Michelson |
| 6,306,136 B1 | 10/2001 | Baccelli |
| 6,309,391 B1 | 10/2001 | Crandall et al. |
| RE37,479 E | 12/2001 | Kuslich |
| 6,331,179 B1 | 12/2001 | Freid et al. |
| 6,342,074 B1 | 1/2002 | Simpson |
| 6,348,058 B1 | 2/2002 | Melkent et al. |
| 6,361,258 B1 | 3/2002 | Heesch |
| RE37,665 E | 4/2002 | Ralph |
| 6,364,880 B1 | 4/2002 | Michelson |
| 6,371,988 B1 | 4/2002 | Pafford et al. |
| 6,375,655 B1 | 4/2002 | Zdeblick et al. |
| 6,402,752 B2 | 6/2002 | Schäffler-Wachter et al. |
| 6,402,756 B1 | 6/2002 | Ralph et al. |
| 6,419,706 B1 | 7/2002 | Graf |
| 6,440,139 B2 | 8/2002 | Michelson |
| 6,440,170 B1 | 8/2002 | Jackson |
| 6,447,547 B1 | 9/2002 | Michelson |
| 6,447,548 B1 | 9/2002 | Ralph et al. |

(56) References Cited

U.S. PATENT DOCUMENTS

| | | |
|---|---|---|
| 6,471,724 B2 | 10/2002 | Zdeblick et al. |
| 6,527,773 B1 | 3/2003 | Lin et al. |
| 6,537,279 B1 | 3/2003 | Michelson |
| 6,540,785 B1 | 4/2003 | Gill et al. |
| 6,554,863 B2 | 4/2003 | Paul et al. |
| 6,558,387 B2 | 5/2003 | Errico et al. |
| 6,562,074 B2 | 5/2003 | Gerbec et al. |
| 6,569,168 B2 | 5/2003 | Lin |
| 6,575,899 B1 | 6/2003 | Foley et al. |
| 6,575,981 B1 | 6/2003 | Boyd et al. |
| 6,576,016 B1 | 6/2003 | Hochshuler et al. |
| 6,582,431 B1 | 6/2003 | Ray |
| 6,595,995 B2 | 7/2003 | Zdeblick et al. |
| 6,599,290 B2 | 7/2003 | Bailey et al. |
| 6,607,530 B1 | 8/2003 | Carl et al. |
| 6,610,089 B1 | 8/2003 | Liu et al. |
| 6,613,091 B1 | 9/2003 | Zdeblick et al. |
| 6,616,695 B1 | 9/2003 | Crozet et al. |
| 6,638,310 B2 | 10/2003 | Lin et al. |
| 6,641,614 B1 | 11/2003 | Wagner et al. |
| 6,645,206 B1 | 11/2003 | Zdeblick et al. |
| 6,645,207 B2 | 11/2003 | Dixon et al. |
| 6,648,895 B2 | 11/2003 | Burkus et al. |
| 6,648,917 B2 | 11/2003 | Gerbec et al. |
| 6,663,631 B2 | 12/2003 | Kuntz |
| 6,666,866 B2 | 12/2003 | Martz et al. |
| 6,666,867 B2 | 12/2003 | Ralph et al. |
| 6,666,891 B2 | 12/2003 | Boehm et al. |
| 6,679,883 B2 | 1/2004 | Hawkes et al. |
| 6,692,495 B1 | 2/2004 | Zacouto |
| 6,706,067 B2 | 3/2004 | Shimp et al. |
| 6,706,070 B1 | 3/2004 | Wagner et al. |
| 6,706,922 B2 | 3/2004 | Wolff et al. |
| 6,709,389 B2 | 3/2004 | Farascioni |
| 6,712,819 B2 | 3/2004 | Zucherman et al. |
| 6,712,852 B1 | 3/2004 | Chung et al. |
| 6,719,794 B2 | 4/2004 | Gerber et al. |
| 6,723,043 B2 | 4/2004 | Kleeman et al. |
| 6,723,096 B1 | 4/2004 | Dorchak et al. |
| 6,723,100 B2 | 4/2004 | Biedermann et al. |
| 6,723,126 B1 | 4/2004 | Berry |
| 6,730,127 B2 | 5/2004 | Michelson |
| 6,746,454 B2 | 6/2004 | Winterbottom et al. |
| 6,752,832 B2 | 6/2004 | Neumann |
| 6,761,738 B1 | 7/2004 | Boyd |
| 6,767,367 B1 | 7/2004 | Michelson |
| 6,770,074 B2 | 8/2004 | Michelson |
| 6,770,096 B2 | 8/2004 | Bolger et al. |
| 6,780,192 B2 | 8/2004 | McKay et al. |
| 6,827,722 B1 | 12/2004 | Schoenefeld |
| 6,830,570 B1 | 12/2004 | Frey et al. |
| 6,830,571 B2 | 12/2004 | Lenke et al. |
| 6,830,589 B2 | 12/2004 | Erickson |
| 6,849,093 B2 | 2/2005 | Michelson |
| 6,852,127 B2 | 2/2005 | Varga et al. |
| 6,852,129 B2 | 2/2005 | Gerbec et al. |
| 6,855,147 B2 | 2/2005 | Harrington et al. |
| 6,863,673 B2 | 3/2005 | Gerbec et al. |
| 6,881,228 B2 | 4/2005 | Zdeblick et al. |
| 6,890,355 B2 | 5/2005 | Michelson |
| 6,896,680 B2 | 5/2005 | Michelson |
| 6,902,566 B2 | 6/2005 | Zucherman et al. |
| 6,911,045 B2 | 6/2005 | Shimp |
| 6,926,737 B2 | 8/2005 | Jackson |
| 6,949,105 B2 | 9/2005 | Bryan et al. |
| 6,953,477 B2 | 10/2005 | Berry |
| 6,964,687 B1 | 11/2005 | Bernard et al. |
| 6,972,019 B2 | 12/2005 | Michelson |
| 6,979,334 B2 | 12/2005 | Dalton |
| 6,984,245 B2 | 1/2006 | McGahan et al. |
| 6,986,772 B2 | 1/2006 | Michelson |
| 6,991,654 B2 | 1/2006 | Foley |
| 7,018,415 B1 | 3/2006 | McKay |
| 7,018,416 B2 | 3/2006 | Hanson et al. |
| 7,033,362 B2 | 4/2006 | McGahan et al. |
| 7,037,339 B2 | 5/2006 | Houfburg |
| 7,044,971 B2 | 5/2006 | Suddaby |
| 7,070,598 B2 | 7/2006 | Lim et al. |
| 7,083,625 B2 | 8/2006 | Berry |
| 7,097,648 B1 | 8/2006 | Globerman et al. |
| 7,118,579 B2 | 10/2006 | Michelson |
| 7,125,425 B2 | 10/2006 | Simonton et al. |
| 7,156,806 B2 | 1/2007 | Dobrovolny |
| 7,166,121 B2 | 1/2007 | Reiley et al. |
| 7,169,183 B2 | 1/2007 | Liu et al. |
| 7,204,851 B2 | 4/2007 | Trieu et al. |
| 7,211,085 B2 | 5/2007 | Michelson |
| 7,217,291 B2 | 5/2007 | Zucherman et al. |
| 7,227,477 B2 | 6/2007 | Ye |
| 7,235,105 B2 | 6/2007 | Jackson |
| 7,241,297 B2 | 7/2007 | Shaolian et al. |
| 7,252,673 B2 | 8/2007 | Lim |
| 7,276,081 B1 | 10/2007 | Coates et al. |
| 7,276,082 B2 | 10/2007 | Zdeblick et al. |
| 7,282,063 B2 | 10/2007 | Cohen et al. |
| 7,291,149 B1 | 11/2007 | Michelson |
| 7,300,441 B2 | 11/2007 | Haid et al. |
| 7,311,734 B2 | 12/2007 | Van Hoeck et al. |
| 7,318,840 B2 | 1/2008 | McKay |
| 7,326,216 B2 | 2/2008 | Bertagnoli et al. |
| 7,331,961 B2 | 2/2008 | Abdou |
| 7,341,587 B2 | 3/2008 | Molz, IV et al. |
| 7,473,276 B2 | 1/2009 | Aebi et al. |
| 7,476,228 B2 | 1/2009 | Abdou |
| 7,491,205 B1 | 2/2009 | Michelson |
| 7,497,859 B2 | 3/2009 | Zucherman et al. |
| 7,534,265 B1 | 5/2009 | Boyd et al. |
| 7,537,616 B1 | 5/2009 | Branch et al. |
| 7,547,308 B2 | 6/2009 | Bertagnoli et al. |
| 7,547,325 B2 | 6/2009 | Biedermann et al. |
| 7,559,930 B2 | 7/2009 | Allard et al. |
| 7,572,276 B2 | 8/2009 | Lim et al. |
| 7,575,580 B2 | 8/2009 | Lim et al. |
| 7,578,820 B2 | 8/2009 | Moore et al. |
| 7,591,851 B2 | 9/2009 | Winslow et al. |
| 7,594,919 B2 | 9/2009 | Peterman |
| 7,597,694 B2 | 10/2009 | Lim et al. |
| 7,618,423 B1 | 11/2009 | Valentine et al. |
| 7,621,953 B2 | 11/2009 | Braddock, Jr. et al. |
| 7,621,957 B2 | 11/2009 | Errico et al. |
| 7,625,379 B2 | 12/2009 | Puno et al. |
| 7,625,380 B2 | 12/2009 | Drewry et al. |
| 7,635,371 B2 | 12/2009 | McGahan et al. |
| 7,641,690 B2 | 1/2010 | Abdou et al. |
| 7,641,693 B2 | 1/2010 | Gutlin et al. |
| 7,645,281 B2 | 1/2010 | Marik |
| 7,682,396 B2 | 3/2010 | Beaurain et al. |
| 7,708,743 B2 | 5/2010 | Anderson et al. |
| 7,749,231 B2 | 7/2010 | Bonvallet et al. |
| 7,749,269 B2 | 7/2010 | Peterman et al. |
| 7,749,270 B2 | 7/2010 | Peterman |
| 7,753,958 B2 | 7/2010 | Gordon et al. |
| 7,758,648 B2 | 7/2010 | Castleman et al. |
| 7,763,078 B2 | 7/2010 | Peterman et al. |
| 7,766,918 B2 | 8/2010 | Allard et al. |
| 7,771,432 B2 | 8/2010 | Schwab et al. |
| 7,771,473 B2 | 8/2010 | Thramann |
| 7,780,732 B2 | 8/2010 | Abernathie et al. |
| 7,794,501 B2 | 9/2010 | Edie et al. |
| 7,799,081 B2 | 9/2010 | McKinley |
| 7,815,683 B2 | 10/2010 | Melkent et al. |
| 7,828,807 B2 | 11/2010 | LeHuec et al. |
| 7,837,732 B2 | 11/2010 | Zucherman et al. |
| 7,837,734 B2 | 11/2010 | Zucherman et al. |
| 7,857,818 B2 | 12/2010 | Trieu et al. |
| 7,875,034 B2 | 1/2011 | Josse et al. |
| 7,875,078 B2 | 1/2011 | Wysocki et al. |
| 7,883,542 B2 | 2/2011 | Zipnick et al. |
| 7,901,409 B2 | 3/2011 | Canaveral et al. |
| 7,901,458 B2 | 3/2011 | DeRidder et al. |
| 7,959,677 B2 | 6/2011 | Landry et al. |
| 7,988,699 B2 | 8/2011 | Martz et al. |
| 8,002,833 B2 | 8/2011 | Fabris et al. |
| 8,034,109 B2 | 10/2011 | Zwirkoski |

(56) References Cited

U.S. PATENT DOCUMENTS

| | | |
|---|---|---|
| 8,043,376 B2 | 10/2011 | Falahee |
| 8,043,380 B1 | 10/2011 | Park et al. |
| 8,062,299 B2 | 11/2011 | McGahan et al. |
| 8,066,714 B2 | 11/2011 | Shipp et al. |
| 8,083,798 B2 | 12/2011 | Allard et al. |
| 8,163,026 B2 | 4/2012 | Gray |
| 8,251,997 B2 | 8/2012 | Michelson |
| 8,268,004 B2 | 9/2012 | Castleman et al. |
| 8,349,012 B2 | 1/2013 | McKay |
| 8,388,687 B2 | 3/2013 | Gimbel et al. |
| 8,454,621 B2 | 6/2013 | Deridder et al. |
| 8,454,694 B2 | 6/2013 | Armstrong et al. |
| 8,465,547 B2 | 6/2013 | Melkent et al. |
| 8,480,747 B2 | 7/2013 | Melkent et al. |
| 8,486,147 B2 | 7/2013 | De et al. |
| 8,506,629 B2 | 8/2013 | Weiland |
| 8,663,331 B2 | 3/2014 | McClellan, III et al. |
| 8,795,375 B2 | 8/2014 | Malberg |
| 8,845,728 B1 | 9/2014 | Abdou |
| 8,876,904 B2 | 11/2014 | Pimenta et al. |
| 8,911,441 B2 | 12/2014 | Dace et al. |
| 8,956,415 B2 | 2/2015 | Cowan |
| 8,998,905 B2 | 4/2015 | Marik et al. |
| 9,011,538 B2 | 4/2015 | Allard et al. |
| 9,308,099 B2 | 4/2016 | Triplett et al. |
| 9,364,338 B2 | 6/2016 | Malberg |
| 9,408,717 B2 | 8/2016 | Perrow et al. |
| 9,445,918 B1 | 9/2016 | Lin et al. |
| 2001/0001129 A1 | 5/2001 | McKay et al. |
| 2002/0016595 A1 | 2/2002 | Michelson |
| 2002/0045945 A1 | 4/2002 | Liu et al. |
| 2002/0055741 A1 | 5/2002 | Schlapfer et al. |
| 2002/0082700 A1 | 6/2002 | Bianchi et al. |
| 2002/0099386 A1 | 7/2002 | Beger et al. |
| 2002/0111628 A1 | 8/2002 | Ralph et al. |
| 2002/0143328 A1 | 10/2002 | Shluzas et al. |
| 2002/0169453 A1 | 11/2002 | Berger |
| 2002/0183755 A1 | 12/2002 | Michelson |
| 2002/0188296 A1 | 12/2002 | Michelson |
| 2003/0023305 A1 | 1/2003 | McKay |
| 2003/0078583 A1 | 4/2003 | Biedermann et al. |
| 2003/0083747 A1 | 5/2003 | Winterbottom et al. |
| 2003/0093153 A1 | 5/2003 | Banick et al. |
| 2003/0153913 A1 | 8/2003 | Altarac et al. |
| 2004/0049271 A1 | 3/2004 | Biedermann et al. |
| 2004/0054412 A1 | 3/2004 | Gerbec et al. |
| 2004/0059318 A1 | 3/2004 | Zhang et al. |
| 2004/0087947 A1 | 5/2004 | Lim et al. |
| 2004/0093083 A1 | 5/2004 | Branch et al. |
| 2004/0098129 A1 | 5/2004 | Lin |
| 2004/0106927 A1 | 6/2004 | Ruffner et al. |
| 2004/0143264 A1 | 7/2004 | McAfee |
| 2004/0153065 A1 | 8/2004 | Lim |
| 2004/0172134 A1 | 9/2004 | Berry |
| 2004/0186572 A1 | 9/2004 | Lange et al. |
| 2004/0204713 A1 | 10/2004 | Abdou |
| 2004/0249380 A1 | 12/2004 | Glascott |
| 2004/0249461 A1 | 12/2004 | Ferree |
| 2005/0004573 A1 | 1/2005 | Abdou |
| 2005/0021041 A1 | 1/2005 | Michelson |
| 2005/0033432 A1 | 2/2005 | Gordon et al. |
| 2005/0038511 A1 | 2/2005 | Martz et al. |
| 2005/0085909 A1 | 4/2005 | Eisermann |
| 2005/0119747 A1 | 6/2005 | Fabris et al. |
| 2005/0149188 A1 | 7/2005 | Cook et al. |
| 2005/0159756 A1 | 7/2005 | Ray |
| 2005/0159815 A1 | 7/2005 | Kamimura et al. |
| 2005/0171541 A1 | 8/2005 | Boehm, Jr. et al. |
| 2005/0171610 A1 | 8/2005 | Humphreys et al. |
| 2005/0177163 A1 | 8/2005 | Abdou et al. |
| 2005/0222683 A1 | 10/2005 | Berry |
| 2005/0251258 A1 | 11/2005 | Jackson |
| 2005/0273120 A1 | 12/2005 | Abdou et al. |
| 2005/0273171 A1 | 12/2005 | Gordon et al. |
| 2005/0278026 A1 | 12/2005 | Gordon et al. |
| 2005/0283244 A1 | 12/2005 | Gordon et al. |
| 2005/0283245 A1 | 12/2005 | Gordon et al. |
| 2005/0288669 A1 | 12/2005 | Abdou et al. |
| 2006/0004453 A1 | 1/2006 | Bartish, Jr. et al. |
| 2006/0058878 A1 | 3/2006 | Michelson |
| 2006/0074488 A1 | 4/2006 | Abdou et al. |
| 2006/0084981 A1 | 4/2006 | Shluzas |
| 2006/0089656 A1 | 4/2006 | Allard et al. |
| 2006/0089718 A1 | 4/2006 | Zucherman et al. |
| 2006/0122701 A1 | 6/2006 | Kiester |
| 2006/0129244 A1 | 6/2006 | Ensign |
| 2006/0142858 A1 | 6/2006 | Colleran et al. |
| 2006/0149278 A1 | 7/2006 | Abdou |
| 2006/0149284 A1 | 7/2006 | McCormack et al. |
| 2006/0149385 A1 | 7/2006 | McKay |
| 2006/0195192 A1 | 8/2006 | Gordon et al. |
| 2006/0217710 A1 | 9/2006 | Abdou |
| 2006/0217731 A1 | 9/2006 | Gil et al. |
| 2006/0229615 A1 | 10/2006 | Abdou et al. |
| 2006/0229729 A1 | 10/2006 | Gordon et al. |
| 2006/0241641 A1 | 10/2006 | Albans et al. |
| 2006/0247655 A1 | 11/2006 | Francis et al. |
| 2006/0247679 A1 | 11/2006 | Peterman |
| 2006/0247778 A1 | 11/2006 | Ferree et al. |
| 2006/0253201 A1 | 11/2006 | McLuen |
| 2007/0016218 A1 | 1/2007 | Winslow et al. |
| 2007/0043442 A1 | 2/2007 | Abernathie et al. |
| 2007/0049935 A1 | 3/2007 | Edidin et al. |
| 2007/0050030 A1 | 3/2007 | Kim |
| 2007/0050032 A1 | 3/2007 | Gittings et al. |
| 2007/0055377 A1 | 3/2007 | Hanson et al. |
| 2007/0093828 A1 | 4/2007 | Abdou et al. |
| 2007/0106383 A1 | 5/2007 | Abdou et al. |
| 2007/0123884 A1 | 5/2007 | Abdou |
| 2007/0161962 A1 | 7/2007 | Edie et al. |
| 2007/0162127 A1 | 7/2007 | Peterman et al. |
| 2007/0162138 A1 | 7/2007 | Heinz |
| 2007/0179614 A1 | 8/2007 | Heinz et al. |
| 2007/0191861 A1 | 8/2007 | Allard et al. |
| 2007/0191951 A1 | 8/2007 | Branch, Jr. et al. |
| 2007/0225812 A1 | 9/2007 | Gill |
| 2007/0255415 A1 | 11/2007 | Edie et al. |
| 2007/0270963 A1 | 11/2007 | Melkent et al. |
| 2007/0270968 A1 | 11/2007 | Baynham et al. |
| 2007/0282448 A1 | 12/2007 | Abdou |
| 2007/0293949 A1 | 12/2007 | Salerni et al. |
| 2007/0299521 A1 | 12/2007 | Glenn et al. |
| 2008/0021559 A1 | 1/2008 | Thramann |
| 2008/0027544 A1 | 1/2008 | Melkent |
| 2008/0045968 A1 | 2/2008 | Yu et al. |
| 2008/0065222 A1 | 3/2008 | Hamada |
| 2008/0119853 A1 | 5/2008 | Felt et al. |
| 2008/0133014 A1 | 6/2008 | Gately et al. |
| 2008/0133016 A1 | 6/2008 | Heinz |
| 2008/0133017 A1 | 6/2008 | Beyar et al. |
| 2008/0140204 A1 | 6/2008 | Heinz |
| 2008/0140207 A1 | 6/2008 | Olmos et al. |
| 2008/0161821 A1 | 7/2008 | Heinz |
| 2008/0167657 A1 | 7/2008 | Greenhalgh |
| 2008/0183204 A1 | 7/2008 | Greenhalgh et al. |
| 2008/0183211 A1 | 7/2008 | Lamborne et al. |
| 2008/0188941 A1 | 8/2008 | Grotz |
| 2008/0281346 A1 | 11/2008 | Greenhalgh et al. |
| 2008/0288073 A1 | 11/2008 | Renganath et al. |
| 2008/0300598 A1 | 12/2008 | Barreiro et al. |
| 2008/0300686 A1 | 12/2008 | Khoo |
| 2008/0312743 A1 | 12/2008 | Vila et al. |
| 2008/0319487 A1 | 12/2008 | Fielding et al. |
| 2008/0319549 A1 | 12/2008 | Greenhalgh et al. |
| 2009/0012623 A1 | 1/2009 | Sack et al. |
| 2009/0024217 A1 | 1/2009 | Levy et al. |
| 2009/0093884 A1 | 4/2009 | Bass |
| 2009/0125062 A1 | 5/2009 | Arnin |
| 2009/0149956 A1 | 6/2009 | Greenhalgh et al. |
| 2009/0149959 A1 | 6/2009 | Conner et al. |
| 2009/0187249 A1 | 7/2009 | Osman |
| 2009/0204218 A1 | 8/2009 | Richelsoph |
| 2009/0222100 A1 | 9/2009 | Cipoletti et al. |
| 2009/0228110 A1 | 9/2009 | McClintock |

(56) References Cited

U.S. PATENT DOCUMENTS

| | | |
|---|---|---|
| 2009/0240334 A1 | 9/2009 | Richelsoph |
| 2009/0270989 A1 | 10/2009 | Conner et al. |
| 2009/0281628 A1 | 11/2009 | Oglaza et al. |
| 2009/0292361 A1 | 11/2009 | Lopez |
| 2009/0299478 A1 | 12/2009 | Carls et al. |
| 2010/0049324 A1 | 2/2010 | Valdevit et al. |
| 2010/0070041 A1 | 3/2010 | Peterman et al. |
| 2010/0082109 A1 | 4/2010 | Greenhalgh et al. |
| 2010/0179657 A1 | 7/2010 | Greenhalgh et al. |
| 2010/0185291 A1 | 7/2010 | Jimenez et al. |
| 2010/0191336 A1 | 7/2010 | Greenhalgh |
| 2010/0204795 A1 | 8/2010 | Greenhalgh |
| 2010/0211176 A1 | 8/2010 | Greenhalgh |
| 2010/0222816 A1 | 9/2010 | Gabelberger et al. |
| 2010/0222884 A1 | 9/2010 | Greenhalgh et al. |
| 2010/0234952 A1 | 9/2010 | Peterman |
| 2010/0249933 A1 | 9/2010 | Trieu |
| 2010/0280622 A1 | 11/2010 | McKinley |
| 2010/0286779 A1 | 11/2010 | Thibodeau |
| 2010/0286780 A1 | 11/2010 | Dryer et al. |
| 2010/0292796 A1 | 11/2010 | Greenhalgh et al. |
| 2010/0305705 A1 | 12/2010 | Butler et al. |
| 2010/0331981 A1 | 12/2010 | Mohammed |
| 2010/0331985 A1 | 12/2010 | Gordon et al. |
| 2011/0029083 A1 | 2/2011 | Hynes et al. |
| 2011/0035011 A1 | 2/2011 | Cain |
| 2011/0093074 A1 | 4/2011 | Glerum et al. |
| 2011/0125266 A1 | 5/2011 | Rodgers et al. |
| 2011/0213465 A1 | 9/2011 | Landry et al. |
| 2011/0251693 A1 | 10/2011 | Barreiro et al. |
| 2011/0288644 A1 | 11/2011 | Gray et al. |
| 2011/0288645 A1 | 11/2011 | Braddock, Jr. et al. |
| 2011/0301712 A1 | 12/2011 | Palmatier et al. |
| 2012/0029639 A1 | 2/2012 | Blackwell et al. |
| 2012/0197401 A1 | 8/2012 | Duncan et al. |
| 2012/0197402 A1 | 8/2012 | Blackwell et al. |
| 2012/0277864 A1 | 11/2012 | Brodke et al. |
| 2013/0041471 A1 | 2/2013 | Siegal et al. |
| 2013/0150970 A1 | 6/2013 | Thaiyananthan |
| 2013/0274884 A1 | 10/2013 | Matsumoto et al. |
| 2013/0325128 A1 | 12/2013 | Perloff et al. |
| 2014/0277490 A1 | 9/2014 | Perloff et al. |
| 2014/0277502 A1 | 9/2014 | Schiffman et al. |
| 2015/0057755 A1 | 2/2015 | Suddaby et al. |

FOREIGN PATENT DOCUMENTS

| | | |
|---|---|---|
| WO | WO-9000037 A1 | 1/1990 |
| WO | WO-9723174 A1 | 7/1997 |
| WO | WO-9730666 A2 | 8/1997 |
| WO | WO-9938463 A2 | 8/1999 |
| WO | WO-0023015 A1 | 4/2000 |
| WO | WO-0128465 A2 | 4/2001 |
| WO | WO-0145577 A2 | 6/2001 |
| WO | WO-0211633 A2 | 2/2002 |
| WO | WO-02058600 A2 | 8/2002 |
| WO | WO-03051212 A2 | 6/2003 |
| WO | WO-2004032726 A2 | 4/2004 |
| WO | WO-2004062482 A2 | 7/2004 |
| WO | WO-2004093702 A2 | 11/2004 |
| WO | WO-2005122922 A2 | 12/2005 |
| WO | WO-2006041963 A2 | 4/2006 |
| WO | WO-2006042335 A1 | 4/2006 |
| WO | WO-2006058221 A2 | 6/2006 |
| WO | WO-2006089292 A2 | 8/2006 |
| WO | WO-2006096756 A2 | 9/2006 |
| WO | WO-2007041648 A2 | 4/2007 |
| WO | WO-2007044705 A2 | 4/2007 |
| WO | WO-2007044836 A2 | 4/2007 |
| WO | WO-2007056516 A2 | 5/2007 |
| WO | WO-2007059207 A2 | 5/2007 |
| WO | WO-2008085521 A1 | 7/2008 |

OTHER PUBLICATIONS

Dar, et al., The Epiphyses Ring: A Long Forgotten Anatomical Structure with Significant Physiological Function (PA 1976). May 15, 2011; 36 (11): 850-6.

Netter F., Atlas of Human Anatomy, 3rd Edition, Icon Learning Systems, Tegerboro, New Jersey (2004).

Vaccaro, et al., Principles of Practice of Spine Surgery; Mosby Press, Philadelphia, PA; 2003.

Wohns R.N.W., et al., Day Surgery for Anterior Cervical Microdiskectomy: Experience with 75 Cases, Jul. 11, 2002, pp. 1-3.

Yerby S., et al., "The Effect of Cutting Flute Design on the Insertion and Pullout Properties of Self-tapping Bone Screws," Jul. 2, 2002, pp. 1-2.

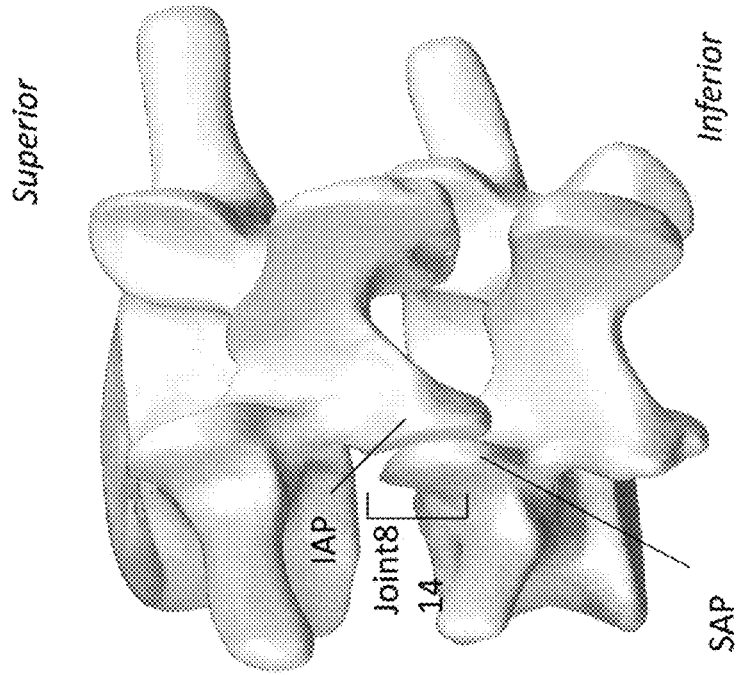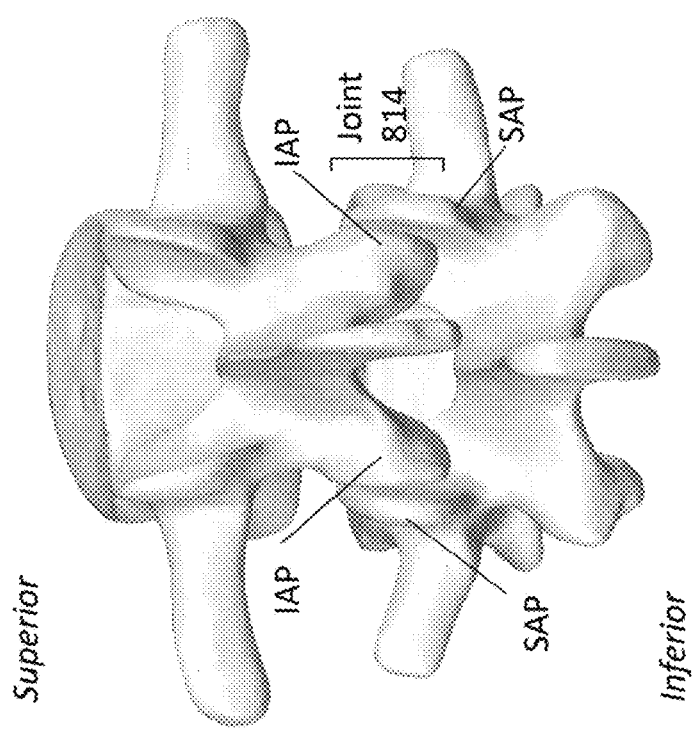

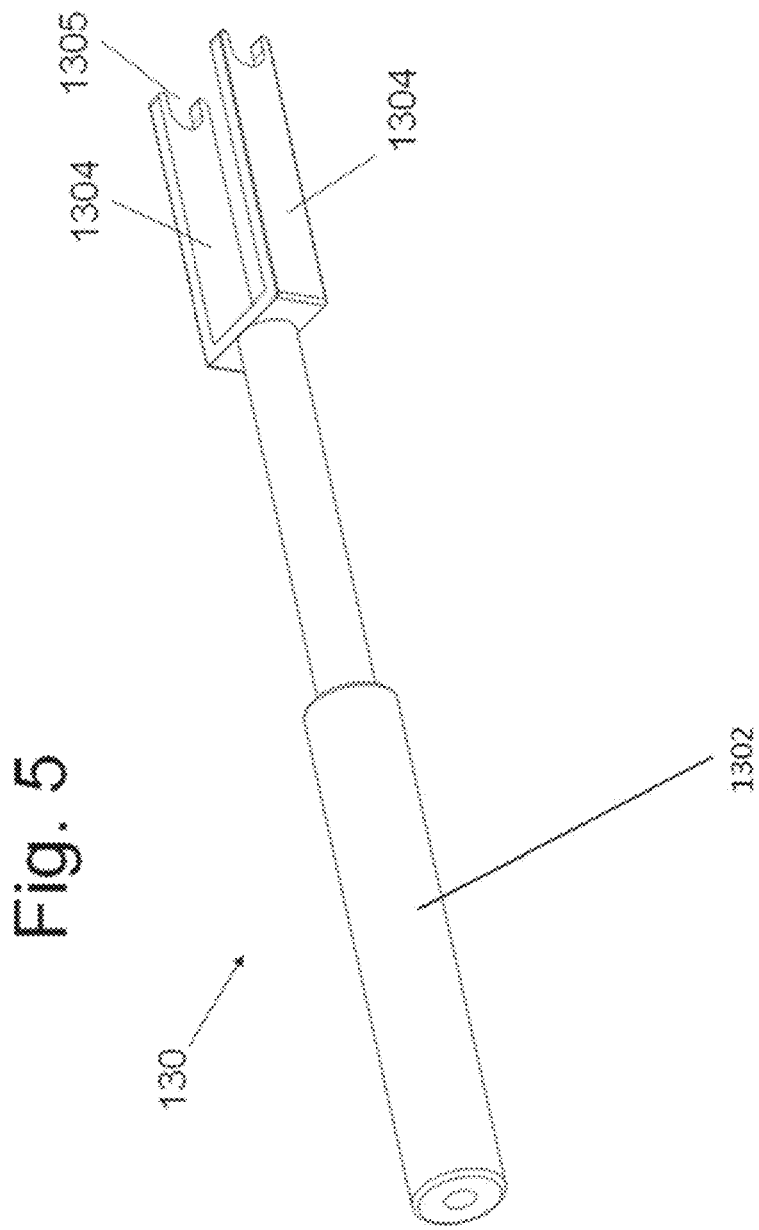

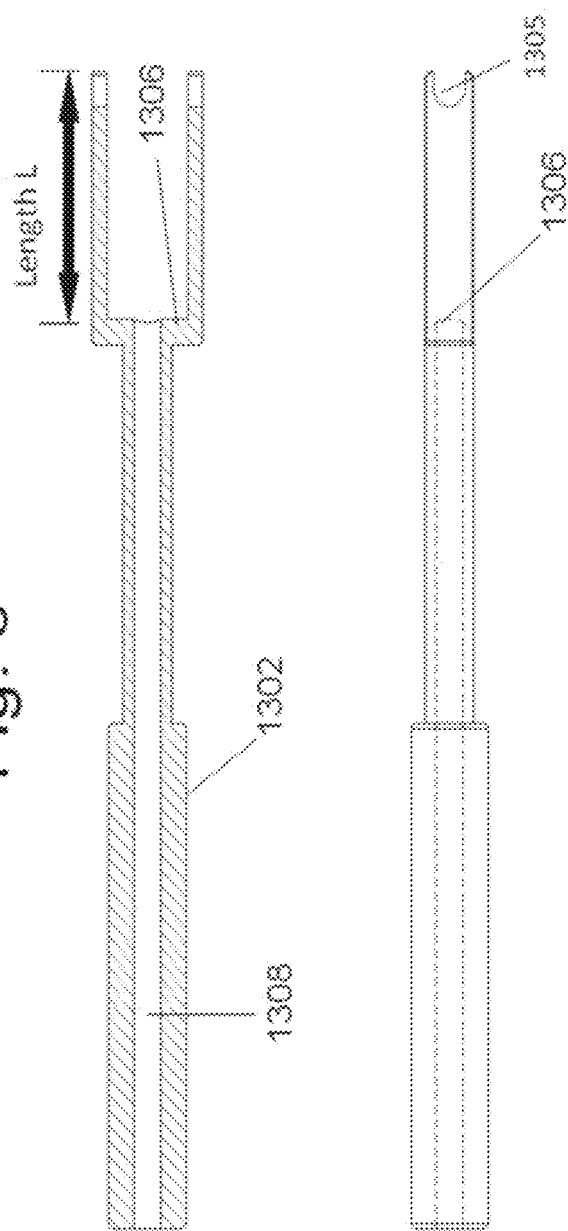

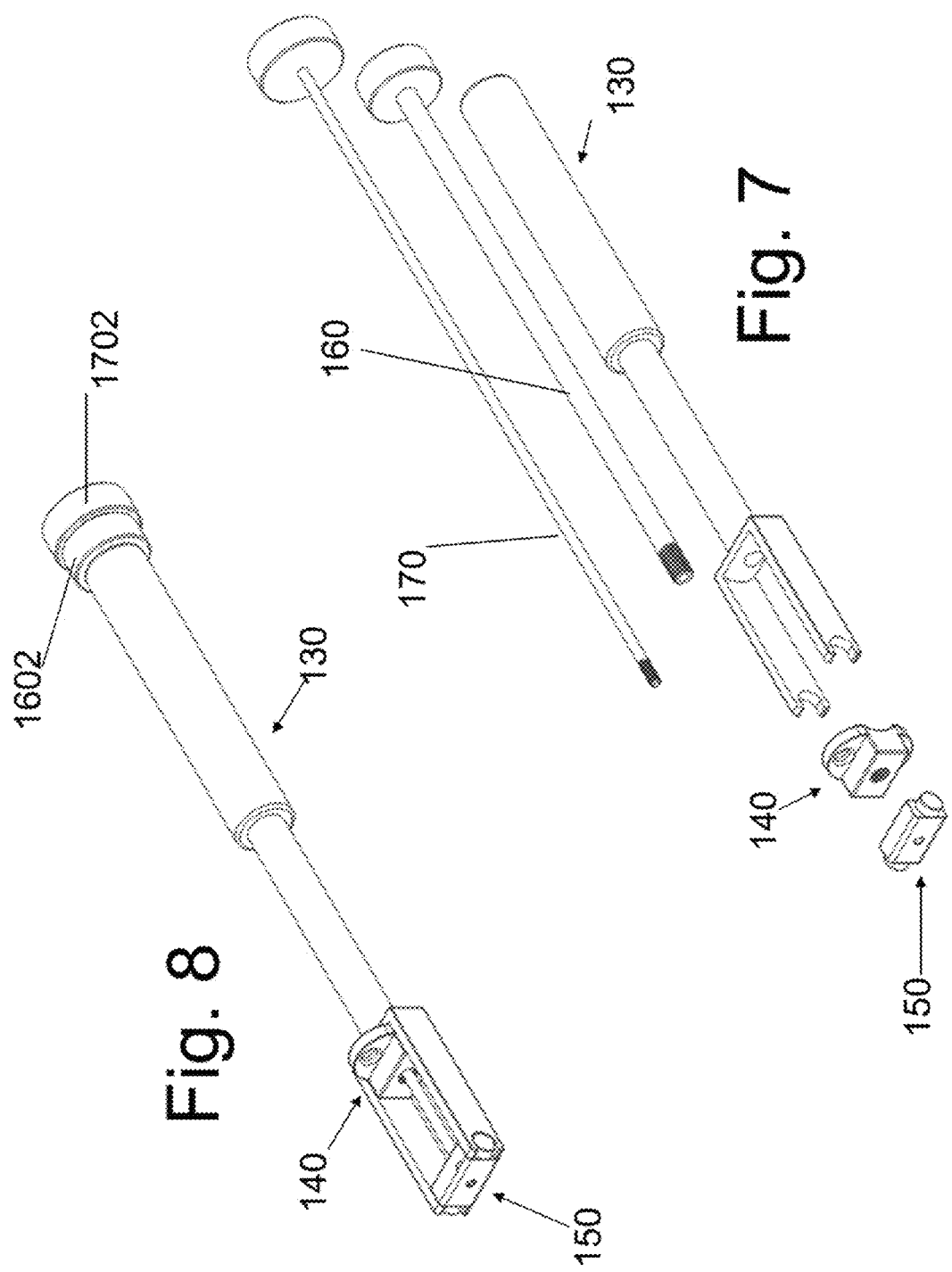

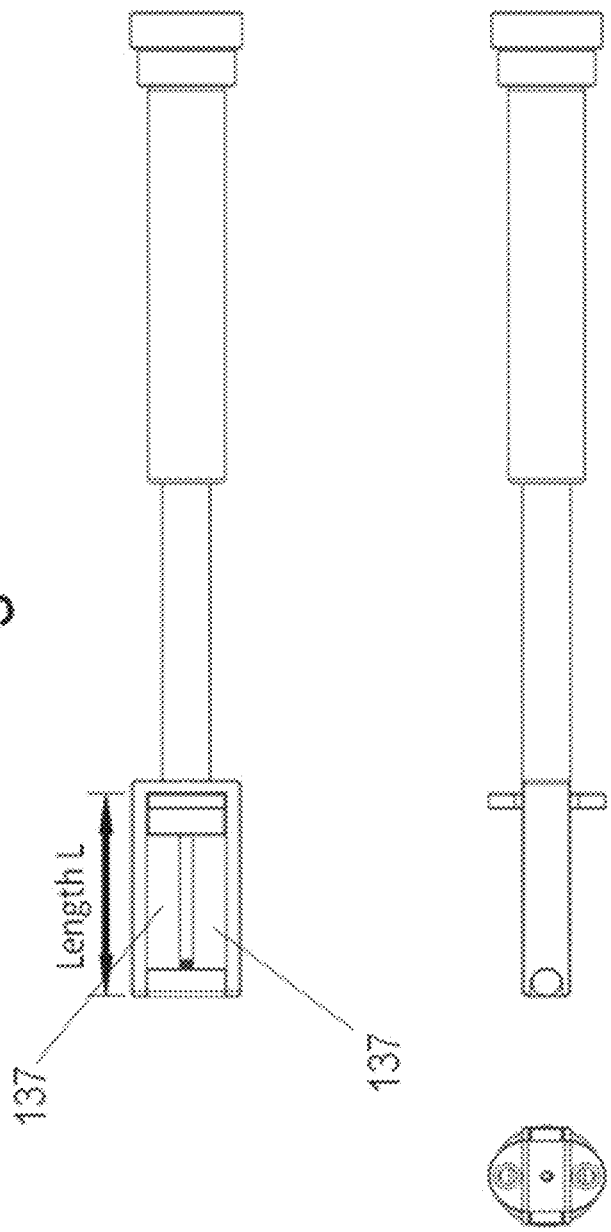

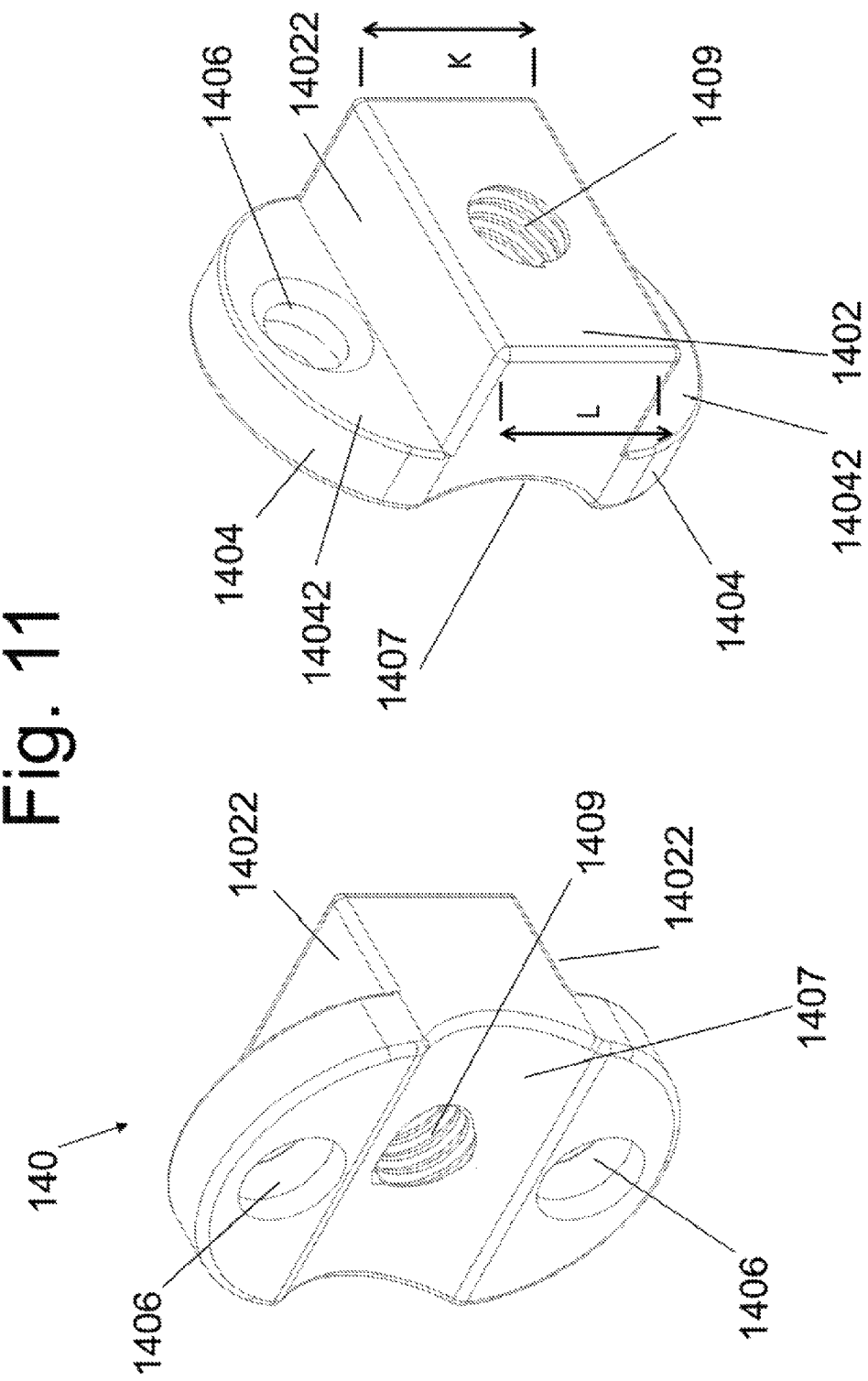

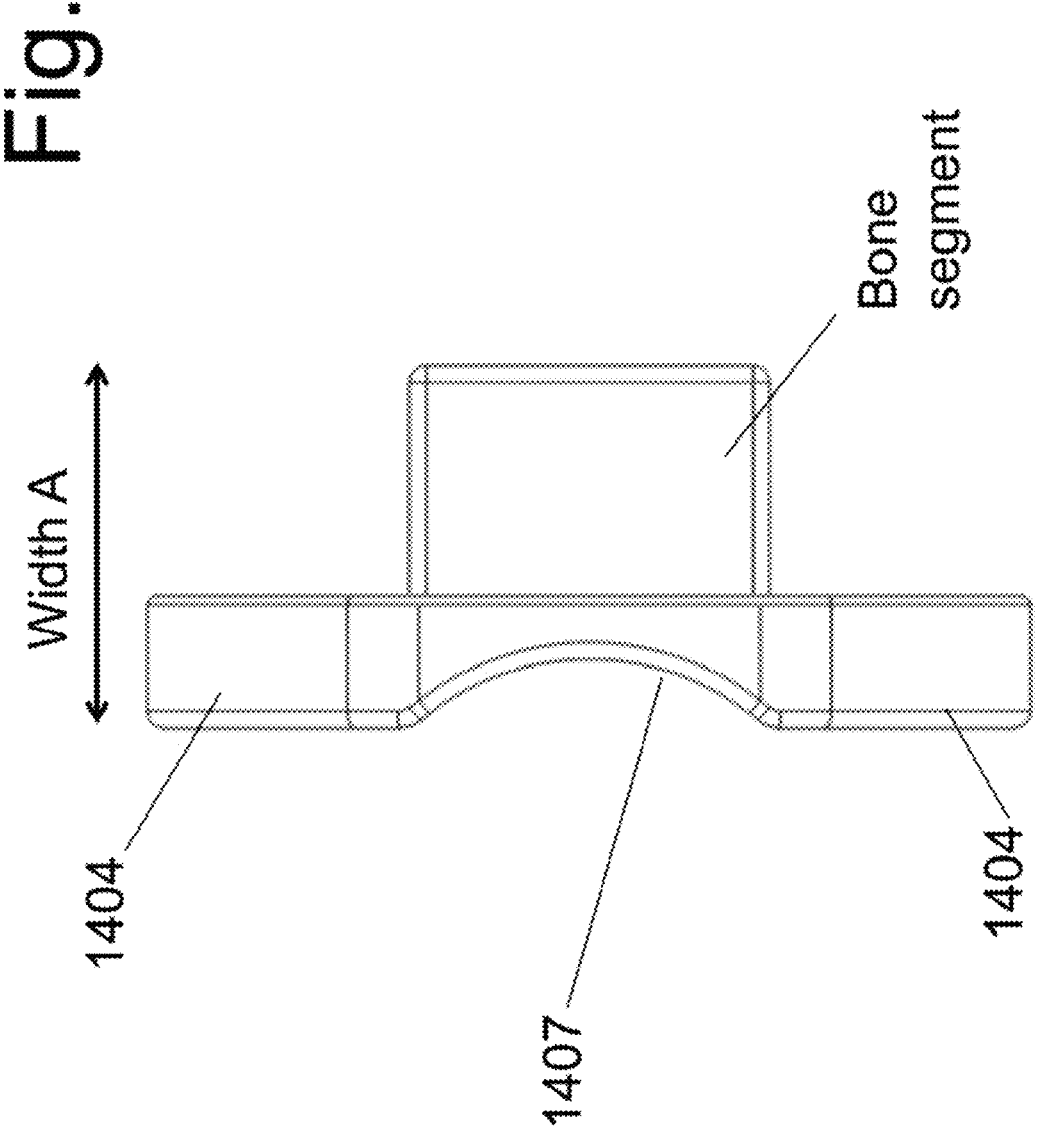

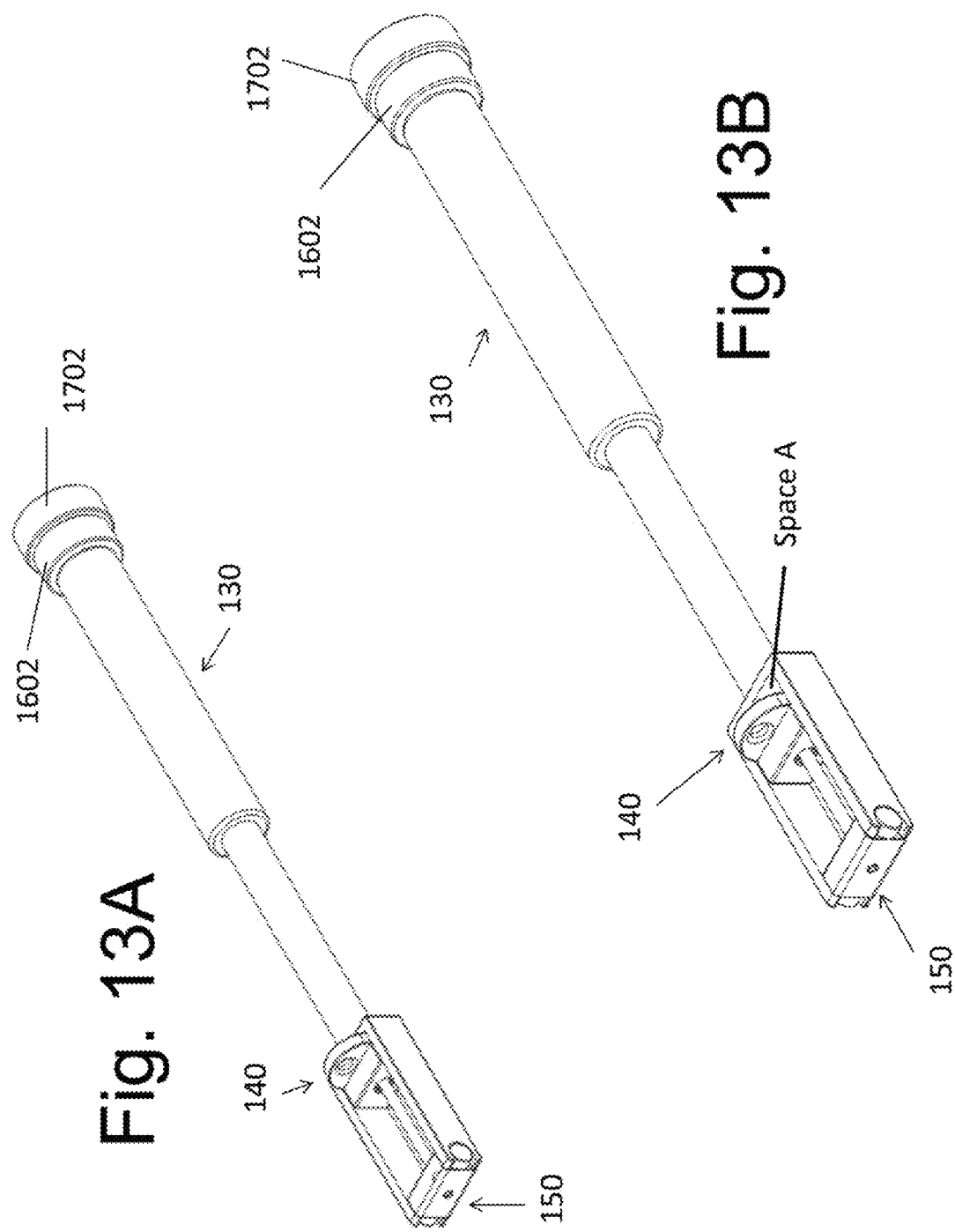

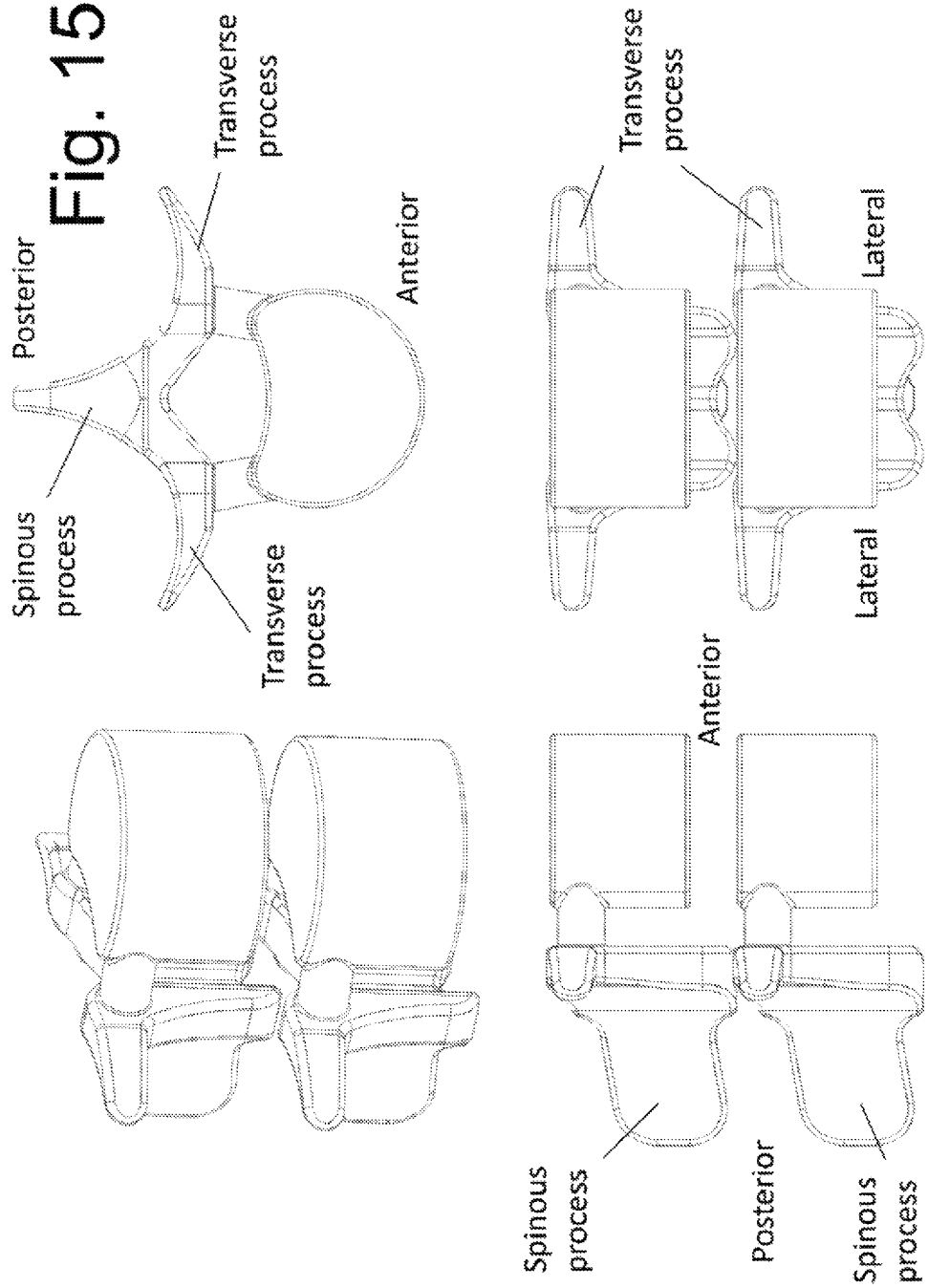

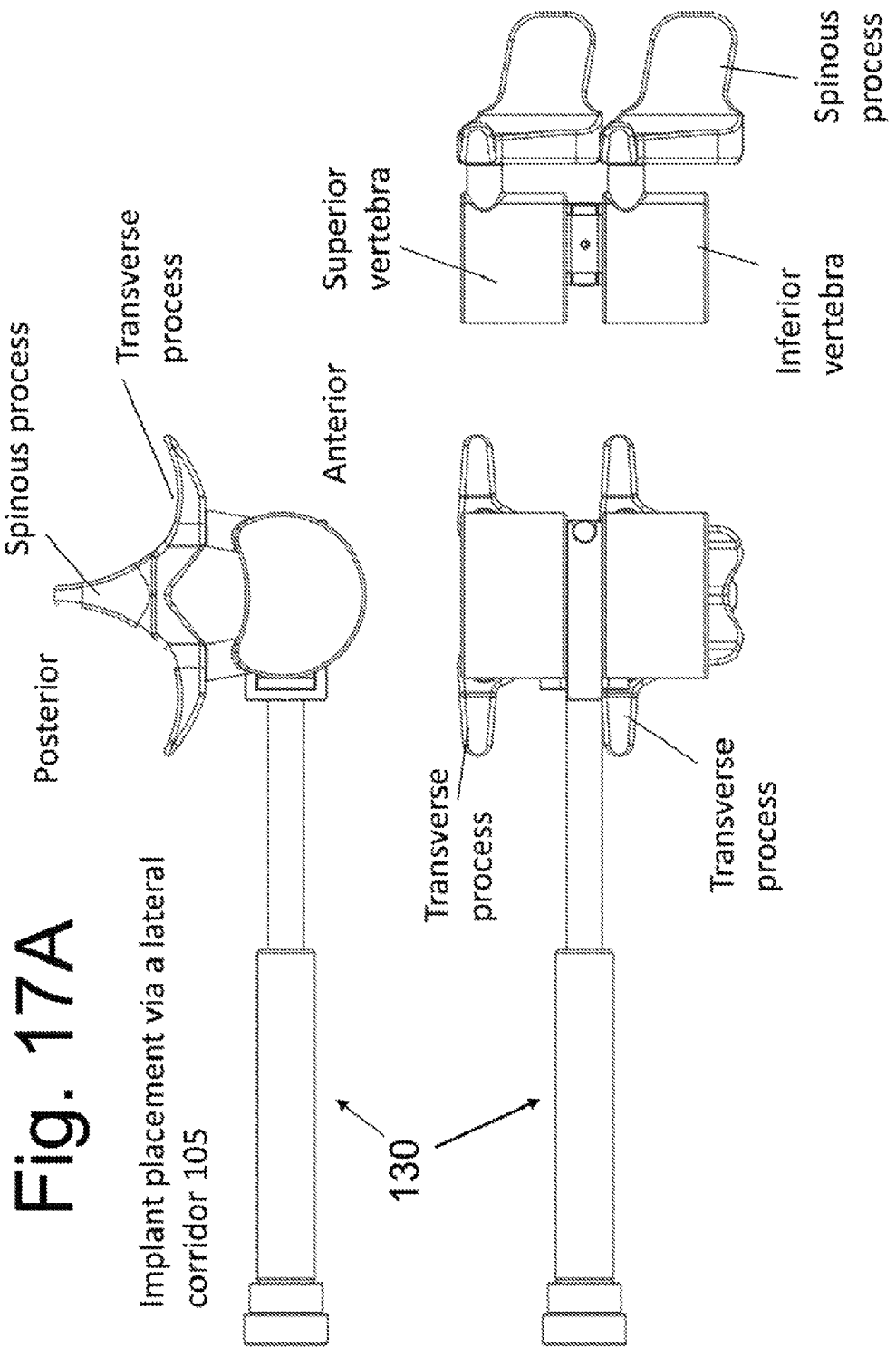

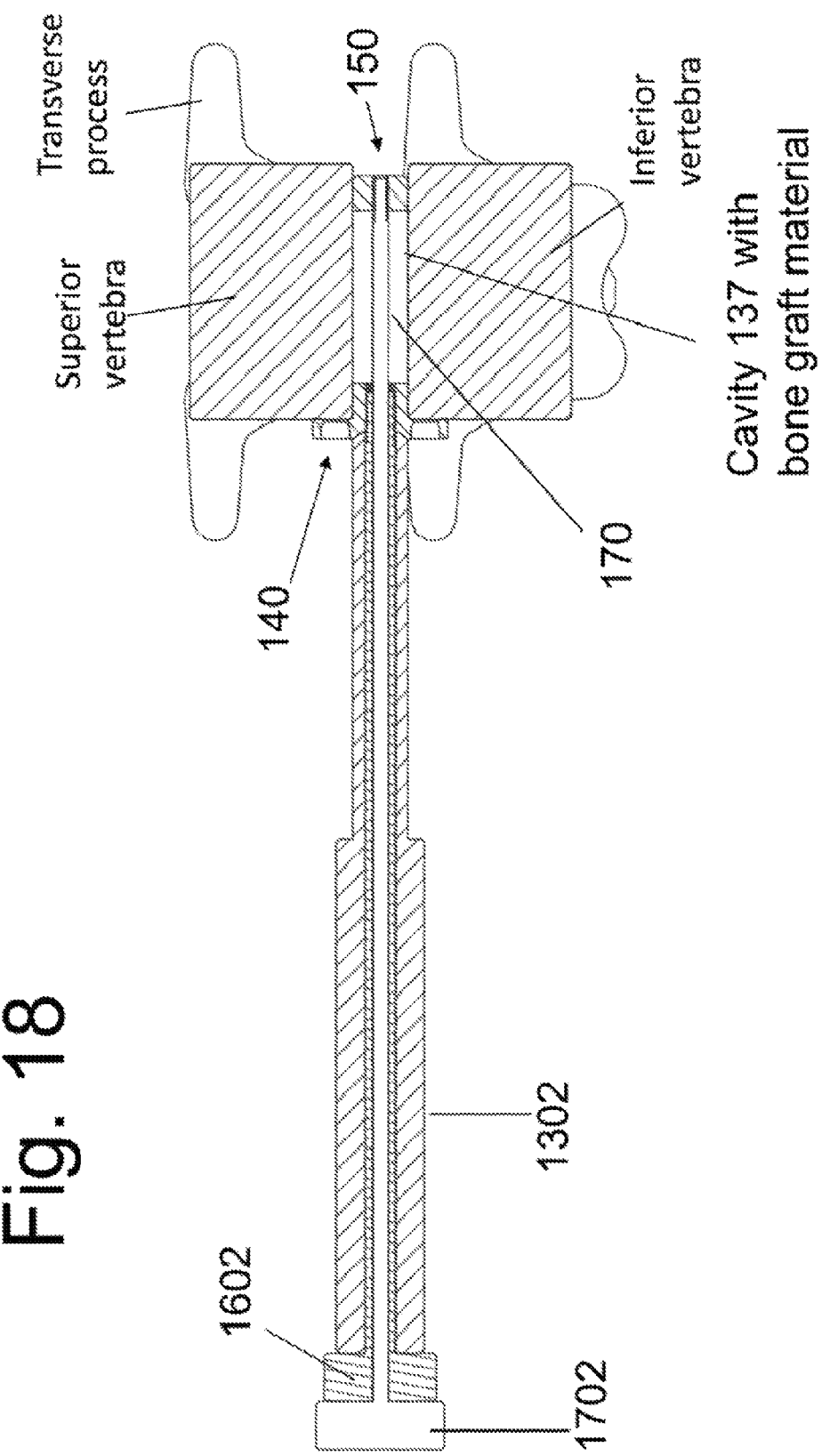

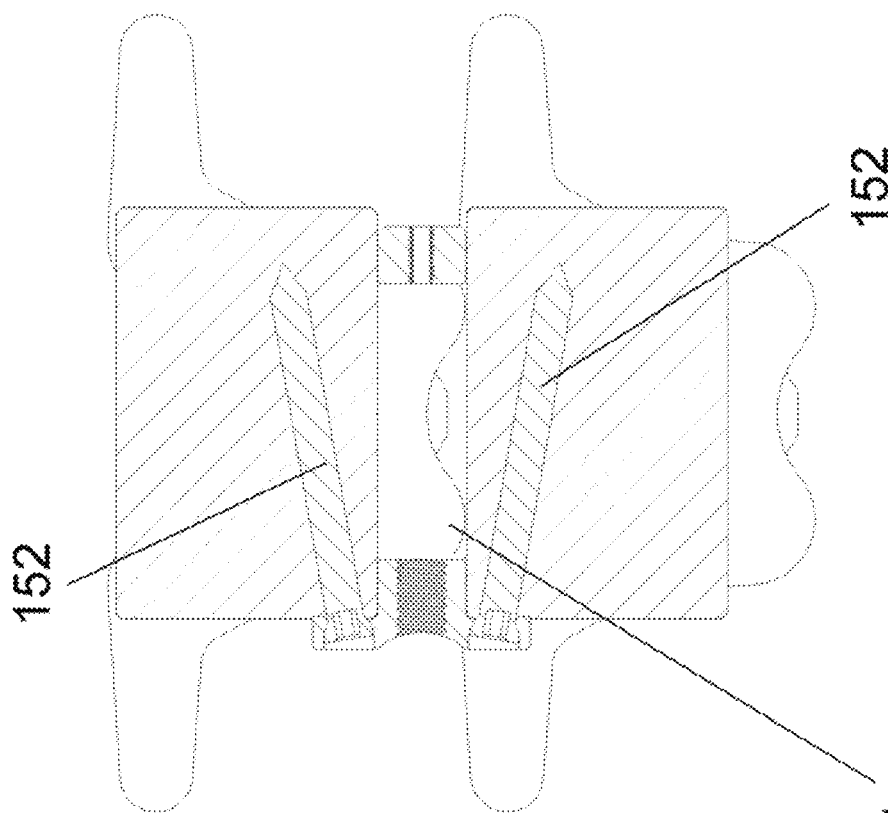
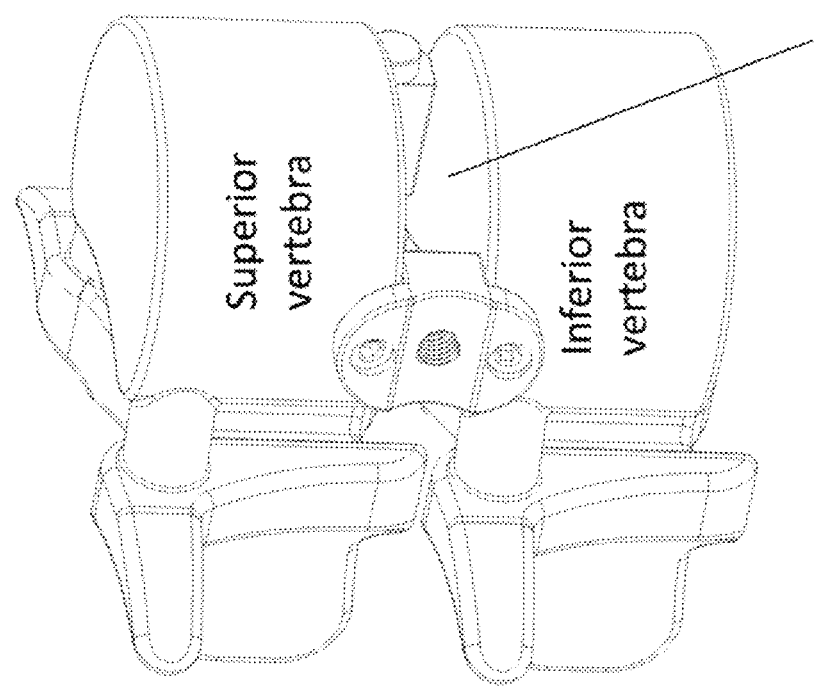
Fig. 19B
Fig. 19A

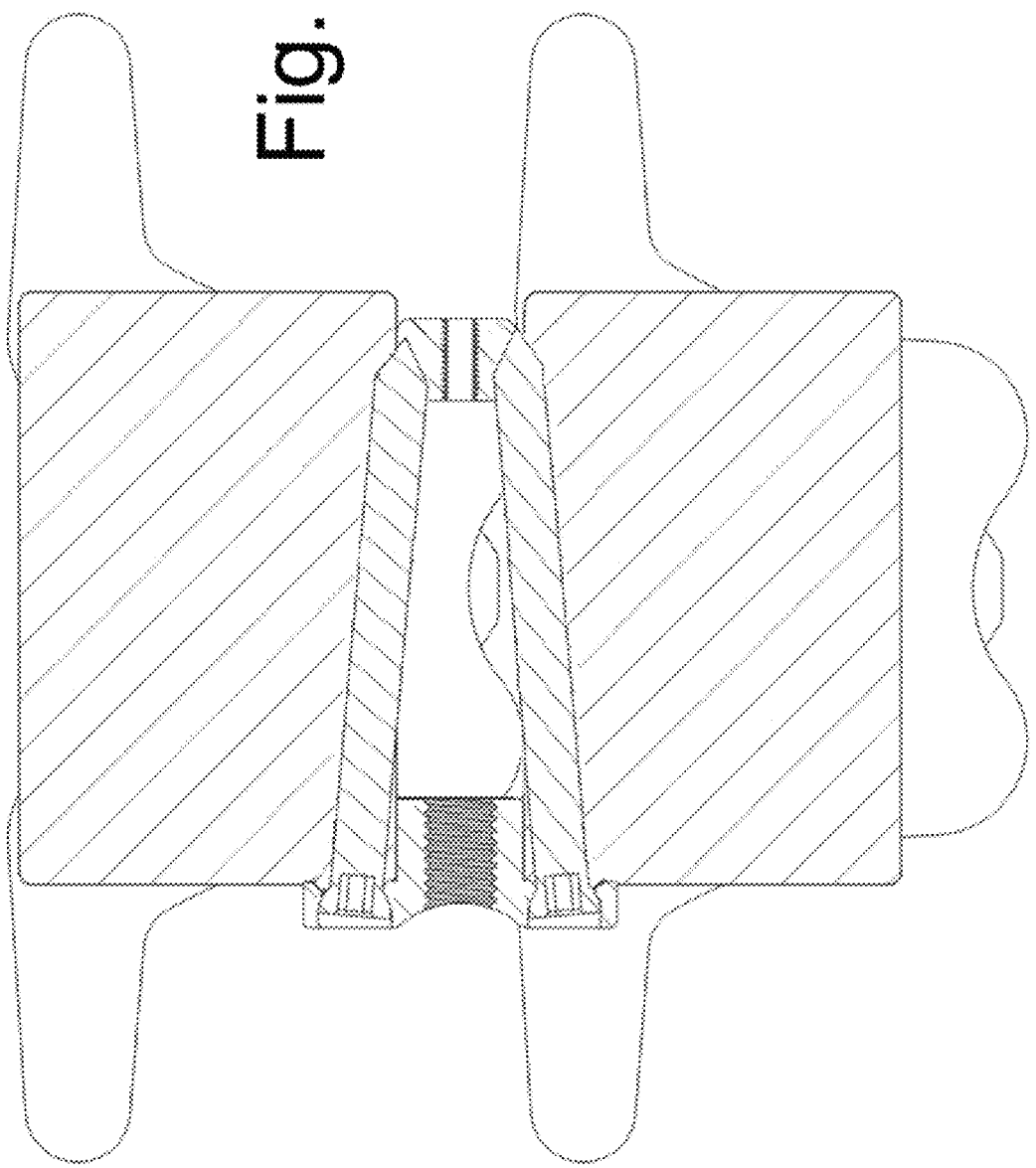

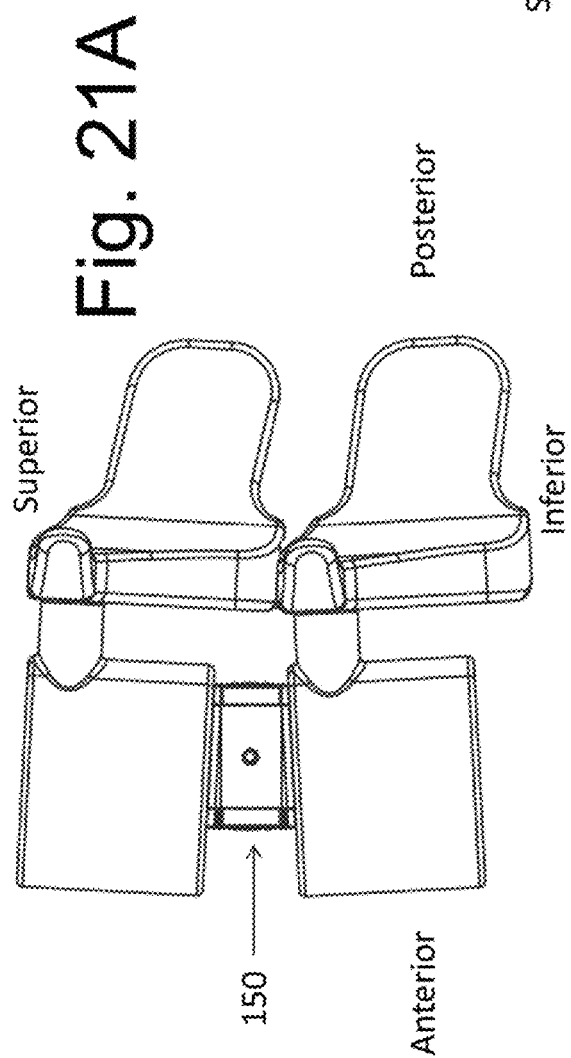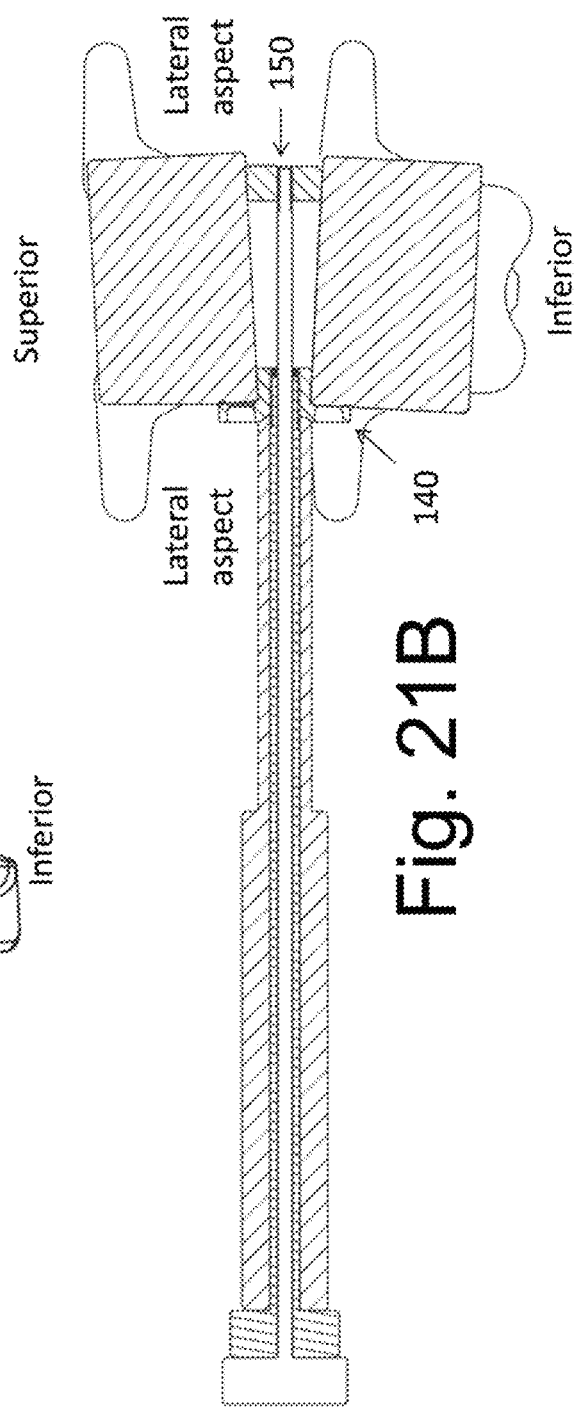

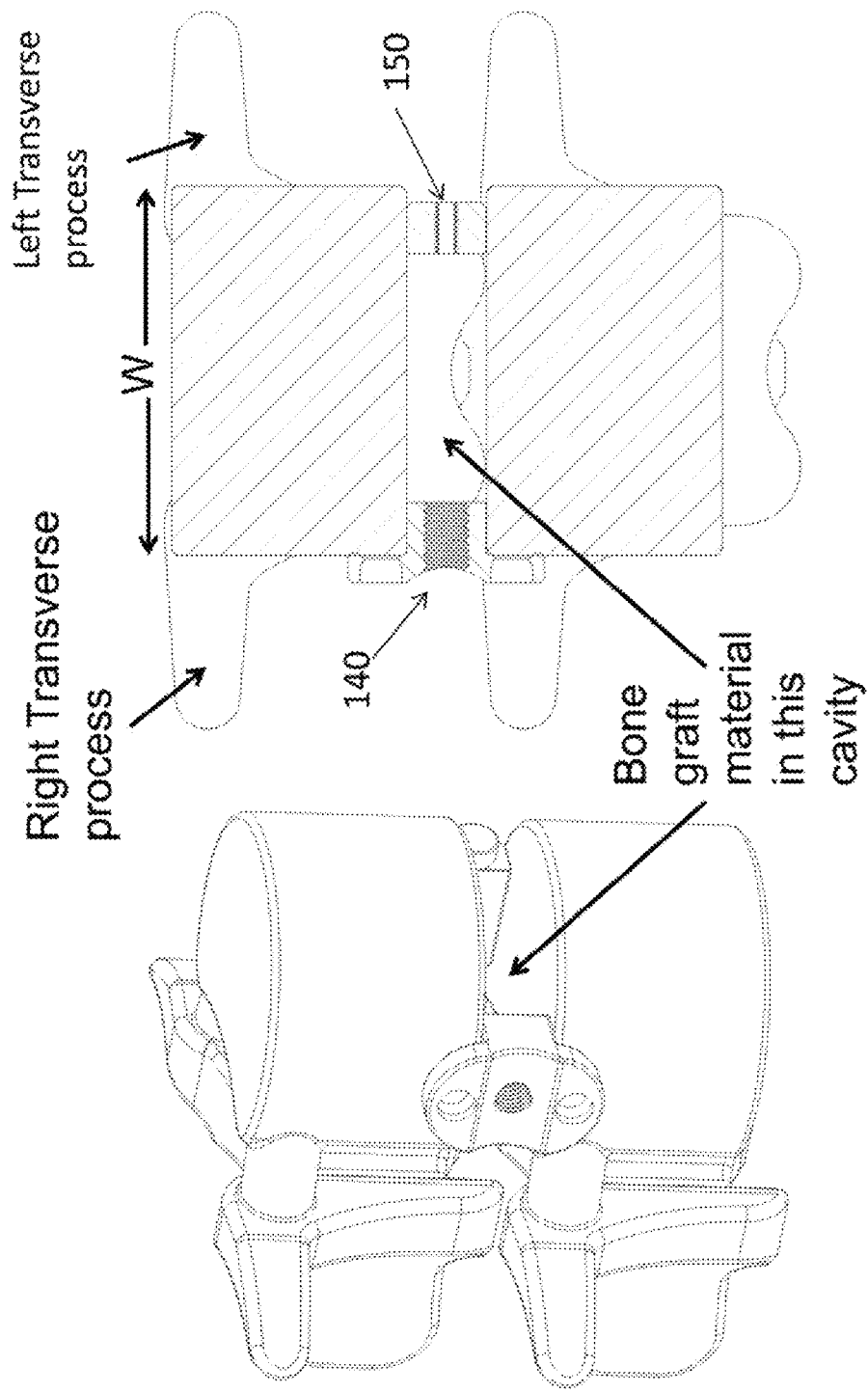

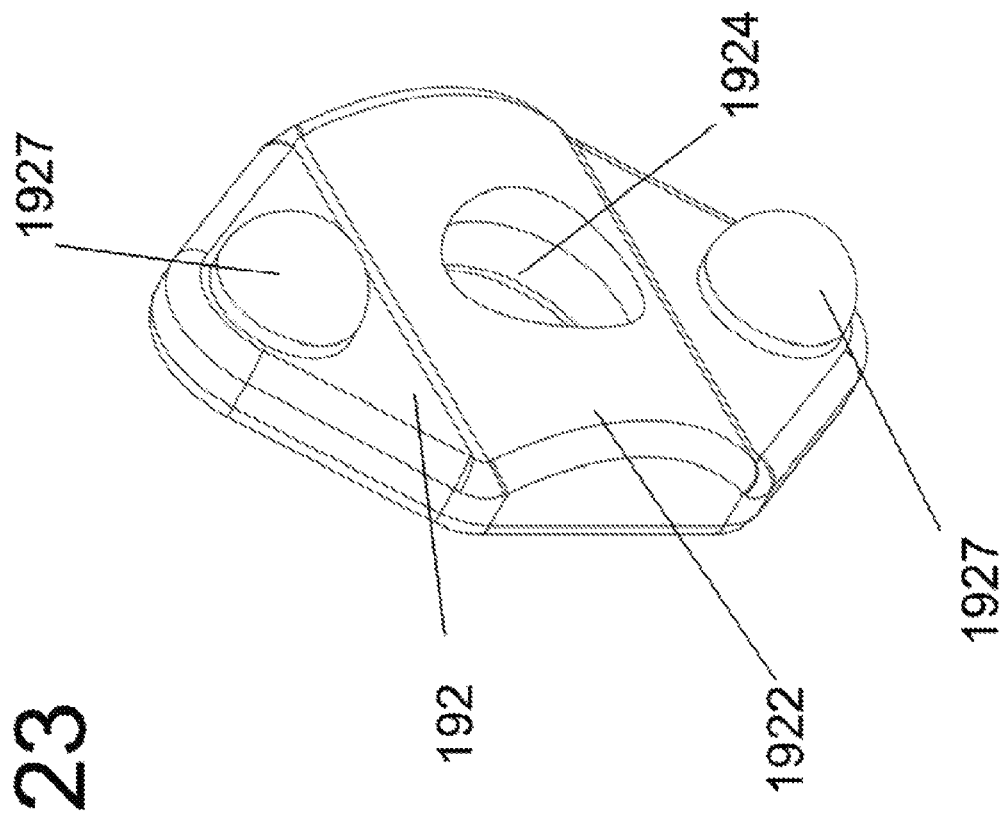
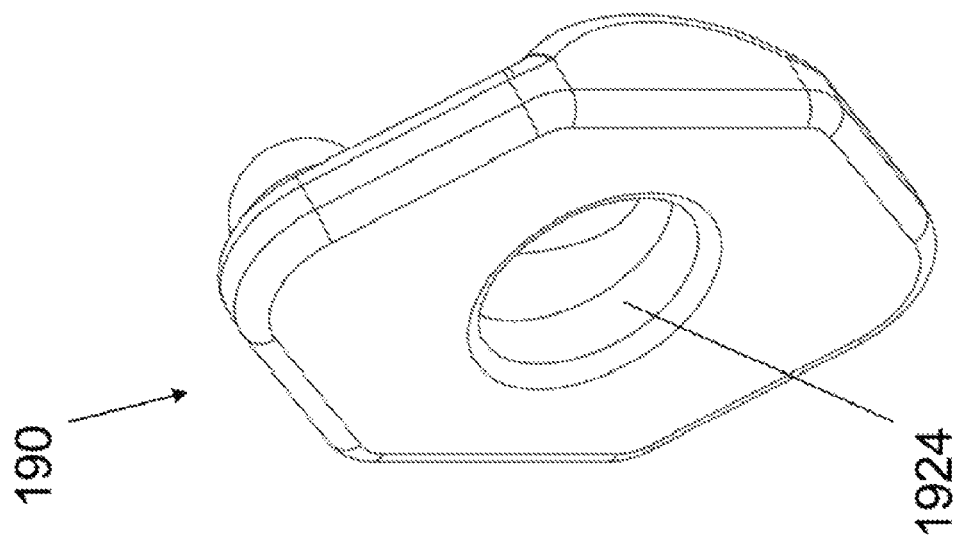
Fig. 23

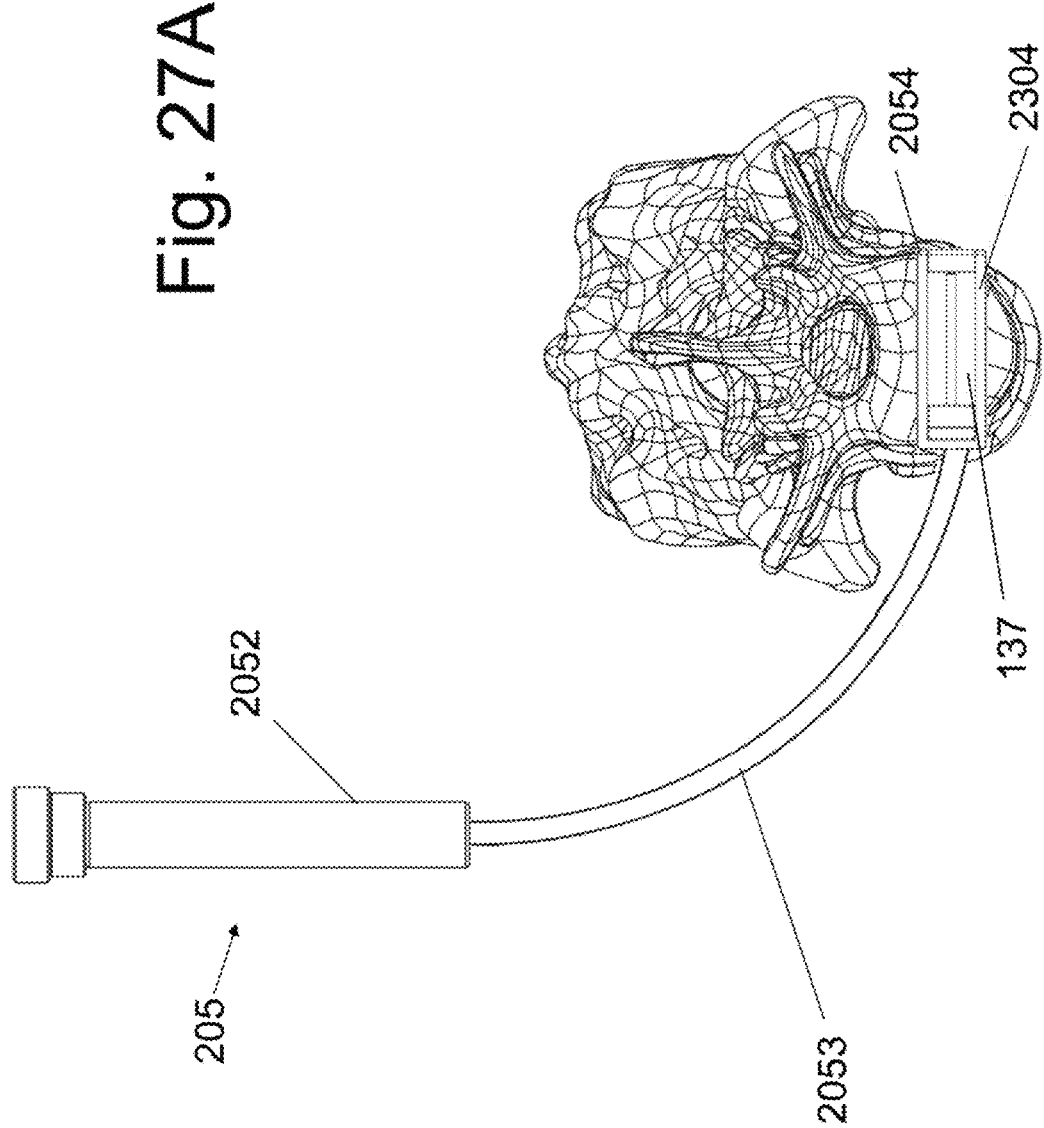

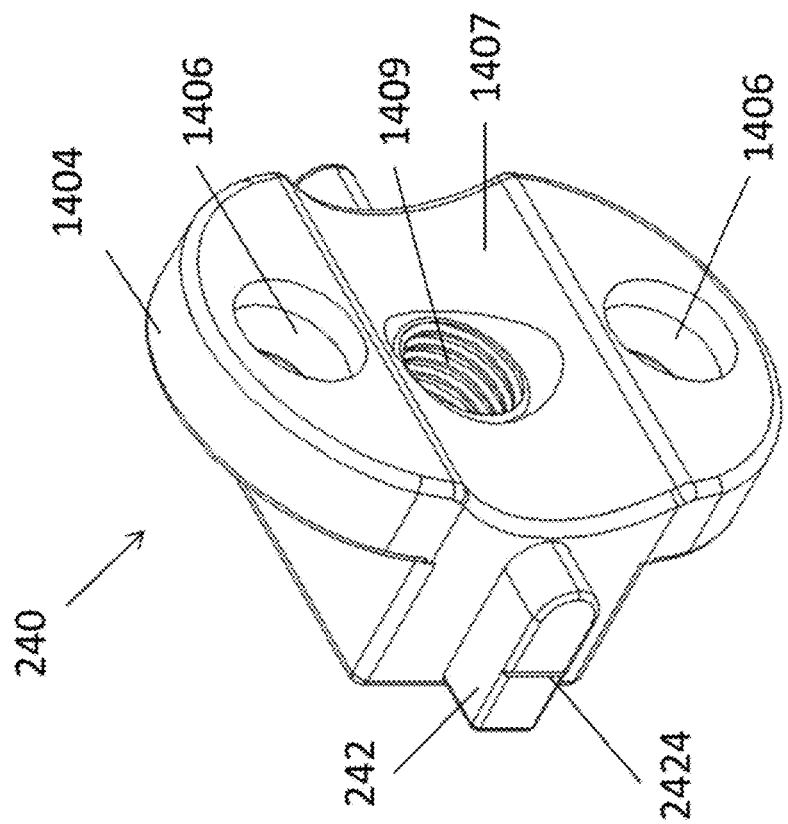
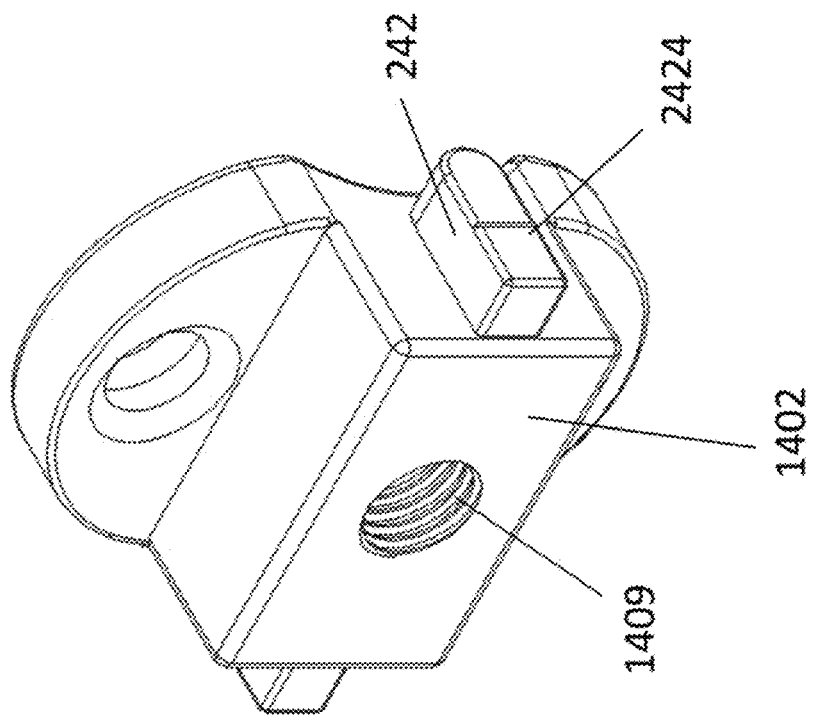
Fig. 29

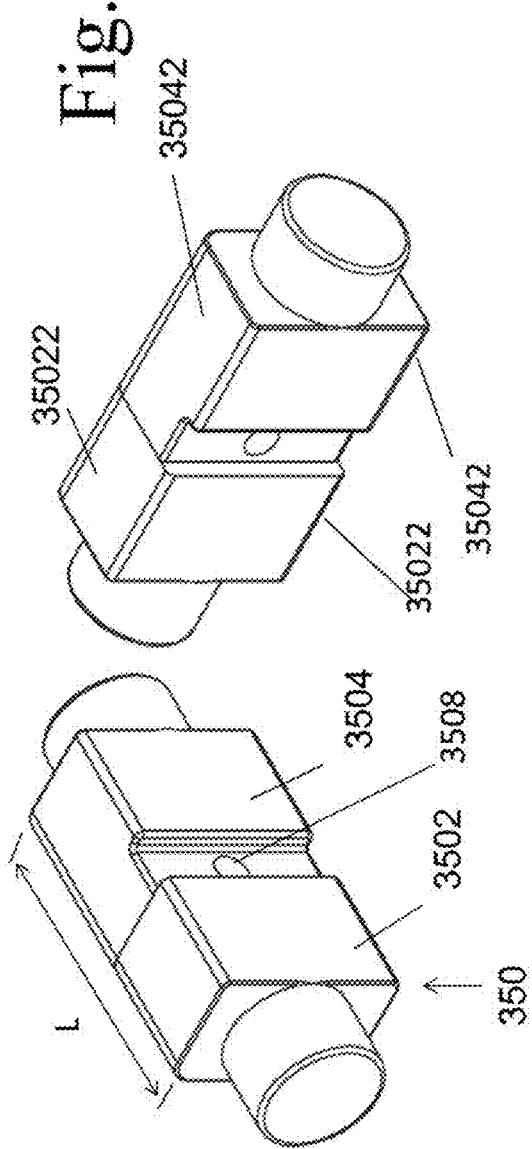
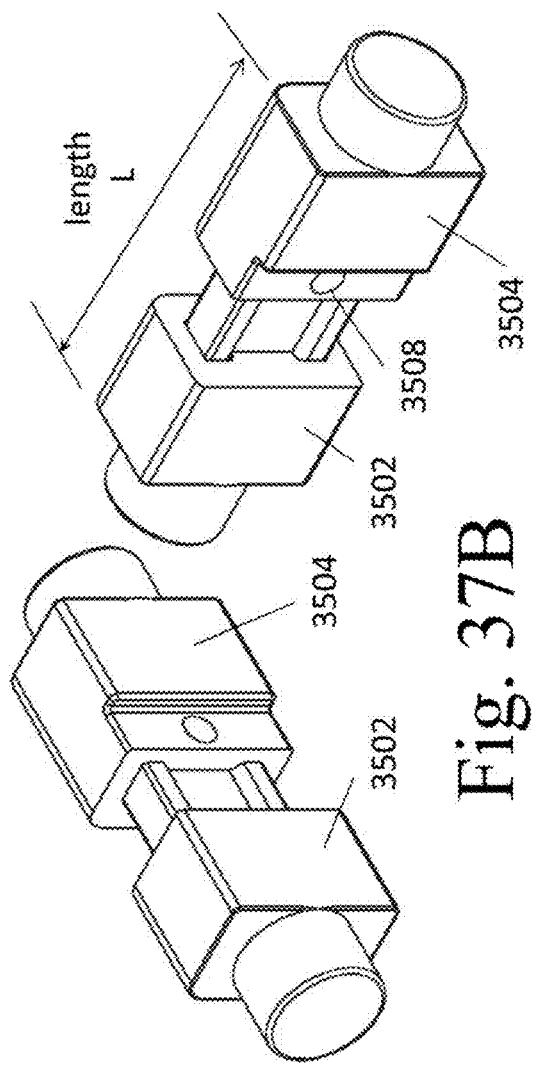

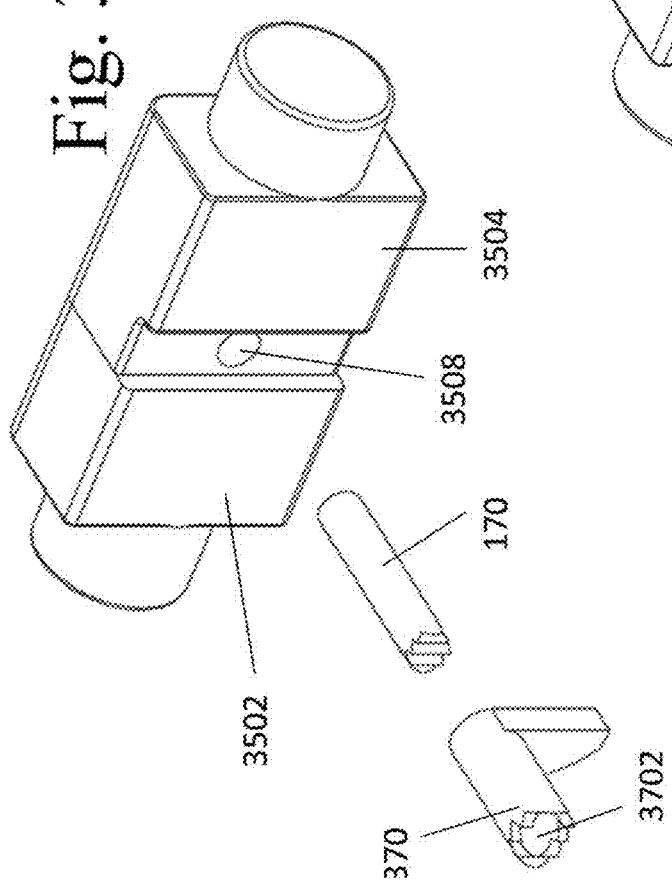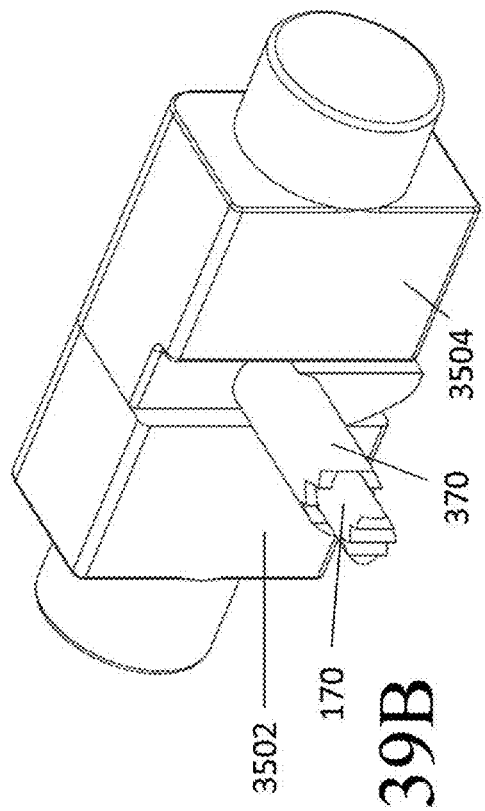
Fig. 39A
Fig. 39B

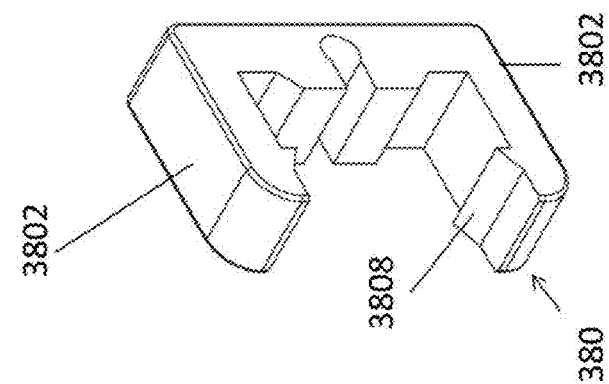
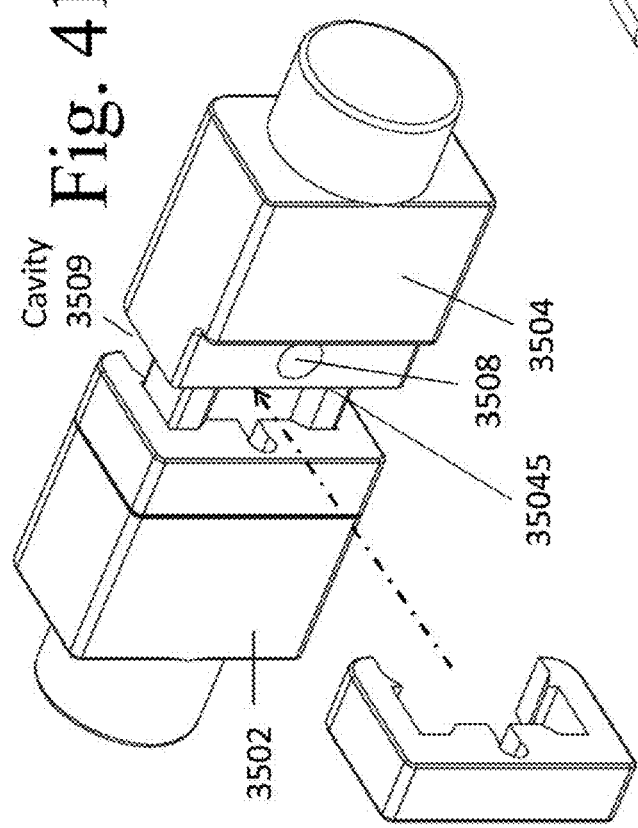
Fig. 41A
Fig. 41B

SPINAL FIXATION DEVICES AND METHODS OF USE

RELATED APPLICATIONS

This application is a divisional of and claims priority to co-pending U.S. patent application Ser. No. 15/478,088 filed on Apr. 3, 2017 entitled "SPINAL FIXATION DEVICES AND METHODS OF USE", which is incorporated herein by reference in its entirety. U.S. patent application Ser. No. 15/478,088 is a divisional of U.S. patent application Ser. No. 15/132,095 filed on Apr. 18, 2016 and issued as U.S. Pat. No. 9,610,176 on Apr. 4, 2017, which is a divisional of and claims priority to U.S. patent application Ser. No. 14/500,815 filed on Sep. 29, 2014 and issued as U.S. Pat. No. 9,314,350 on Apr. 19, 2016, which is a continuation of and claims priority to U.S. patent application Ser. No. 13/624,792 filed on Sep. 21, 2012 and issued as U.S. Pat. No. 8,845,728 on Sep. 30, 2014, each of the same title and each also incorporated herein by reference in its entirety. U.S. patent application Ser. No. 13/624,792 claims priority to U.S. Provisional Patent Application Ser. No. 61/626,340 entitled "DEVICES AND METHODS FOR INTER-VERTEBRAL ORTHOPEDIC DEVICE PLACEMENT" by Samy Abdou and filed Sep. 23, 2011, which is additionally incorporated herein by reference in its entirety.

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

BACKGROUND

1. Field of the Disclosure

The present disclosure relates generally to the field of to bone fixation systems, components thereof, and methods of implant placement used to adjust, align and maintain the spatial relationship(s) of adjacent bones or bony fragments after surgical reconstruction of skeletal segments. More particularly, the present disclosure is related in one exemplary aspect to devices that fixate the spinous processes at one vertebral level with the spinous process of another vertebra.

2. Description of Related Technology

Whether from degenerative disease, traumatic disruption, infection or neoplastic invasion, alteration in the anatomical relationships between the spinal vertebras can cause significant pain, deformity and disability. Spinal disease is a major health problem in the industrialized world and the surgical treatment of spinal pathology is an evolving discipline. The traditional surgical treatment of abnormal vertebral motion is the complete immobilization and bony fusion of the involved spinal segment and an extensive array of surgical techniques and implantable devices have been formulated to accomplish the treatment objective.

Vertebral fusion may be accomplished by using an anterior, lateral or posterior approach and each has particular advantages and draw backs. Frequently, circumferential fusion of the unstable level with fixation of both the anterior and posterior aspect of the spine is desired. This requires that patients undergo a combination of the aforementioned approaches. The anterior or lateral approaches are used to insert the bone graft and load bearing implants into the disc space between the adjacent vertebras while the posterior approach is used to place bone screws or similar fasteners that are used to immobilize the vertebral bodies.

Current implants to fuse the intervertebral disc space are usually comprised of an external superstructure that is capable of bearing the load transmitted across the implanted intervertebral disc space. An internal cavity is used to house and contain bone graft or bone graft substitute (collectively referred to as bone graft material) wherein the bone graft material is in contact with a bony surface of each of the vertebral bones that border the implanted disc space (i.e., the vertebral bones above and below the implant disc space). These devices are known in the art, see e.g. U.S. Pat. Nos. RE37,479; 4,820,305; 5,609,637; 5,749,916; 5,865,848; 5,888,224; 5,980,522; 6,071,310; 6,086,613; 6,159,244; 6,176,882; 6,206,922; 6,471,724; 6,582,431; 6,616,695, each of the foregoing being incorporated herein by reference in its entirety.

Given the large number of operative approaches and the substantial anatomical variation between vertebral levels within the same individual or across different individuals, the intervertebral disc implants must be manufactured and provided to the surgeon in a large range of sizes and configurations. This mandates that a large number of different sizes must be made and inventoried—adding to cost for manufacturer, vendor, and end user (hospitals). More importantly, the pre-manufactured devices may provide a suboptimal fit, since the surgeon must choose at the time of implantation from a series of pre-manufactured sizes and configurations that may not fit each and every patient.

SUMMARY

Disclosed herein are, inter alia, placement instruments and methods of use for implantation of spacers within an inter-vertebral disc space. In one embodiment, the load-bearing superstructure of the implant is subdivided and the bone forming material is positioned within an internal space of the placement instrument but external to the load bearing elements themselves. At least a portion of the bone graft material is freely contained within the disc space.

The disclosed exemplary devices and methods may be adapted for use in any known surgical approach to the vertebral column. By way of non-limiting example, the device and method of implantation will be illustrated in a lateral approach to the anterior column of the spinal column.

In another embodiment of this procedure, a lateral tissue corridor is used to position an implant at the lateral border of the vertebral column. The intervertebral disc space that has been targeted for implantation is entered at its lateral border.

The implant is in one embodiment comprised of at least one spacer that is used to bear at least a portion of the load transmitted through the vertebral bodies and across the disc space. The spacer in one variant does not contain a bone graft cavity. The spacer may contain at least one feature adapted to increase fixation to bone, such a bores for screw fixation, an affixed keel and/or rotatable bone fixation member.

In an embodiment, the bone graft material is contained within the placement instrument that is used to deliver the implant to the implantation site. The placement instrument positions the bone graft material in a desired relationship to a spacer(s), wherein the latter is used to bear at least a portion of the vertical load transmitted across the implanted disc space. (The so-called "vertical load" refers to the load that would normally be transmitted across the disc space of a subject standing erectly. It is understood that the vertical load experienced by an individual disc space will vary with the level of that disc space in the vertebral column. In general, more caudal disc space levels will experience higher vertical loads than more cephalad disc space levels.) The spacer(s) and bone graft material are delivered into the disc space in the desired configuration. In another embodiment, the bone graft is positioned outside of one or more spacers that are collectively and concurrently delivered into the disc space by the placement instrument. In this embodiment, no additional bone graft material is enclosed within an internal cavity of any of the spacers.

In yet another embodiment, the bone graft material is positioned within the placement instrument both on the outside of the one or more spacers and also within a internal cavity of at least one spacer. In another embodiment, the bone graft material is positioned within the internal cavity of one or more spacers, but no additional graft material is positioned within the placement instrument and outside of the spacer(s).

After delivery of the implant assembly to the target disc space, the placement instrument is uncoupled from the implant/bone graft material and removed from the body cavity of the subject. The spacer(s) and bone graft material are left within the target disc space. In one embodiment, the implantation procedure is performed through a percutaneous or minimally invasive surgical procedure.

A method of device use is illustrated, wherein the placement device is used to place the implantable spacers at opposing ends of the disc space using a directly lateral surgical approach.

The details of one or more embodiments are set forth in the accompanying drawings and description below. Other features, objects, and advantages will be apparent from the following description, the accompanying drawings and from the claims.

BRIEF DESCRIPTION OF THE DRAWINGS

These and other aspects will now be described in detail with reference to the following drawings. Generally speaking the figures are not to scale in absolute terms or comparatively but are intended to be illustrative. Also, relative placement of features and elements may be modified for the purpose of illustrative clarity.

FIGS. 2A and 2B are a schematic representations of a Functional Spinal Unit (FSU) comprised of two adjunct vertebral bones and an intervening disc space.

FIG. 5 illustrates an assembled embodiment of the present disclosure.

FIG. 6 illustrates section views of the disclosed instrument 130.

FIGS. 7 and 8 are exploded and assembled views of the placement instrument 130 and the attached spacers/implants.

FIGS. 9 and 10 are perspective and orthogonal views of the device assembly.

FIGS. 11 and 11A illustrate the implantable spacers of the present disclosure.

FIGS. 13A, 13B, 14A, and 14B illustrate an exemplary instrument 130 configured to retain implantable spacers 140 at a variable distance relative to the spacer 150.

FIGS. 15, 16, and 17A show a Functional Spinal Unit (FSU) before and after implantation.

FIG. 18 is a cross sectional view of the implanted FSU with the instrument 130 in place.

FIGS. 19A and 19B illustrate the implantable spacers 140 and 150 after removal of the instrument 130.

FIG. 20 illustrates an alternative screw trajectory in the placement of a larger tissue dilator over the tissue dilator of FIG. 19B.

FIGS. 21A and 21B illustrate a change in vertebral alignment in the coronal and/or sagittal planes from placement of implantable spacers of varying sizes.

FIGS. 22A and 22B illustrate the implantable spacers 140 and 150 after removal of the disclosed instrument 130.

FIGS. 23, 24 and 25 illustrate the screw locking member 190 in perspective views and after attachment to the implantable spacer 140.

FIGS. 26 and 27A illustrate the use of a curvilinear embodiment of the present disclosure.

FIG. 29 illustrates an alternative implantable spacer 240.

FIGS. 37A and 37B illustrate an exemplary implantable spacer 350 in an expanded and non-expanded configuration.

FIGS. 39A and 39B illustrate an exemplary screw 170 which is configure to compliment the bore 3508.

FIG. 41A illustrates an exemplary segment 380 coupled to an expanded spacer 350 and a second exemplary segment 380 positioned to be advanced into cavity 3509.

FIG. 41B illustrates an exemplary segment 380,

DETAILED DESCRIPTION

In order to promote an understanding of the principles of the disclosure, reference is made to the drawings and the embodiments illustrated therein. Nevertheless, it will be understood that the drawings are illustrative and no limitation of the scope of the claims is thereby intended. Any such alterations and further modifications in the illustrated embodiments, and any such further applications of the principles of the disclosed devices as illustrated herein are contemplated as would normally occur to one of ordinary skill in the art.

Detailed Description of Exemplary Embodiments

Figure 1:
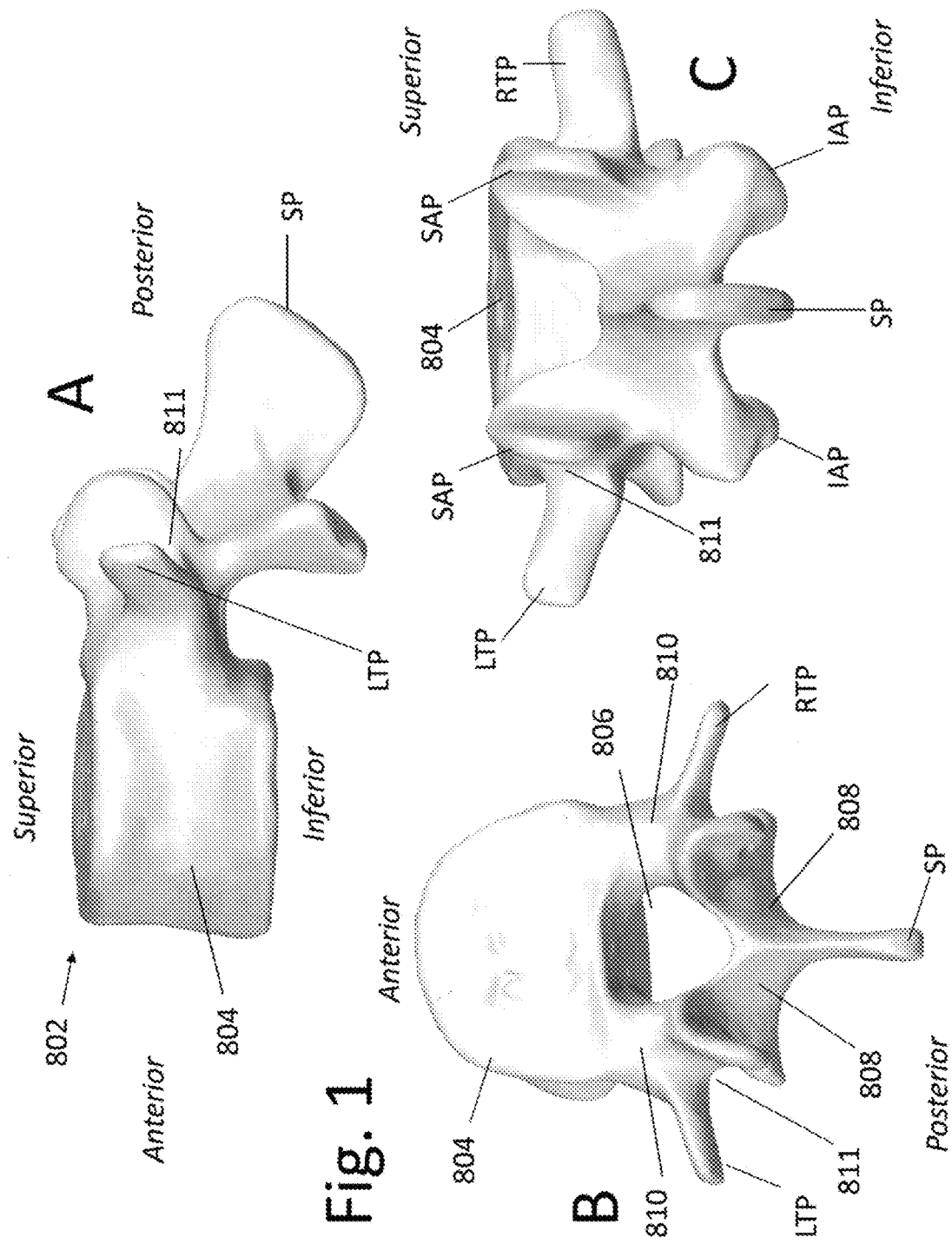
FIG. 1 are a schematic representations of a vertebral bone.

FIG. 1 is a diagrammatic representation of a spinal vertebral bone 802 in multiple views. For clarity of illustration, the vertebral bone of FIG. 1 and those of other illustrations presented in this application are represented schematically, and those skilled in the art will appreciate that actual vertebral bodies may include anatomical details that are not shown in these figures.

Further, it is understood that the vertebral bones at a given level of the spinal column of a human or animal subject will contain anatomical features that may not be present at other levels of the same spinal column. The illustrated vertebral bones are intended to generically represent vertebral bones at any spinal level without limitation. Thus, the disclosed devices and methods may be applied at any applicable spinal level.

Vertebral bone 802 contains an anteriorly-placed vertebral body 804, a centrally placed spinal canal and 806 and posteriorly-placed lamina 808. The pedicle (810) segments of vertebral bone 802 form the lateral aspect of the spinal canal and connect the laminas 808 to the vertebral body 804. The spinal canal contains neural structures such as the spinal cord and/or nerves. A midline protrusion termed the spinous process (SP) extends posteriorly from the medial aspect of laminas 808. A protrusion extends laterally from each side of the posterior aspect of the vertebral bone and is termed the transverse process (TP). A right transverse process (RTP) extends to the right and a left transverse process (LTP) extends to the left. A superior protrusion extends superiorly above the lamina on each side of the vertebral midline and is termed the superior articulating process (SAP). An inferior protrusion extends inferiorly below the lamina on each side of the vertebral midline and is termed the inferior articulating process (IAP). Note that the posterior aspect of the pedicle can be accessed at an indentation 811 in the vertebral bone between the lateral aspect of the SAP and the medial aspect of the transverse process (TP). In surgery, it is common practice to anchor a bone fastener into the pedicle portion of a vertebral bone by inserting the fastener through indentation 811 and into the underlying pedicle.

FIGS. 2A and 2B illustrate a functional spinal unit (FSU), which includes two adjacent vertebrae and the intervertebral disc between them. The intervertebral disc resides between the inferior surface of the upper vertebral body and the superior surface of the lower vertebral body. (Note that a space is shown in FIGS. 2A and 2B where intervertebral disc would reside.) FIG. 2A shows the posterior surface of the adjacent vertebrae and the articulations between them while FIG. 2B shows an oblique view. Note that the FSU contains a three joint complex between the two vertebral bones, with the intervertebral disc comprising the anterior joint. The posterior joints include a facet joint 814 on each side of the midline, wherein the facet joint contains the articulation between the IAP of the superior vertebral bone and the SAP of the inferior bone.

The preceding illustrations and definitions of anatomical structures are known to those of ordinary skill in the art. They are described in more detail in *Atlas of Human Anatomy*, by Frank Netter, third edition, Icon Learning Systems, Teterboro, N.J. The text is hereby incorporated by reference in its entirety.

In one aspect of the present disclosure, instruments and methods that permit a surgeon to position an implant assembly within an intervertebral disc space are provided. In an embodiment, the bone graft material is contained within the placement instrument that is used to deliver the implant to the implantation site. The placement instrument positions the bone graft material in a desired relationship to a spacer (s), wherein the latter is used to bear at least a portion of the vertical load transmitted across the implanted disc space. (The vertical load refers to the load that would normally be transmitted across the disc space of a subject standing erectly. It is understood that the vertical load experienced by an individual disc space will vary with the level of that disc space in the vertebral column. In general, more caudal disc space levels will experience higher vertical loads than more cephalad disc space levels.) The spacer(s) and bone graft material are delivered into the disc space in the desired configuration.

In one embodiment, the bone graft is positioned outside of one or more spacers that are collectively and concurrently delivered into the disc space by the placement instrument. In this embodiment, no additional bone graft material is enclosed within an internal cavity of any of the spacers. In another embodiment, the bone graft material is positioned within the placement instrument both on the outside of the one or more spacers and also within a internal cavity of at least one spacer.

In yet another embodiment, the bone graft material is positioned within the internal cavity of one or more spacers, but no additional graft material is positioned within the placement instrument and outside of the spacer(s).

While the device and the procedure are illustrated using a lateral procedure to position the implant assembly into the disc space of the lumbar spine, it is understood that the device may be used to position a implant assembly into the disc space at any level and using any approach to the spinal column.

Figure 3:
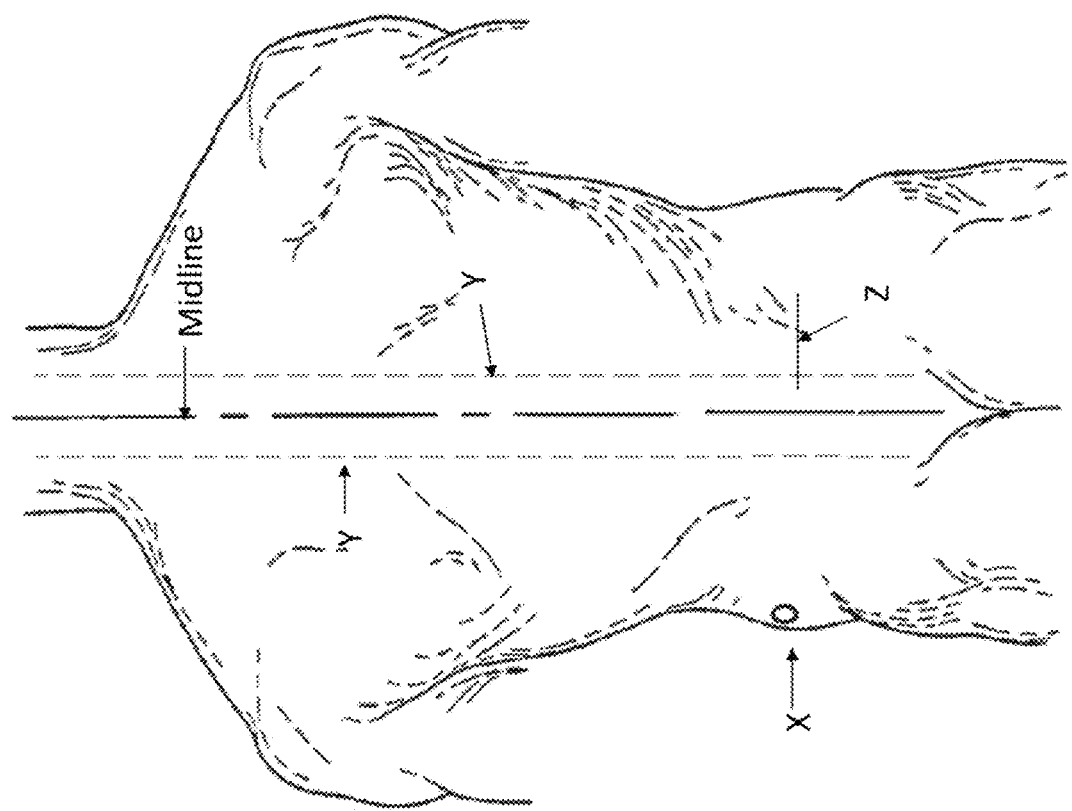
FIG. 3 illustrates the posterior aspect of a subject.

In preparation for percutaneous placement of the implant into a spinal level, the patient can be, but is not necessarily, placed in a prone or lateral decubitus position. The level of the spine that is to be implanted can be localized on X-ray in at least one plane. After the customary sterile preparation of the operative site, the surgeon can localize an incision point on the skin that is substantially directly lateral to the spinal segment that will be implanted. FIG. 3 shows a schematic representation of the posterior aspect of a subject. The skin overlying the back is shown. The midline is labeled and approximates the mid-sagittal plane of the vertebral column. Lines Y show the lateral extent of the transverse processes of the spinal column. Assuming that the spinal level to be accessed is at line Z, the surgeon can make an incision at or about circle X.

Figure 4:
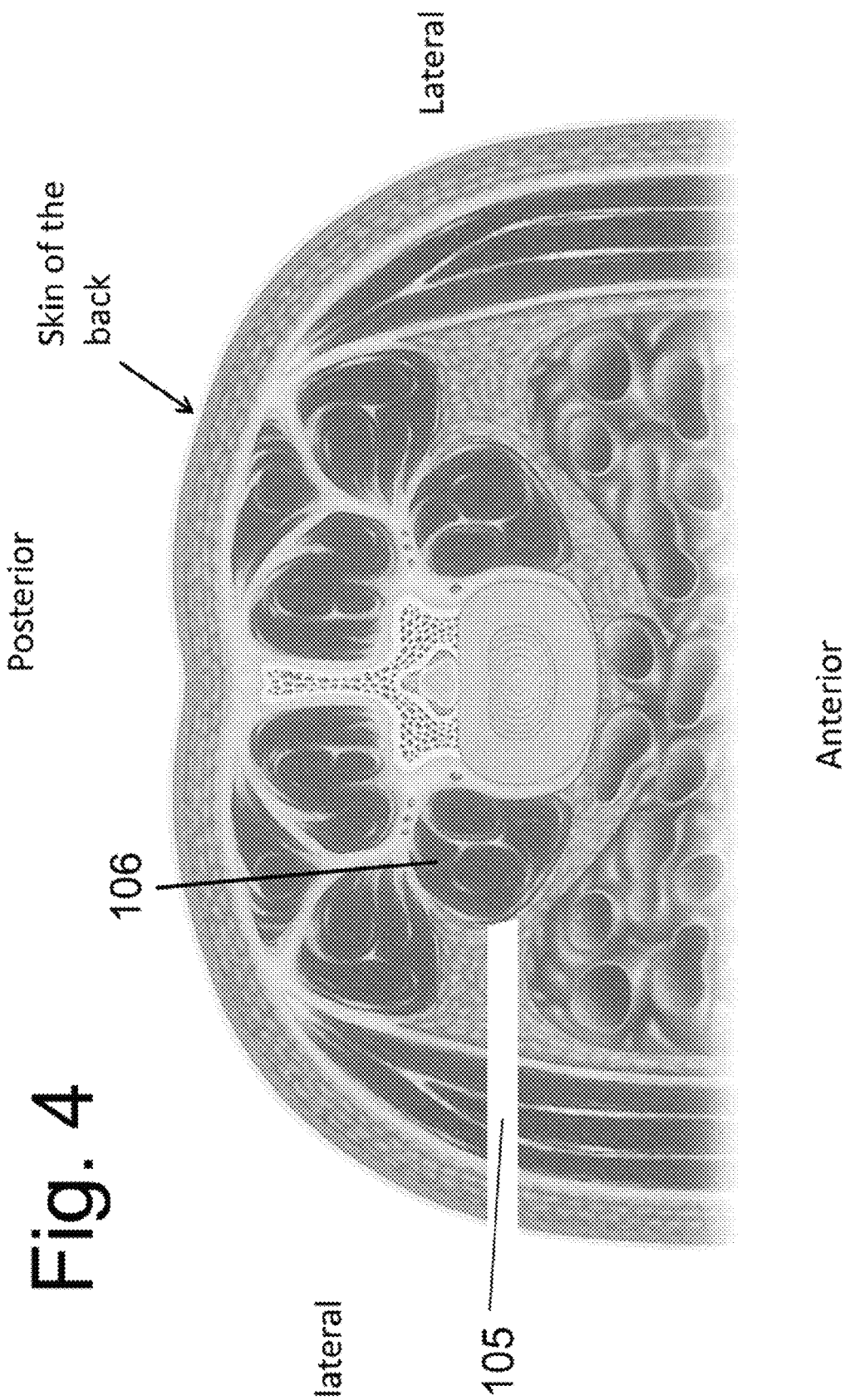
FIG. 4 is a schematic representation of a human torso in cross-section.

FIG. 4 illustrates a cross sectional view of the torso (positioned prone) at the level of the lumbar spine. For clarity of illustration, the contents are represented schematically and those skilled in the art will appreciate that an actual cross section of the human torso may include anatomical details not shown in FIG. 4. A lateral corridor 105 can be made from the flank, through the psoas muscle 106 and onto the lateral aspect of the disc space at the spinal level to be implanted. An implant can be placed through the corridor 105 and into disc space or onto the spine. The procedure is known to those skilled in the art and known by differing names, such as the "XLIF" procedure (see "Extreme Lateral Interbody Fusion (XLIF): a novel surgical technique for anterior lumbar interbody fusion." By Ozgur, Aryan et al. in *Spine J.* 2006 July-August; 6(4):435-43, which is hereby incorporated by reference in its entirety.) Variations of the operation are also known as Direct Lateral Interbody Fusion (DLIF) and the like.

An instrument (not shown) is passed through corridor 105 and onto the lateral aspect of the psoas muscle 106. The instrument is advanced through the muscle and into the disc space. Since important nerve structures may transverse the psoas muscle, the instrument (and/or a probe or device placed through a channel of the instrument) is connected to an Electromyography (EMG) apparatus (or any other electrical system that is used to localize nerve tissue), and used, at least partially, as an EMG probe during advancement through the muscle. In this way, the advancement of the instrument through the psoas muscle is performed under EMG guidance. Under X-ray visualization, the instrument is placed into the disc space. At least a portion of the disc material is removed from within the disc space through the established corridor. After the discectomy is performed and the bony end plates have been decorticated and prepared, at least one spacer and bone graft material (and/or bone graft substitute) is placed within the evacuated portion of the disc space. With time, the graft material will form a bony bridge between the two vertebral bodies and fuse them. As described, the procedure is performed in a percutaneous manner and under x-ray. A wider incision may be employed and portions of the procedure, such as the discectomy, may be performed under direct vision and using minimally invasive surgical technique.

Instrument 130 is used to position at least one spacer into the partially evacuated disc space. (The implantation is preferably, but not necessarily, performed in a percutaneous manner.) The implanted spacer functions to bear at least a portion of the load transmitted through the disc space. Instrument 130 also places the bone graft or bone graft substitute (collectively called bone graft material) into the disc space. The bone graft material is delivered in prescribed spatial relationship to the spacer(s). In the illustrated embodiment, the spacer(s) will not contain an internal cavity configured to house a bone graft material. However, it is understood that one or more of the implanted spacers may alternatively comprise an internal cavity configured to house bone graft material, wherein the house bone graft material is in communication with each of the vertebral bones that border the implanted disc space.

An embodiment of instrument 130 is shown in FIGS. 5 and 6. Instrument 130 has handle 1302, side members 1304 and an indentation 1305 at one end of each side member 1304. Surface 1306 is positioned between side members 1304. A bore 1308 transverses handle 1302.

Figure 10:
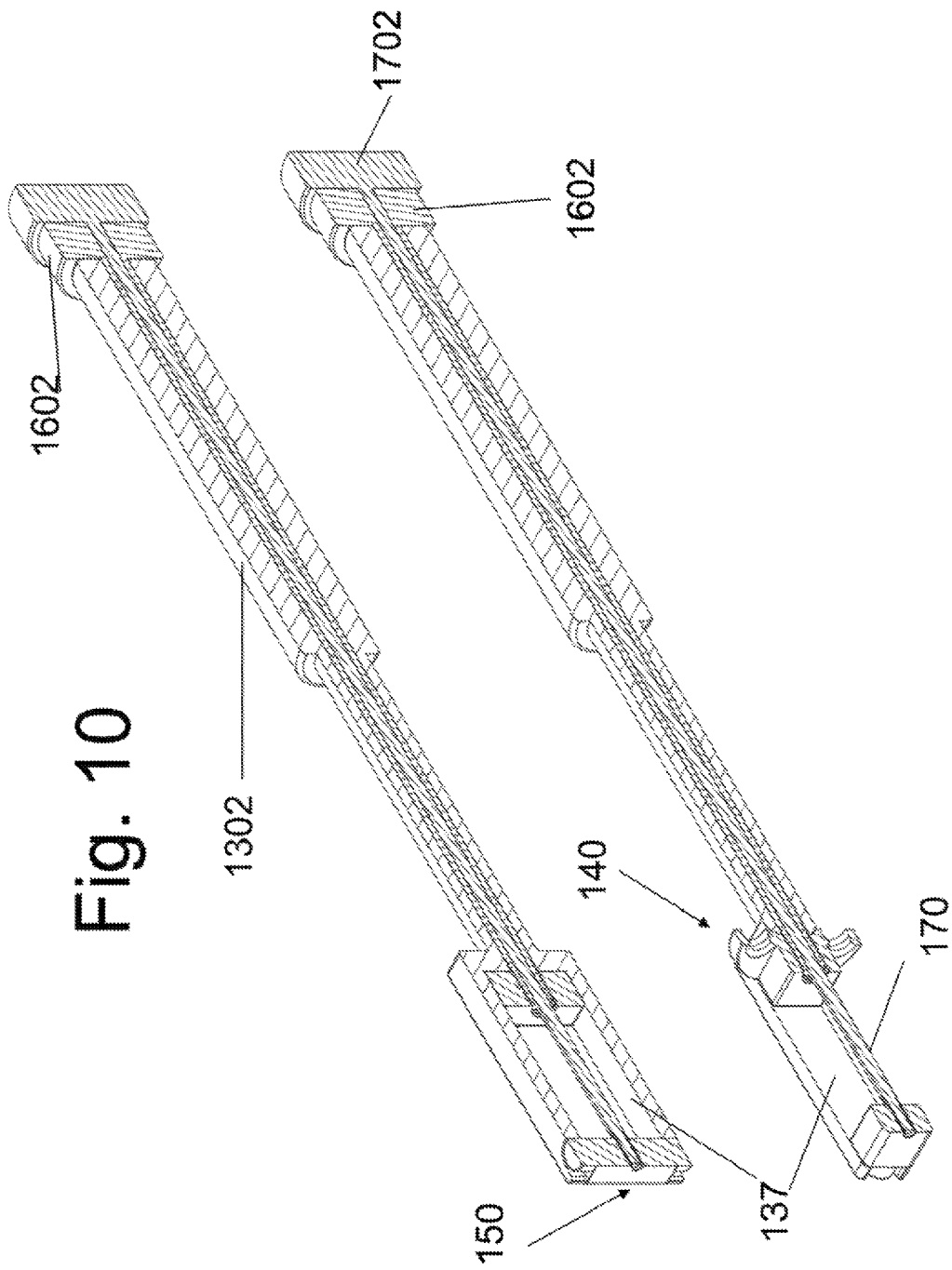
Figure 12:
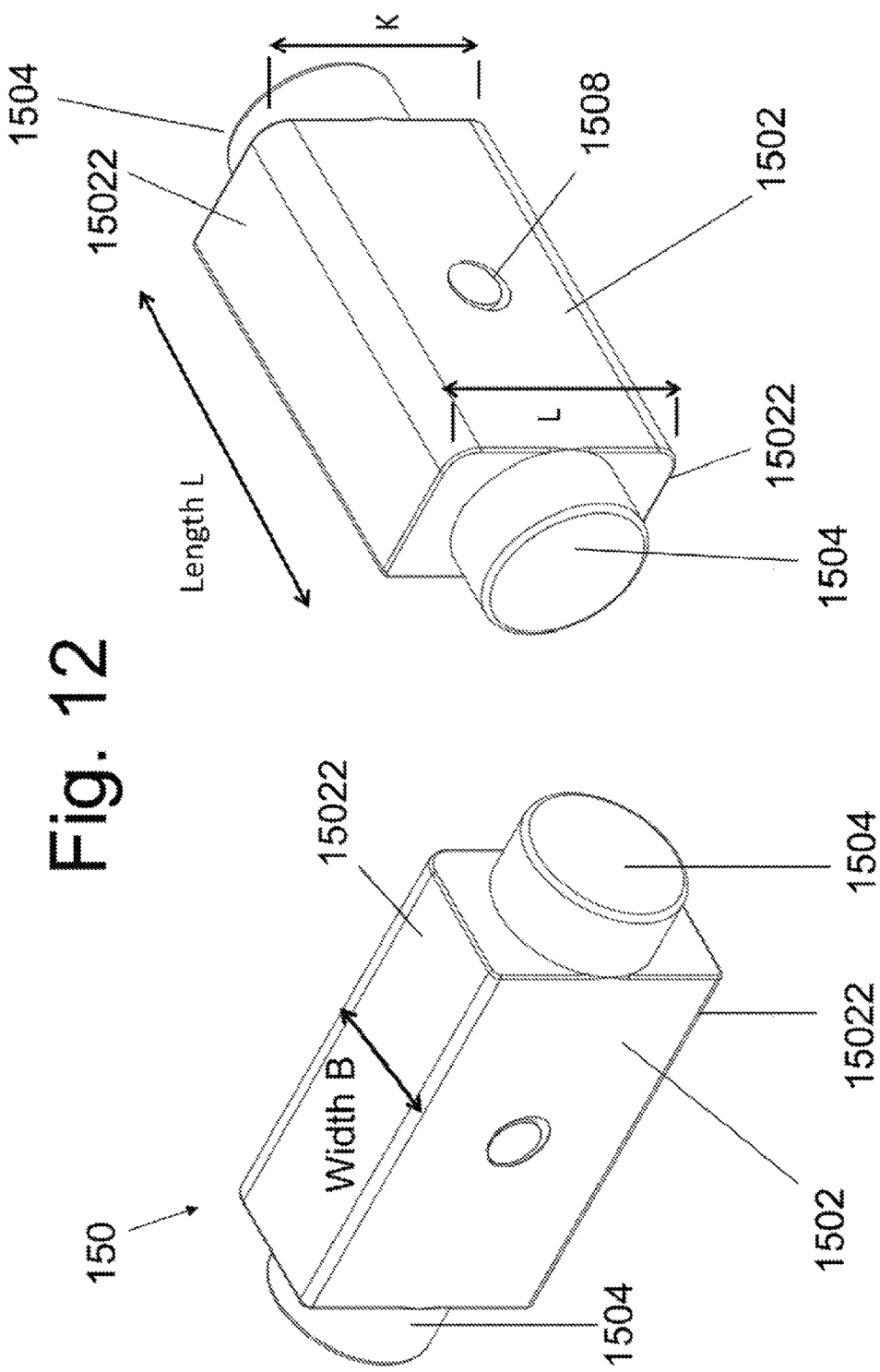
FIG. 12 illustrates views of the implantable spacer 150.

FIG. 7 shows instrument 130 and two spacer implants in the disassembled state while FIG. 8 shows the assembled device. Spacers (alternatively labeled "implant") 140 and 150 are attached to instrument 130 using screws 160 and 170, respectively. The assembly is shown in three planes in FIG. 9. Sectional views are shown in FIG. 10. Spacer 140 is shown in FIG. 11 while spacer 150 is illustrated in FIG. 12. Preferably, but not necessarily, each spacer does not have a medial to lateral dimension that is greater than one half of the medial to lateral dimension of the implanted disc space. That is, each of width A of spacer 140 (FIG. 11A) and width B of spacer 150 (FIG. 12) is less than on half of the value of the width W of the implanted disc space (the width of the disc space is the maximum disc space dimension in the coronal plane of the spine—as shown in FIG. 21B).

Implantable spacer 140 has central body 1402 that is inserted into the disc space and maintains the distance between the adjacent bodies and the height of the disc space. Body 1402 may be comprised of any material that is adapted for biological implantation, including a segment of bone (allograft or autograft that is harvested and shaped at the same operation) that is affixed onto a side plate member (as shown in FIG. 11A). In one variant, the upper and/or lower surfaces 14022 of body 1402 contain surface protrusions or textures (not shown) that increase fixation of these surfaces onto the abutting bone.

A side member 1404 is adapted to be positioned onto the side of each of the vertebral bodies. At least one bore 1406 is positioned within at least one side member 1404 and permits placement of bone screw into the side of at least one vertebral body. The surface (14042) that abuts the side surface of the vertebral bone may have one or more protrusions (not shown), such as, for example, spike, that penetrate and fixate into said bone. Spikes adapted for bone fixation are well known in the art and are shown in US 2004/0162558 and others. (The citation is hereby incorporated by reference in its entirety). A curvilinear surface 1407 permits interaction of the spacer 140 with curvilinear surface 1306 of instrument 130. A threaded bore hole 1409 is contained within central body 1402 of spacer 140 and, in assembly with instrument 130, accepts the threaded end of screw 160.

While each of end height K and end height L of body 1402 (FIG. 11) is shown as being of equal length, it is contemplated that each of heights K and L may alternatively be different. In this may, the implant may be used, for example to impart a greater height to the anterior disc space than the posterior disc space and impart a lordotic curvature onto the implanted FSU segment (FIG. 21A—in sagittal view). It is further contemplated that spacer 140 may be alternatively comprised of a substantially solid member (for example, a rectangular or trapezoid member that is similar to body 1402) without any side members 1404 that extend onto the side of vertebral bones.

Implantable spacer 150 has central body 1502 that is inserted into the disc space and maintains the distance between the adjacent bodies and the height of the disc space. Body 1502 may be comprised of any material that is adapted for biological implantation, including being at least partially comprised of a segment of bone (whether allograft or autograft). The upper and/or lower surfaces 15022 of body 1502 may contain surface protrusions or textures (not shown) that increase fixation of these surfaces onto the abutting bone. At least one side member 1504 is adapted to interact with indentation 1305 at one end of each side member 1304 of instrument 130. A threaded bore hole 1508 is contained within central body 1502 of spacer 150 and, in assembly with instrument 130, accepts the threaded end of screw 170.

While each of end height K and end height L of body 1502 (FIG. 12) is shown as being of equal length, it is contemplated that each of heights K and L may alternatively be different. In this way, the implant may be used, for example to impart a greater height to the anterior disc space than the posterior disc space and impart a lordotic curvature onto the implanted FSU segment (FIG. 21A—in sagittal view). Further, the heights of bodies 1402 and 1502 may be different so as to change the vertebral alignment in the coronal plane of the spine—such as, for example, in scoliosis. The latter is illustrated in FIG. 21B illustrates a coronal plane section of the vertebral bones that surround an implanted disc space. Note the coronal plane curvature created by the different sized implants 140 and 150.

Figure 14A:
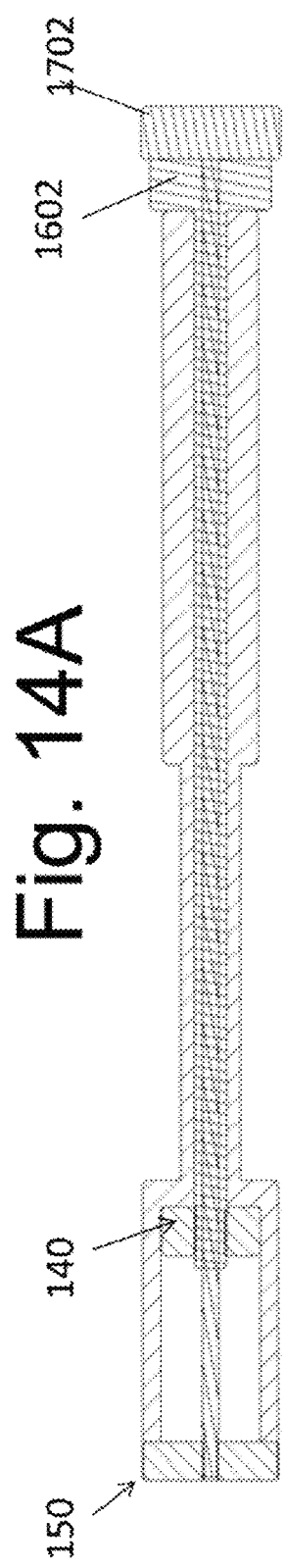
Figure 14B:
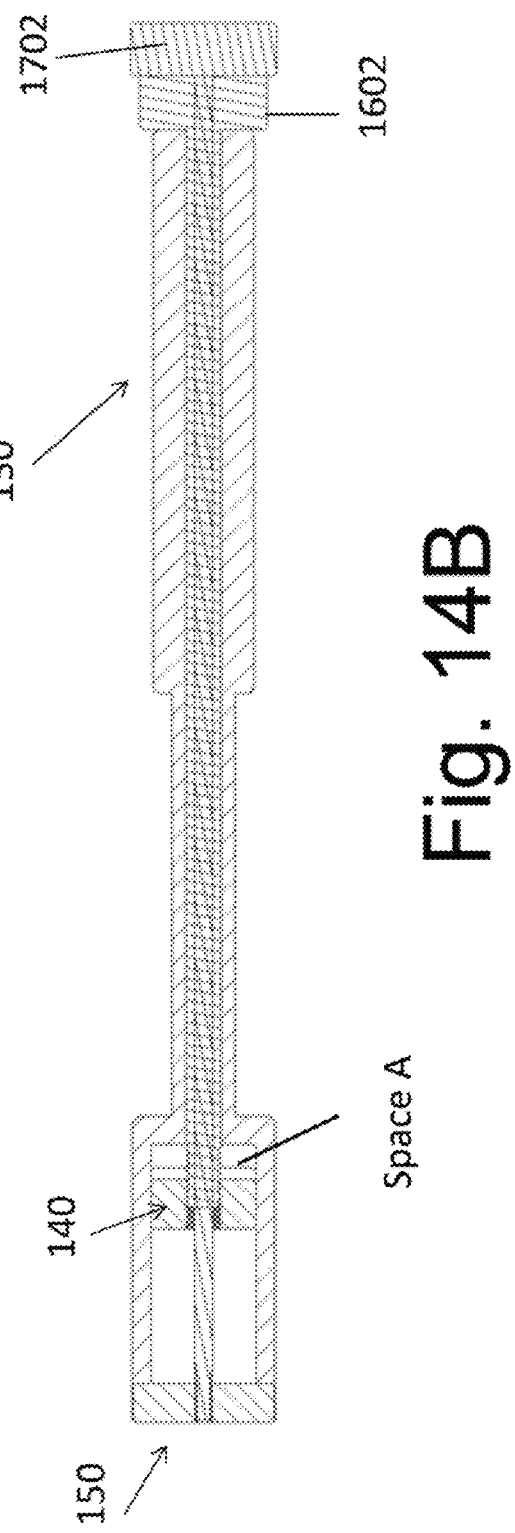

FIGS. 13 and 14 illustrate how instrument 130 may be used to position implants 140 and 150 into the target disc space with a variable distance between them. FIGS. 9, 10, 13A and 14A illustrate implant 140 attached to screw 160 and threadedly attached with surface 1407 abutting surface 1306 of instrument 130. Note that the end segment 1602 of screw 160 is positioned between the end of instrument 130 and end 1702 of screw 170. With rotation of end 1602 in a first direction, implant 140 will be displaced towards implant 150 by the threads of screw 160. With rotation of end 1602 in an opposite direction, implant 140 will be moved away from implant 150 until surface 1407 abuts surface 1306 of instrument 130. In this way, instrument 130 may be used to position implants 140 and 150 into the target disc space with a variable distance between them. FIGS. 13B and 14B illustrate implant 140 having been displaced towards implant 150. Note that space A is now positioned between implant 140 and surface 1306 on instrument 130.

Method of Use

Patient positioning, incision placement, the surgical corridor used, and traversal of the psoas muscle (including under electrophysiological monitoring (EMG) and the like) were described above and will not be repeated herein.

Figure 16:
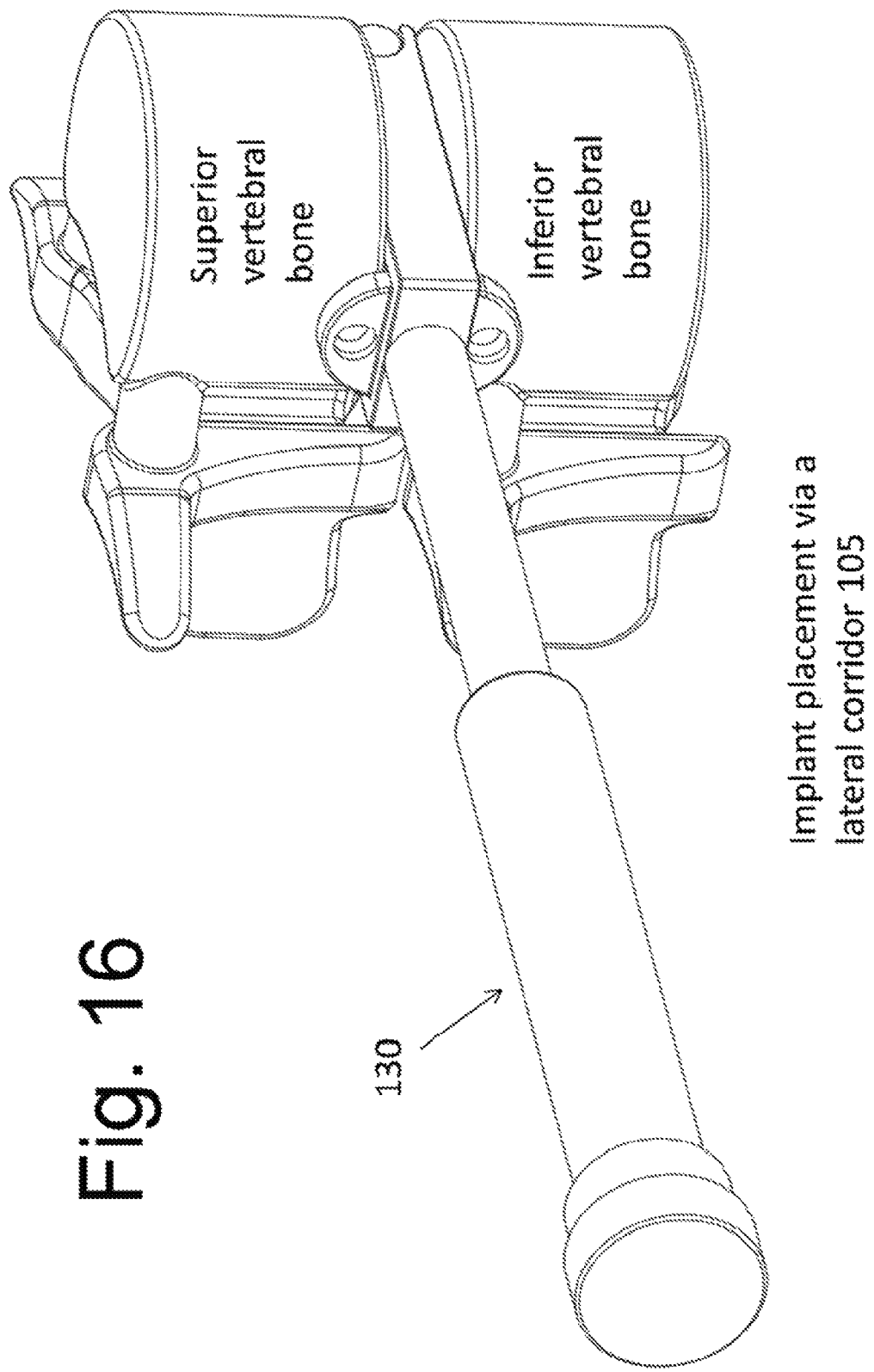

FIG. 15 shows a diagrammatic representation of two vertebral bodies and an intervening disc space in multiple views. For clarity of illustration, the vertebral bodies are represented schematically and those skilled in the art will appreciate that actual vertebral bodies include anatomical details not shown in FIG. 15. As mentioned, at least a partial removal of the disc material is performed before implantation of the spacers 140 and 150 and bone graft material between them. The area of disc space that is evacuated of disc material may be slightly larger than the distance between the outer surfaces of side members 1304 of instrument 130. FIG. 16 illustrates the assembly of FIG. 9 (comprised of instrument 130, spacer 140, spacer 150, screw 160 and screw 170) inserted into the disc space between two vertebral bodies using a lateral approach (corridor 105, FIG. 4). Before insertion, a bone graft material is placed within cavity 137 that is contained between side members 1304, spacer 140, and spacer 150 in the assembled device. The bone graft material is at least partially delivered into the disc space while in cavity 137. In one embodiment, the bone graft material is contained with a cavity of those members that will be left implanted in the disc space. The graft material is contained in a cavity of the placement instrument and the instrument, upon removal from the disc space, leaves the graft material freely positioned within the disc space and in between spacer 140 and 150 (see FIGS. 19A and B). That is, in one embodiment, the bone graft material is not contained within an internal cavity of the implanted spacers themselves. FIG. 17A illustrates the insertion in multiple orthogonal planes.

In one exemplary embodiment, the width of the disc space is first measured. The width of the disc space, W (FIG. 22B), is equal to the greatest distance from a lateral side surface to an opposing lateral side surface of the target disc space when measured in a coronal plane of the disc space. The placement instrument is the selected so that the lateral length, L (FIGS. 6 and 9), from surface 1306 to the end is substantially equal to the width, W, of the disc space. In this way, when spacers 140 and 150 are affixed to the instrument 130, the total distance from the outside surface of spacer 140 to the outside surface of spacer 150 is substantially equal to the width, W, of the disc space. It is appreciated that in one embodiment the length L is at least equal to the width W. in another embodiment, the length L is slightly greater than the width W, in order to enable the device to allows for some accommodation of length—as is shown in FIGS. 14B and 28 through 32.

Figure 17B:
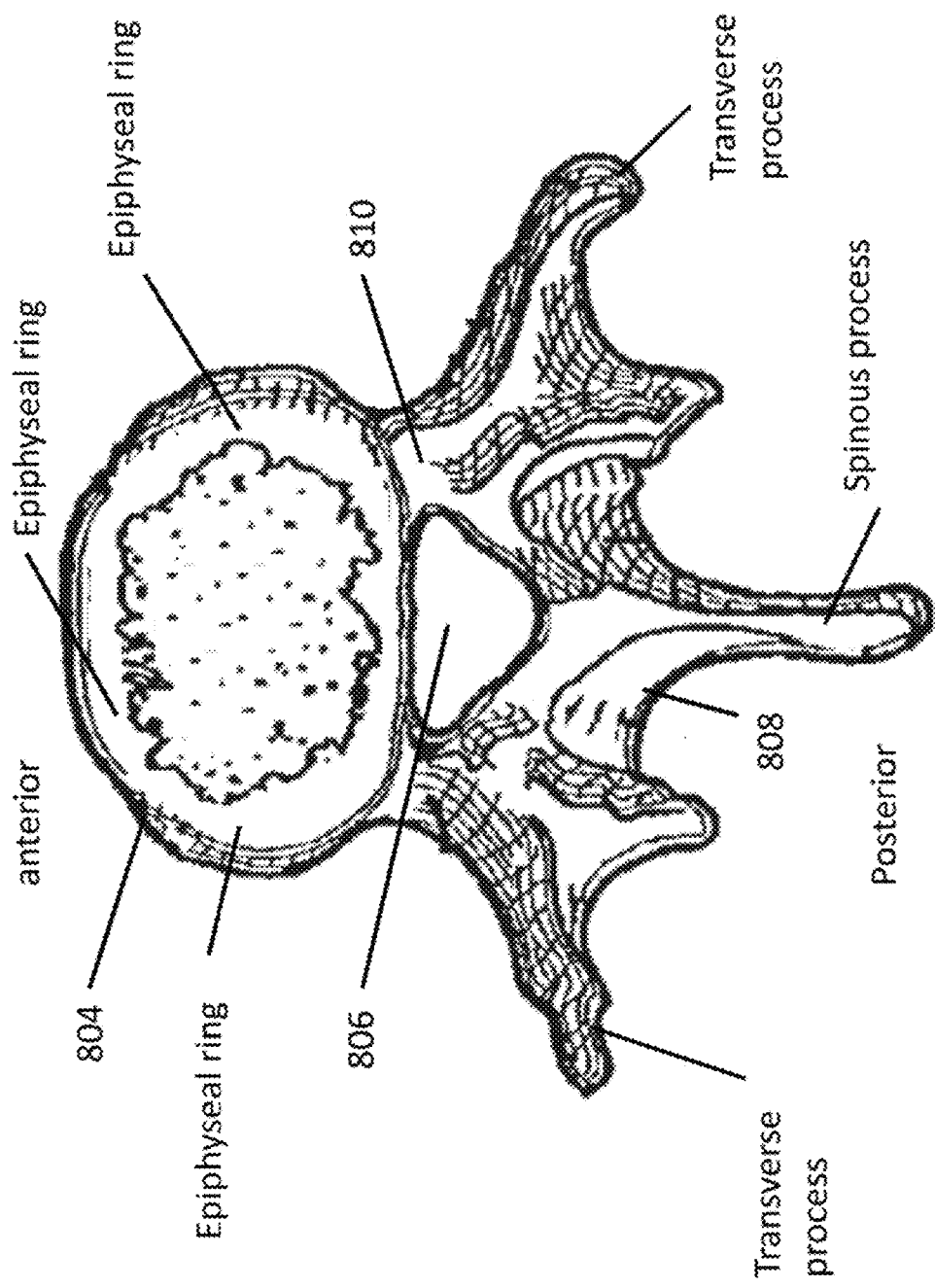
FIG. 17B illustrates a top surface of a vertebral bone and the epiphyseal ring.

Note that at least a segment of each of spacers 140 and 150 may be positioned overlying the epiphyseal ring of the vertebral bones immediately superior and inferior (i.e., that border) the implanted disc space. The epiphyseal ring is illustrated in FIG. 17B, wherein an view of the superior aspect of a vertebral bone is shown (the numbers are as shown in FIG. 1). The epiphyseal ring forms the strongest portion of the superior and inferior surfaces of the vertebral body, which are the vertebral surfaces that border the intervertebral disc spaces. (The epiphyseal ring is more fully discussed in: *The epiphyseal ring: a long forgotten anatomical structure with significant physiological function*. Dar G, et al. Spine. 2011 May 15; 36(11):850-6. The article is hereby incorporated by reference in its entirety).

A cross sectional view (in the coronal plane of the spine) is shown in FIG. 17B. Note that members 1406 abut the lateral aspect of the vertebral bodies. Each of spacers 140 and 150 are on opposing sides of the disc space. Cavity 137 is packed with bone graft material and rests between the two spacers 140 and 150, wherein, in one embodiment, the bone graft material is not contained within a spacer cavity. (It is also contemplated that, in an embodiment, at least one of spacers 140 and 150 may contain a cavity for bone graft material—in addition to the bone graft material contained between then in cavity 137.)

Bone screws 152 are placed through bore holes 1406 and into the underlying bone. Screws 170 and 160 are unthreaded and removed. Instrument 130 is then removed, leaving the bone graft material within the evacuated disc space. FIGS. 19A and 19B illustrate the implanted spacer (the bone graft material resides between the spacers). In an alternative screw trajectory, shown in FIG. 20, the bone screws are aimed so that the distal aspect of at least one bone screw is aimed towards the disc space. In an embodiment, the distal end of at least one screw is anchored into spacer 150. (Note that bores 1406 of implantable spacer 140 permit placement of the bone screws in the trajectory of FIG. 19B or 20. That is, the same device embodiment permits variable trajectory.)

Figure 24:
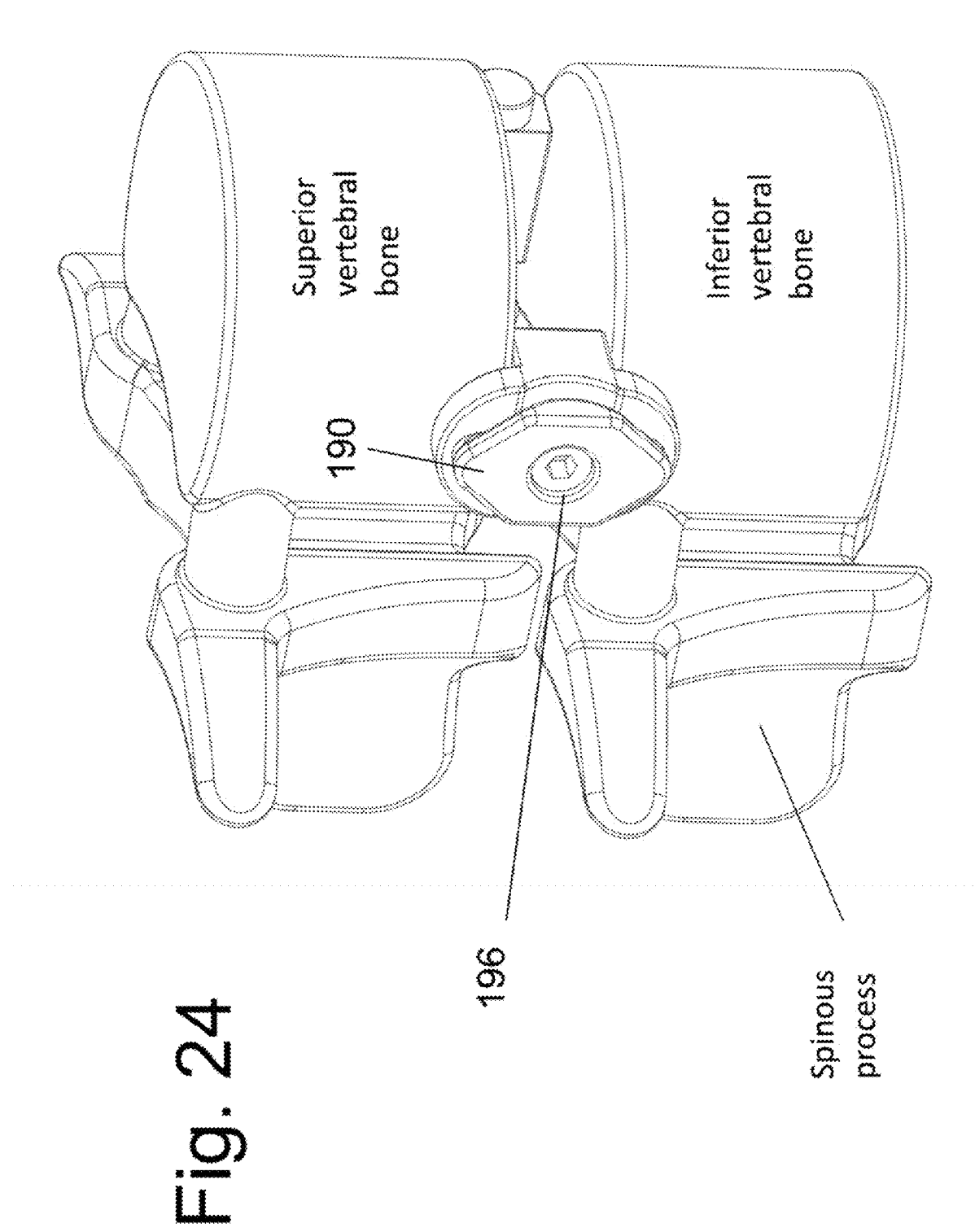
Figure 25:
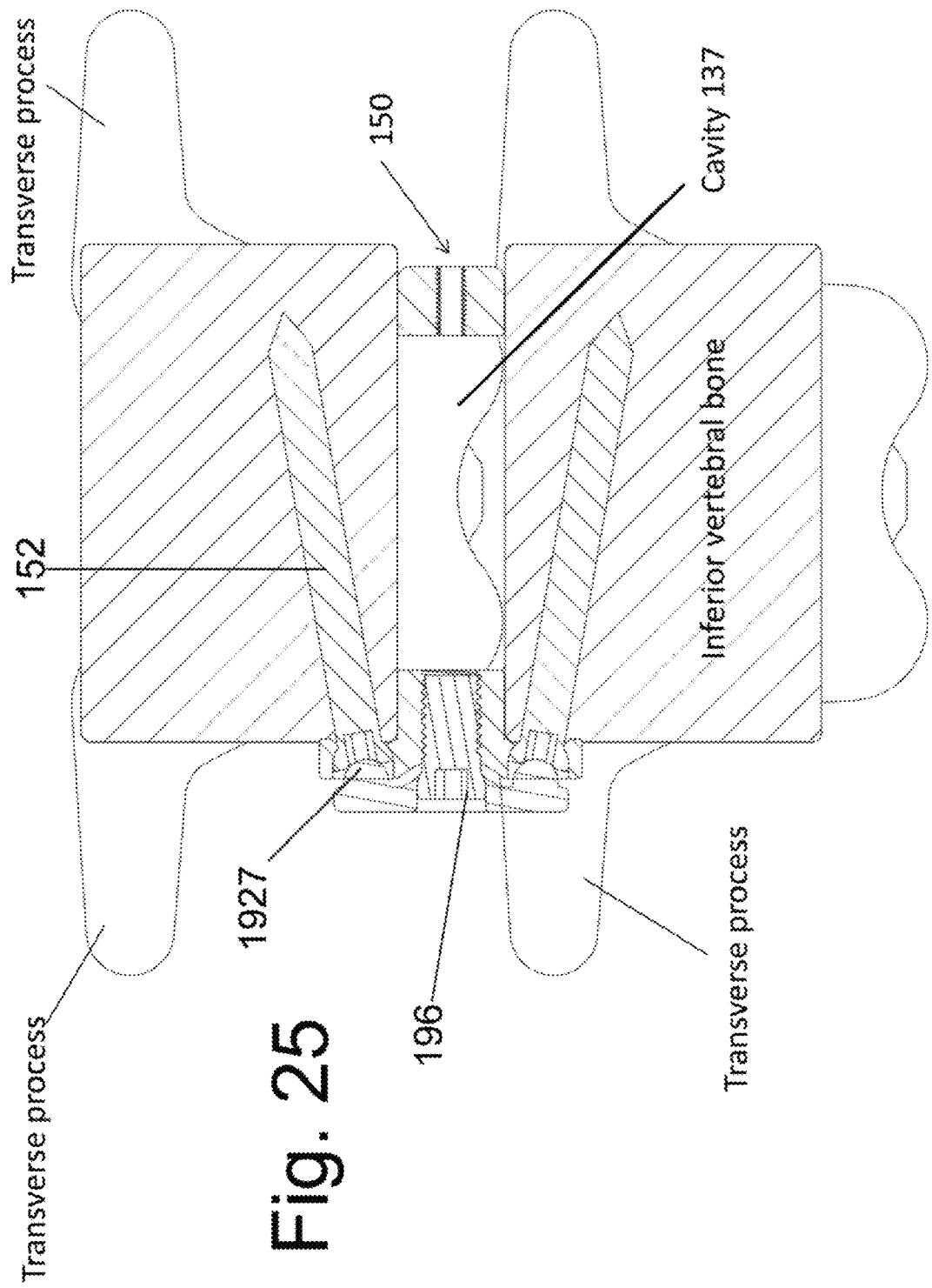

Preferably, but not necessarily, a device member and/or feature may be added to lock the bone screws to spacer 140. Plate-to-screw locking features are well known in the art and any applicable such feature/device may be used here. An illustrative example embodiment is shown in FIG. 23. Locking plate 190 has a first surface 192 with curvilinear central protrusion 1922 that is adapted to face (but not contact) surface 1407 of spacer 140. A non-threaded bore hole 1924 is adapted to accept a locking screw 196. When seated, the threaded end of screw 196 interacts with complimentary threads of bore 1409 of spacer 140. At least one additional protrusion 1927 extends from surface 192. In use, protrusion 1927 is adapted to forcefully abut the (head) portion of a bone screw 152 that reside within bore hole 1406. In this way, advancement of locking screw 196 into threaded hole 1409 provides a force that drives protrusion 1927 into bone screw 152 and immobilizes the bone screw relative spacer 140. The implanted locking plate 190 and locking screw 196 are shown in FIG. 24. A sectional view with locking plate 190 in the deployed position is shown in FIG. 25. Note that the locking mechanism locks both the screw above and the screw bellow the implanted disc space.

Figure 26:
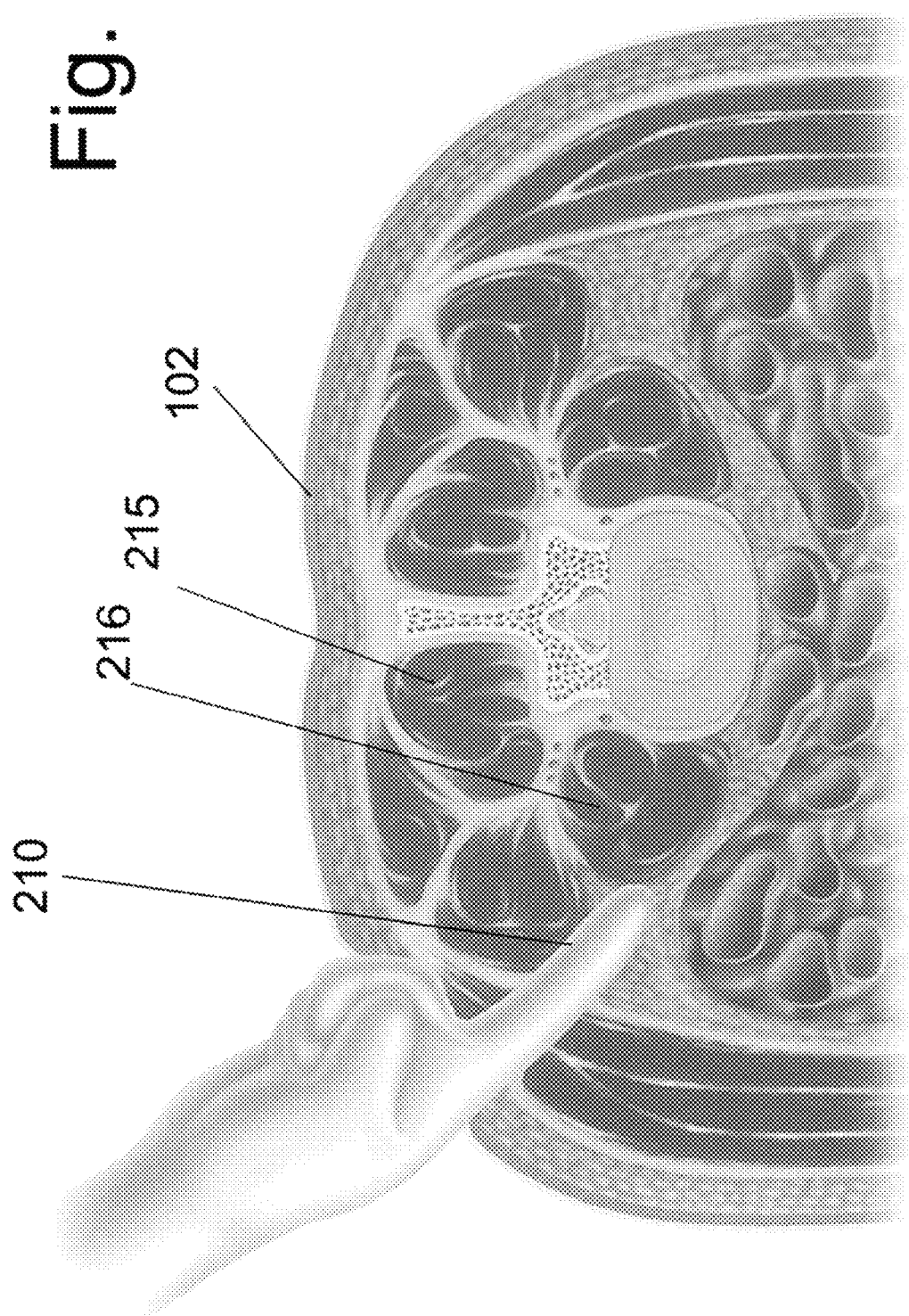

While use of instrument 130 and attached spacers has been illustrated in a straight lateral approach to the intervertebral disc space, the devices may be used in an anterior, posterior, oblique or any other known approach to the disc space. Further, the device may be easily configured for use in a curvilinear approach to the disc space. An illustrative example of a curvilinear approach to the disc space is shown in FIG. 26. In preparation for percutaneous placement of an orthopedic implant into a spinal disc space, the patient is placed in the prone position with spine and skin 102 in the superior position. The level of the spine that is to be implanted is localized on X-ray in at least one plane. After the customary sterile preparation of the operative site, the surgeon localizes an incision point that is lateral to the paraspinal muscles (the erector spinae muscle group 215 and/or others, for example) but not directly lateral to the side of the disc space. At least one finger 210 may be placed into the retro-peritoneal space and the lateral aspect of the psoas muscle 216 is palpated, as shown in FIG. 26. Alternatively, the surgeon can identify the psoas muscle by inserting an instrument instead of using direct digital palpation.

Figure 27B:
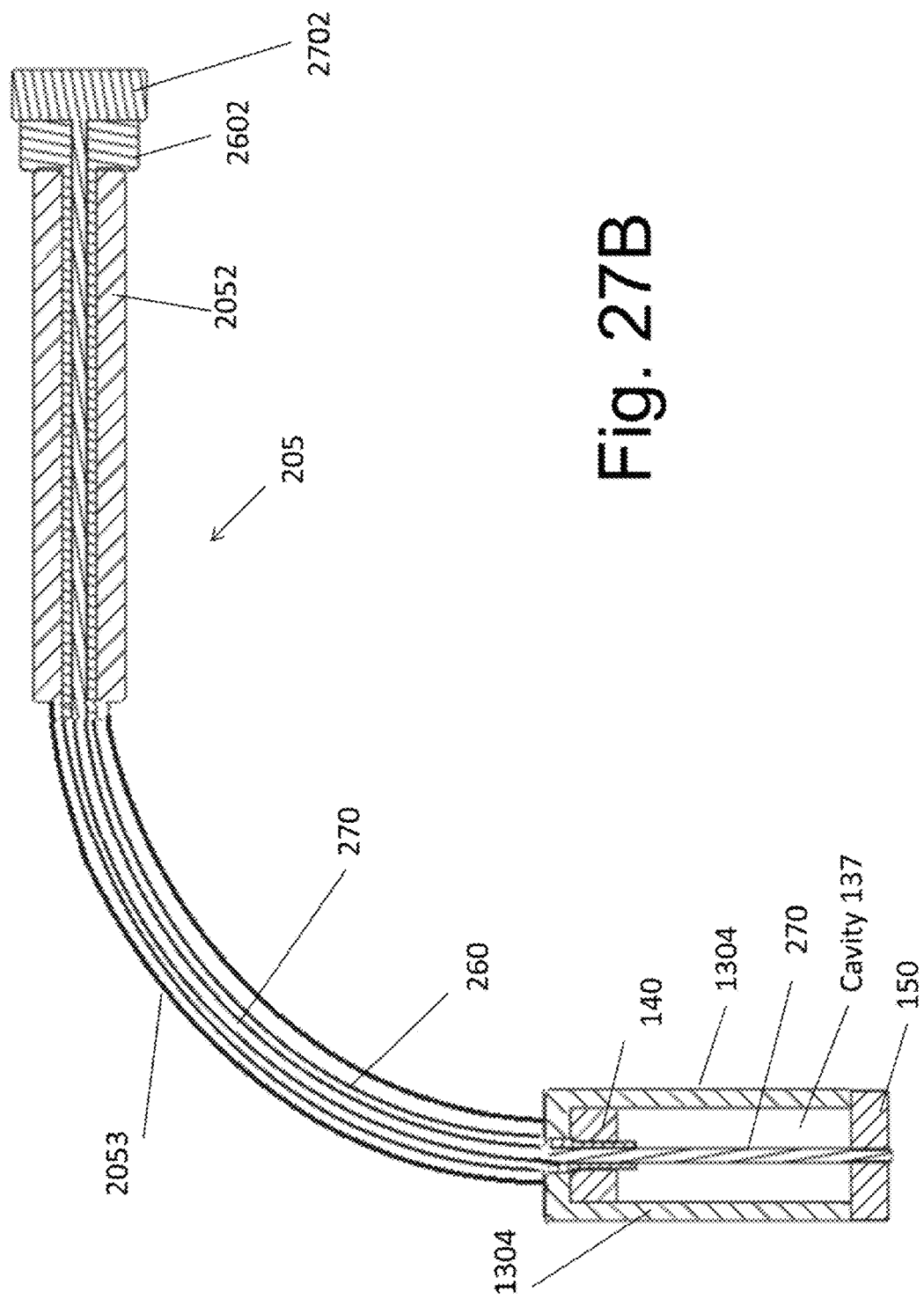
FIG. 27B illustrates a cross section view of the curvilinear embodiment.

A curvilinear instrument 205 is shown in FIG. 27A. Instrument 205 is similar to instrument 130 but contains a curvilinear connection 2053 between the handle 2052 and the end segment that attaches the implants (the end segment contains side members 2054). As in the prior embodiment of FIGS. 9 and 10, member 260 affixes implant 140 to the instrument 205, whereas member 270 affixes implant 150 to the instrument 205. Member 260 has a first end 2602, an opposing threaded end and is at least partially malleable there between. Similarly member 270 has a first end 2702, an opposing threaded end and is at least partially malleable there between. As shown in the section view of FIG. 27b, members 260 and 270 are malleably configured to be positioned within the substantially linear portion of handle 2302 and also within the substantially non-linear portions of connection 2303.

FIGS. 13 and 14 illustrated how instrument 130 can retain each of spacers 140 and 150 at a variable distance from one another. FIGS. 28 to 32 illustrate a device embodiment wherein the distance between each of implants 140 and 150 is displayed by the instrument. That is, the current embodiment differs from the prior embodiment in that contains an indicator of distance between implant 140 and 150. Whereas the distance between the implants 140 and 150 of the prior was determined by measuring that distance with a separate measuring device (ruler, caliper, and the like), the current embodiment contains a distance indicator.

Figure 28:
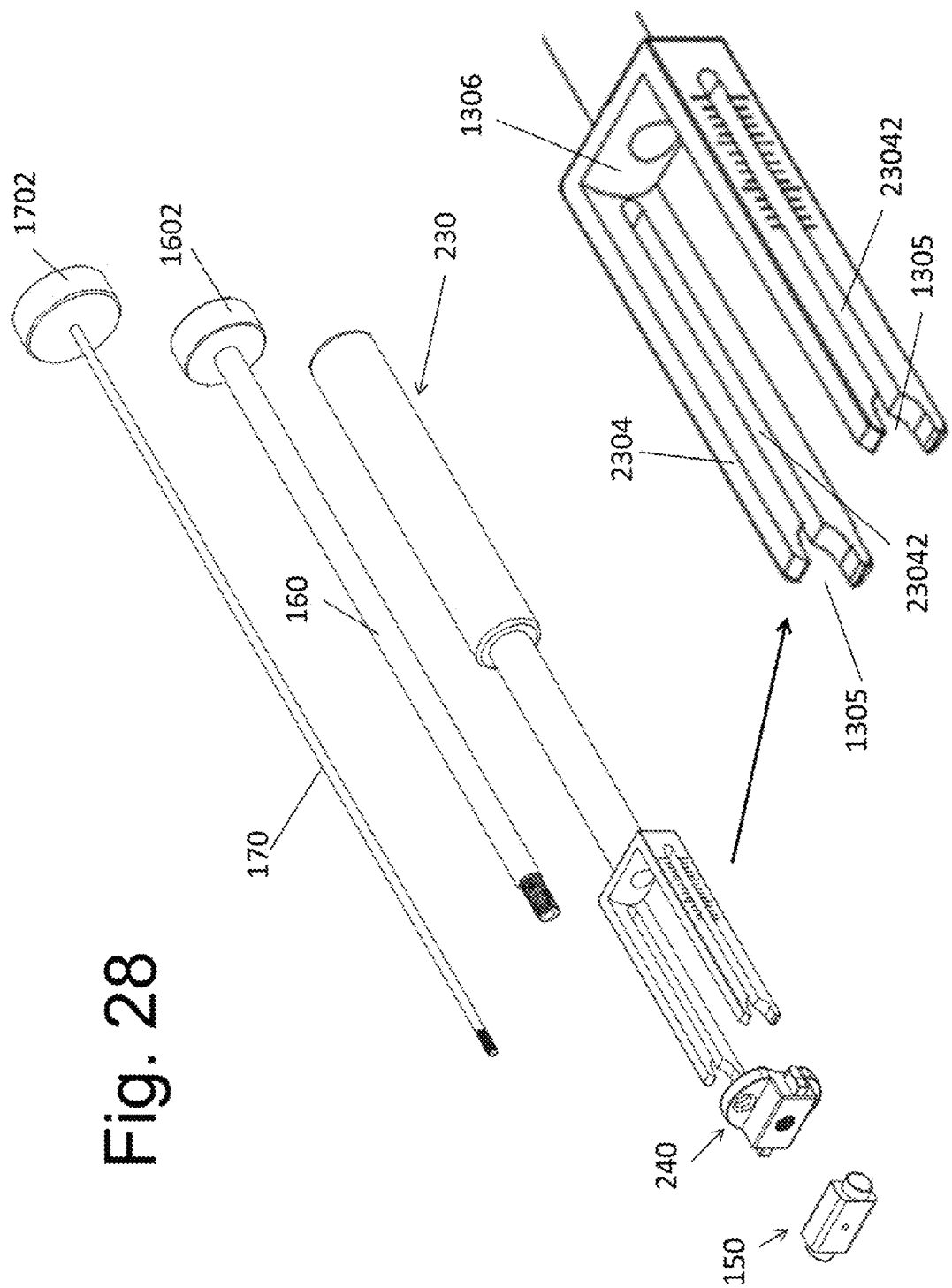
FIG. 28 illustrates an exploded view of an alternative device embodiment, wherein a placement instrument 230 is used.

FIG. 28 illustrates an exploded view of the current embodiment. The exploded view is similar to that of FIG. 7. Member 150, 170 and 160 are unchanged. Instrument 130 is replaced by instrument 230, wherein side members 2304 differ from side member 1304 in that each member 2304 contains a full thickness channel 23042 that extends proximally towards curvilinear surface 1306 from end indentation 1305. (A magnification of the end segment on instrument 230 is also shown in FIG. 28.) Markings are displayed on the outer side surface of each member 2304, from which the distance between implant 140 and 150 may be ascertained. While the markings are shown as "hatch marks" in the illustrations, it is understood that numbers, letters or any other notation may be used to indicate the distance of the marking from implant 150. The notations may express distance in a known unit of measure or they may use an arbitrary scale that is disclosed to the user in the instrument's instruction manual.

Implant 240 is illustrated in FIG. 29. Because it's substantially similar to implant 140 (FIG. 11), the same numbering scheme is used to illustrate it. It differs from implant 140 in having a side protrusion 242 on each side of the implant. Each protrusion 242 is sized and shaped to slidably move in one of each channel 23042 of instrument 230. A marking 2424 is found on the outer side surface of protrusion 242 and functions as a pointer that displays implant 242's position relative to the markings on the side surface side member 2304 of instrument 230. In this way, marking 2424 can be used to directly read the distance between implant 150 and 240.

Figure 30:
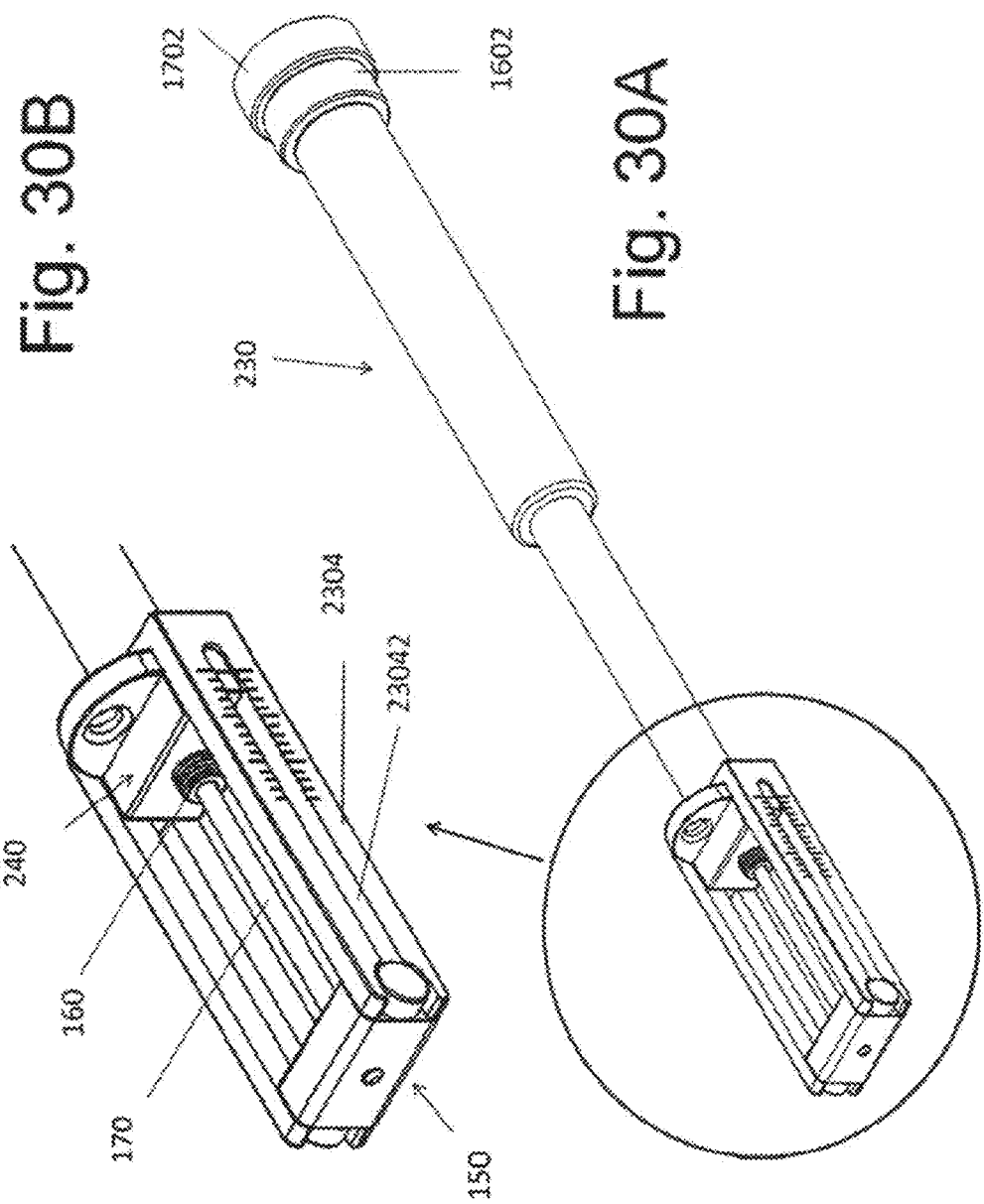
FIGS. 30A and 30B illustrate the assembly comprising the instrument 230 and the implantable spacer 240.
Figure 31:
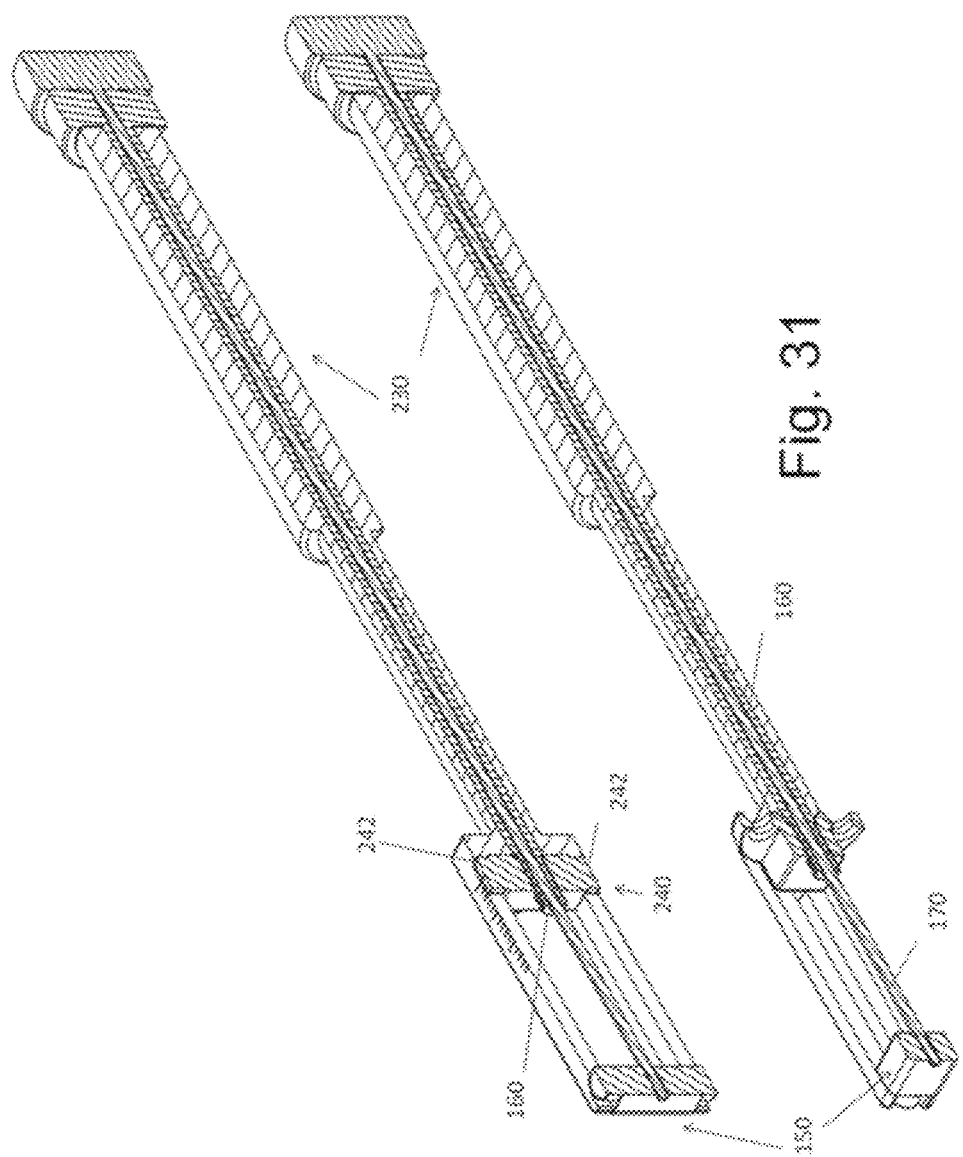
FIG. 31 illustrates sectional views of the assembly of FIG. 29.
Figure 32:
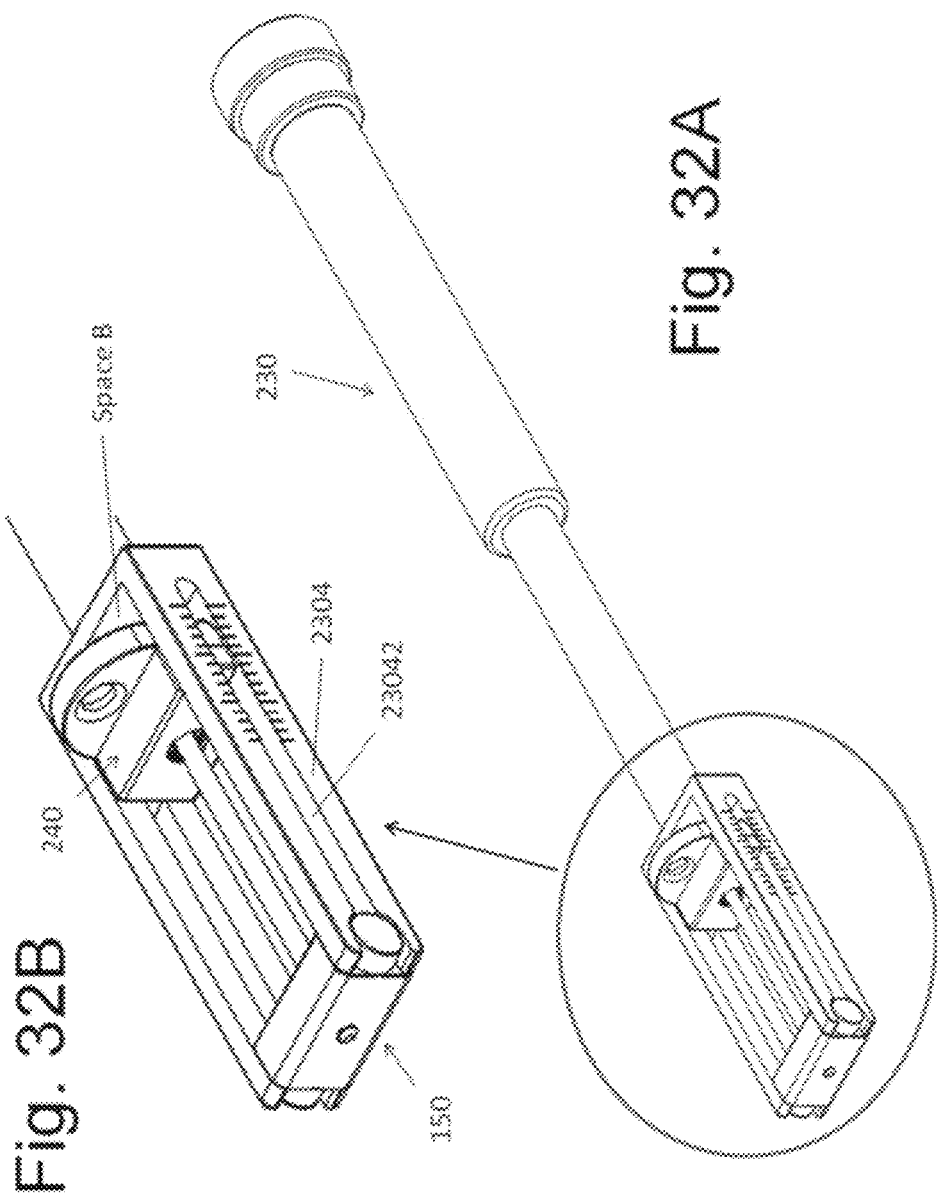
FIGS. 32A and 32B illustrate an exemplary instrument 230 configured to retain the implantable spacers 240 at a variable distance relative to the spacer 150; the distance between the implantable spacers can be read directly from the instrument 230.

The device is show in the assembled configuration in FIG. 30 and in cross section in FIG. 31. In FIG. 32, screw 160 has been rotated (via end 1602) and implant 240 has been moved towards implant 150 and away from curvilinear surface 1306. With movement, space B is now positioned between implant 240 and surface 1306. Comparison of FIGS. 30B and 32B show the movement of marking 2424 relative to the side markings of member 2304.

As previously disclosed, spacer 140 need not have a side member 1404 for attachment onto the side of the vertebral bones. FIG. 33A illustrates spacer 140 without either side members 1404. In this embodiment, the totality of the spacer 140 may be contained within the implanted disc space. FIG. 33B shows the section through the implanted vertebral bones and disc space.

Figure 33:
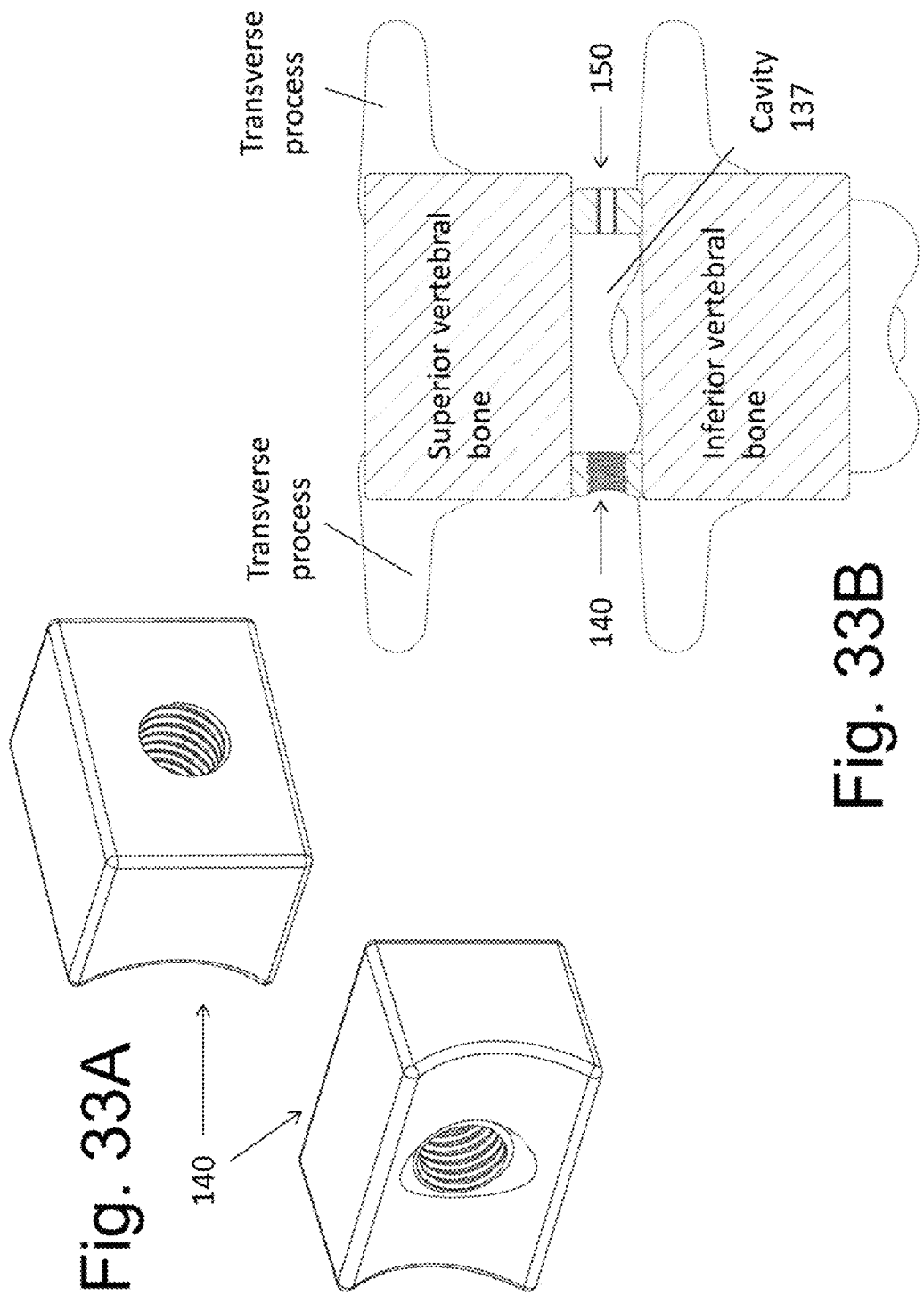
FIGS. 33A, 33B, 34A, and 34B illustrate alternative embodiments of the implantable spacer 140.
Figure 34:
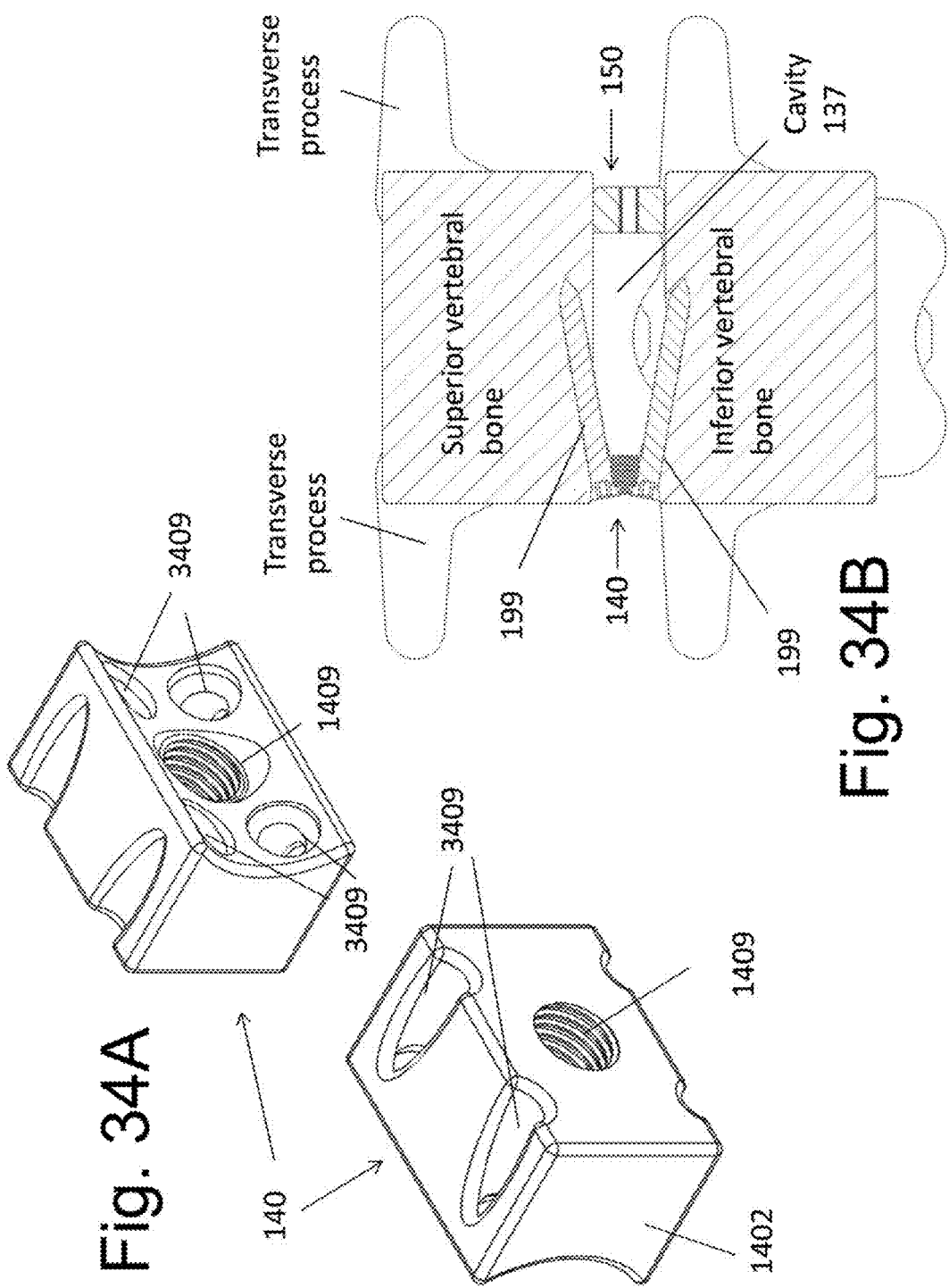

FIG. 34 illustrate a spacer 140 that is similar to that of FIG. 33 but is configured to contain bore holes 1409 within body 1402, wherein said bores are configured to accept bone screws 199 that can anchor the spacer 140 directly into the adjacent vertebral bones. At least two bore holes 1409 are positioned within implant 140 so that at least one bone screw 199 is anchored into each of the vertebral bones above and below the implanted disc space. The screws are not placed into bone in a parallel trajectory, so as to enhance the fixation strength of spacer 140. The implanted spacer 140 may be contained within the disc space and may have no additional member positioned to abut additional side surfaces of the vertebral bones. While not specifically illustrated, each screw may be further locked to spacer 140 after implantation. Many screw to plate locking mechanism are known in the art and any applicable mechanism may be employed. The implanted device is shown in FIG. 34B.

Figure 35:
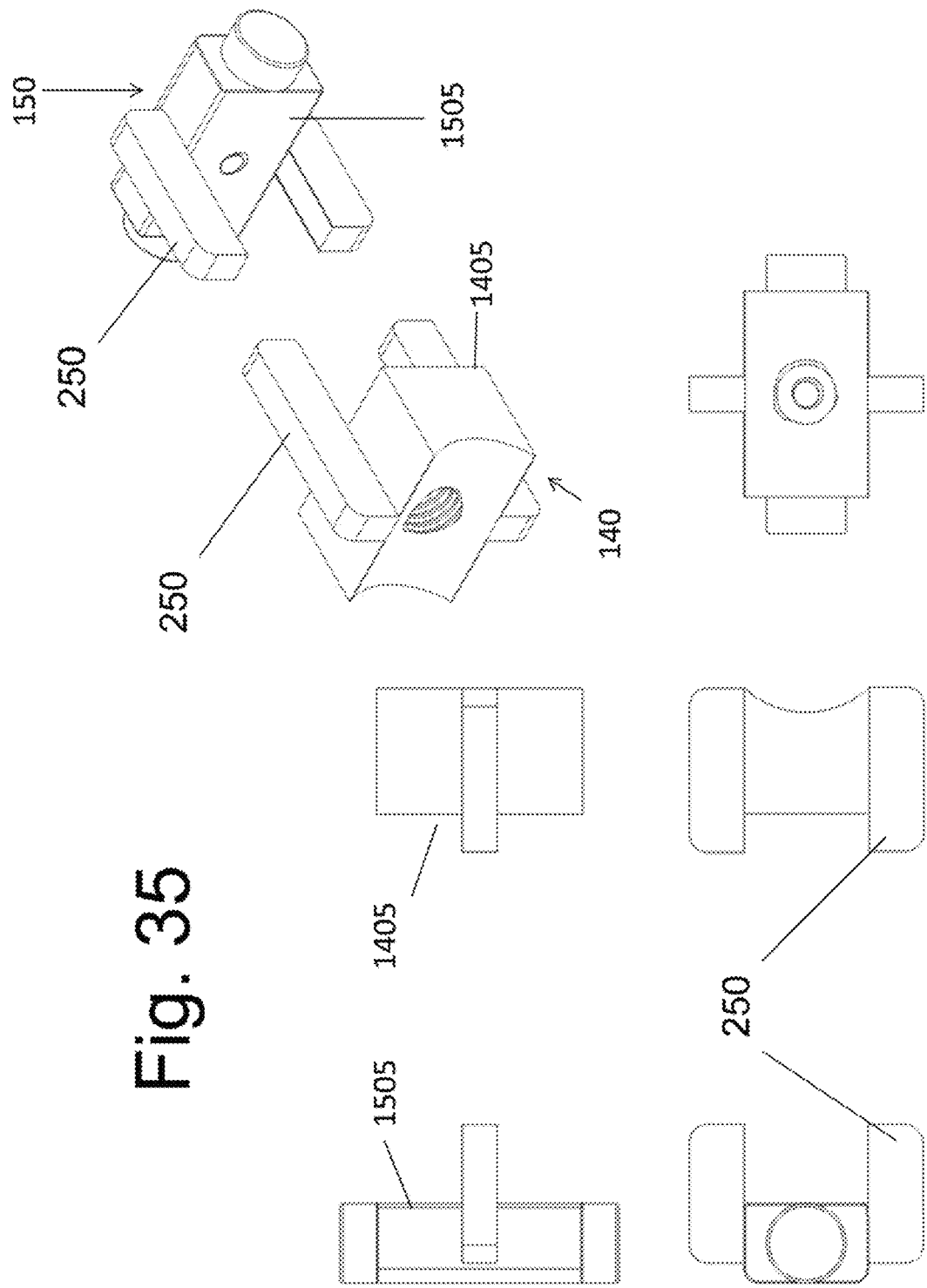
FIGS. 35 and 36 illustrate an additional embodiment of the implantable spacers.
Figure 36:
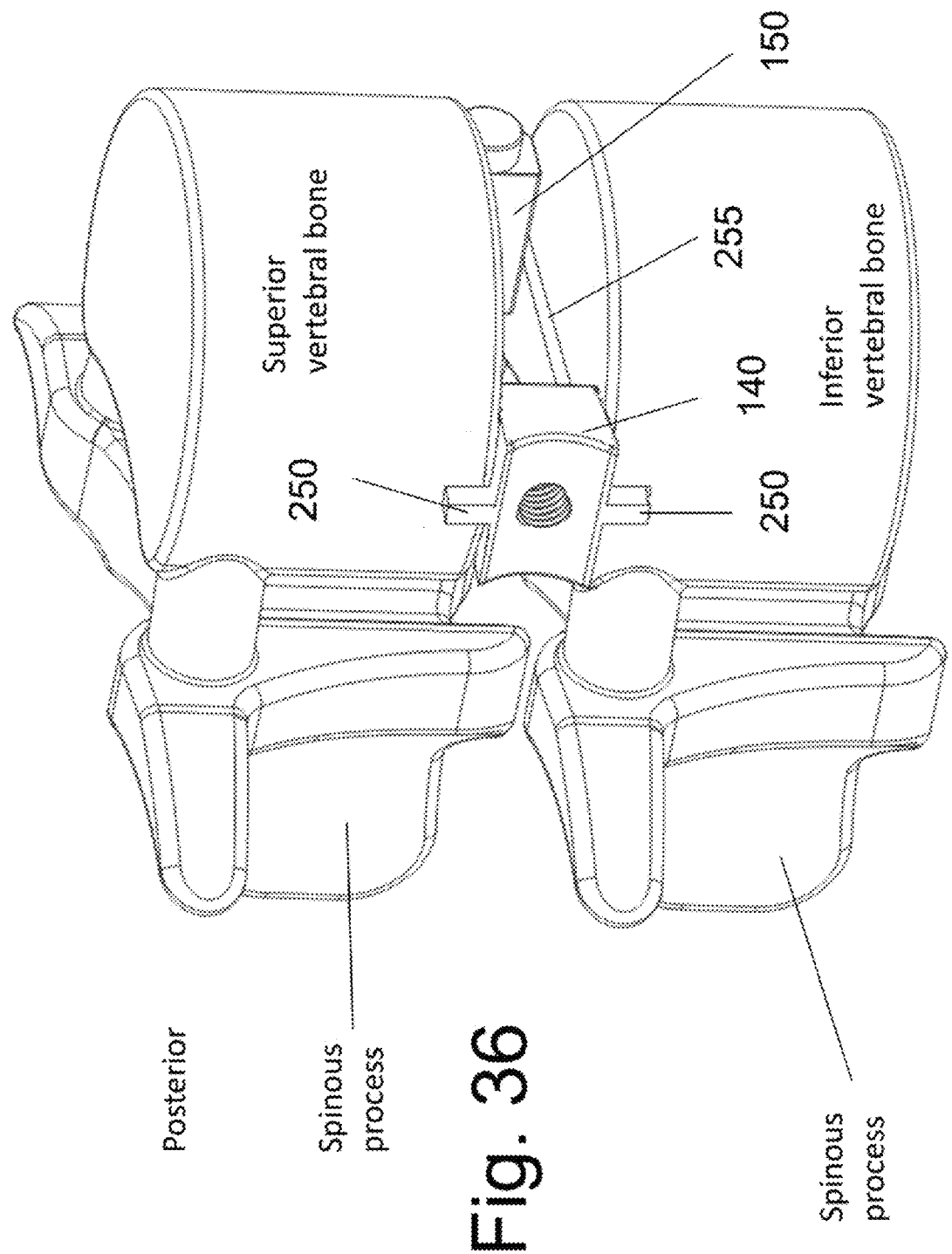

FIG. 35 illustrates an alternative embodiment of the implantable spacer implants. An extension member 250 is attached to the top (and/or bottom or side) surface to at least one of implant 140 and 150. When attached to the top and/or bottom surface of at least one implant, the extension can be positioned into a cut bone channel 255, as shown in FIG. 36. The extension may be wholly contained within the cut channel 255 or some segment of said extension 250 may extend out of the vertebral bone, such as, for example, into the disc space. The extension 250 is less the total width (when measured at its greatest extent) of the upper and/or lower vertebral bone. The width W is shown in FIG. 22B. While extension 250 is shown attached to the upper and lower surface of the implant in FIGS. 35 and 36, it is alternatively attached to a side surface (such as surface 1505 of implant 150, or surface 1405 of implant 140) of said implants and rest at least partially within the disc space on implantation. In this embodiment, extension 250 would at least partially enclose bone graft cavity 137.

An alternative embodiment of member 150 is illustrated as implantable spacer 350. In this embodiment, spacer 350 is of variable length and is comprised of two slidable segments 3502 and 3504. The body of slidable segment 3502 cooperatively interdigitates with the body of slidable segment 3504. The upper and/or lower surfaces 35022 and 35042 may contain surface protrusions or textures (not shown) that increase fixation of these surfaces onto the abutting bone. A threaded bore hole 3508 (threads not shown) is contained within the body of slidable segment 3505, wherein the bore hole receives the threaded end of screw 170.

Figure 38:
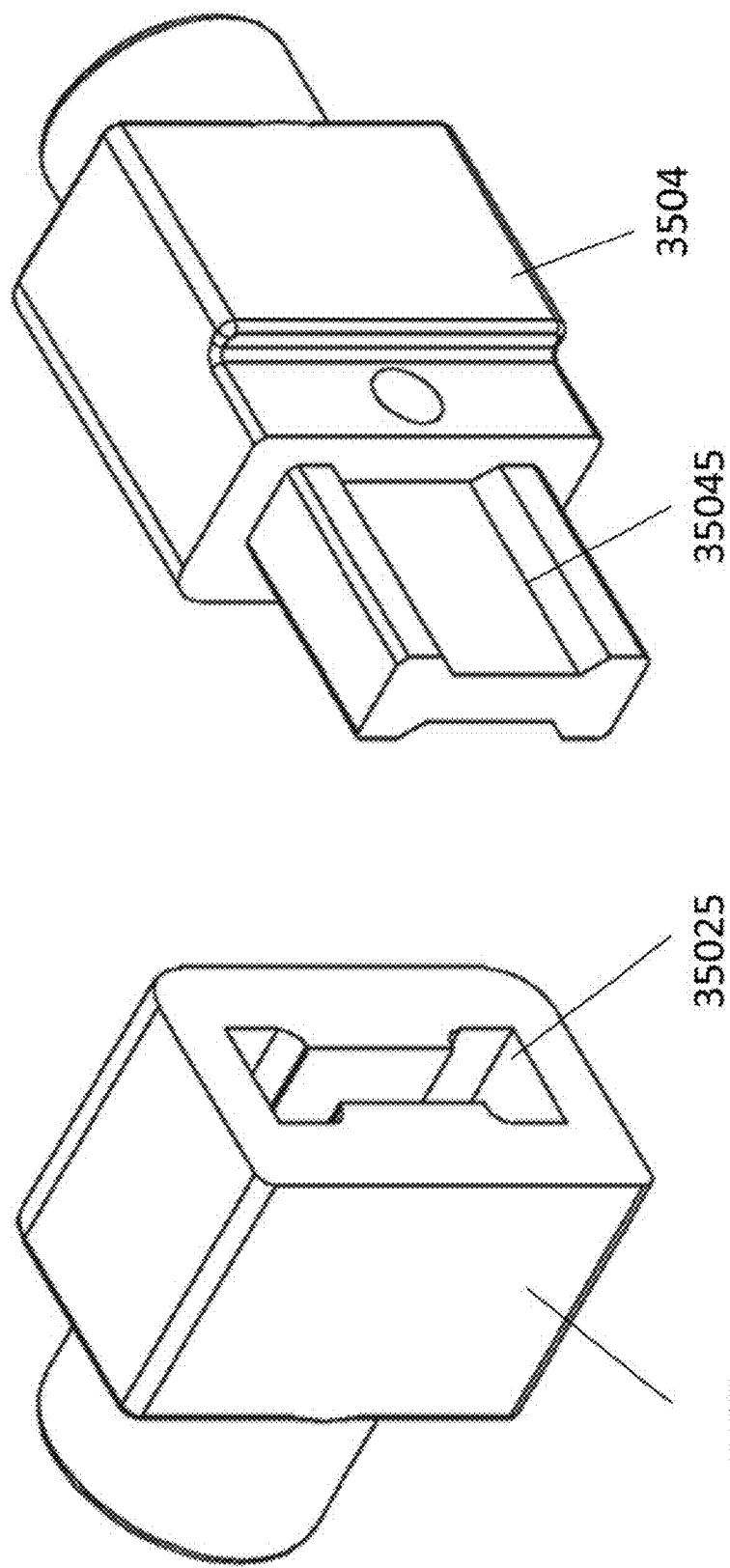
FIG. 38 illustrates a protrusion 35045 of segment 3504 and the complimentary bore 35025 of segment 3502.

FIG. 37A illustrates implantable spacer 350 in a non-expanded configuration whereas FIG. 37B shows spacer 350 after expansion. (Note that length L is greater in the expanded state than in the non-expanded state.) FIG. 38 shows protrusion 35045 of segment 3504 and the complimentary bore 35025 of segment 3502. FIG. 39 illustrate screw 170, wherein the distal end is configured to have threads complimentary to those of bore 3508 (threads not shown). In addition, cam expander 370 is also shown, wherein expander 370 has a bore 3702 adapted to accept screw 70 therein. Note that the distal end alone of each of screw 170 and expander 370 is shown. However, it is contemplated that a placement instrument 130 (not shown in FIG. 39) is configured to couple with spacer 350. Unlike the device of FIGS. 7-10, screw 170 would be positioned inside expander 370, and the latter would be in turn positioned within screw 160.

Figure 40A:
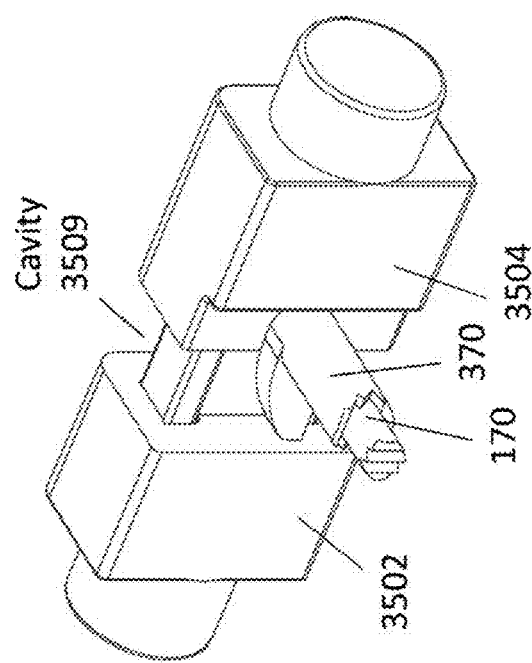
FIG. 40A illustrates exemplary rotation of the expander 370 relative to the spacer 350 to increase the length L of the implant 350.
Figure 40B:
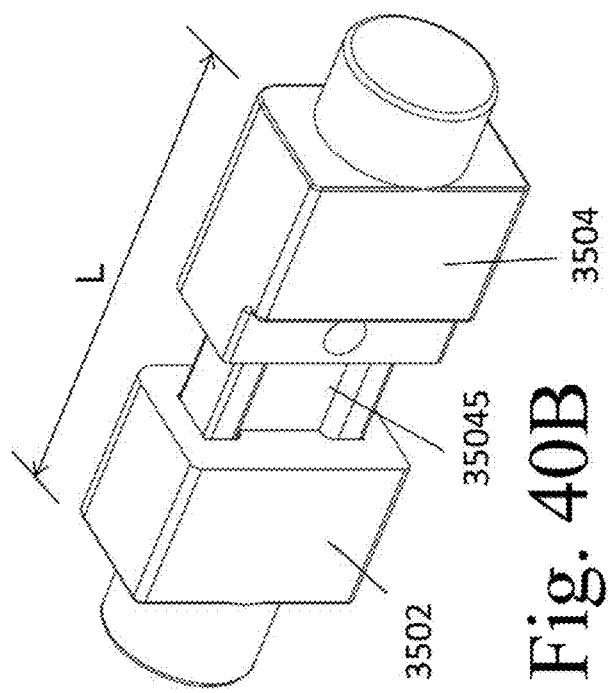
FIG. 40B illustrates the expanded implant 350 after removal of screw 170 and expander 370.

FIG. 40A illustrates that rotation of expander 370 relative to spacer 350 will drive segment 3502 away from segment 3504 and increase the length L of implant 350. FIG. 40B shows the expanded implant 350 after removal of screw 170 and expander 370.

The expanded spacer may be left as shown in FIG. 40B or an additional segment 380 may be attached to spacer 350 within the cavity 3509 created by the separation of segments 3502 and 3504. The addition of segment 380 provides more bone contact/abutment surface than expanded spacer 350 alone, since top and bottom surfaces 3802 of segment 380 will at least partially fill cavity 3509. FIG. 41B illustrates segment 380, whereas FIG. 41A shows one segment 380 coupled to expanded spacer 350 and a second segment 380 positioned to be advanced into cavity 3509. Teeth 3808 are used to lock segment 380 onto extension 35045 on segment 3504.

While each of the segment 380 can be separate members that are added to expanded spacer 350 (as shown), they may alternative be wedge-shaped segments that are implanted as a sub-segment of implant 350, wherein advancement of the wedge-shaped segment between segments 3502 and 3504 is performed after positioning of spacer 350 into the disc space, and wherein the advanced segment 380 both creates a cavity 3509 and fills it in (this embodiment is not shown).

In use, the implantable spacer 350 is configured to be passed though the psoas muscle while in a first configuration and then to expand within the disc space to a second configuration, wherein the length of spacer 350 is greater in the second configuration than in the first configuration. (The length of the device refers to long axis of the spacer, which, in use, is substantially positioned in the direction of a sagittal plane through the implanted disc space and measured in the anterior to posterior direction.)

Figure 42:
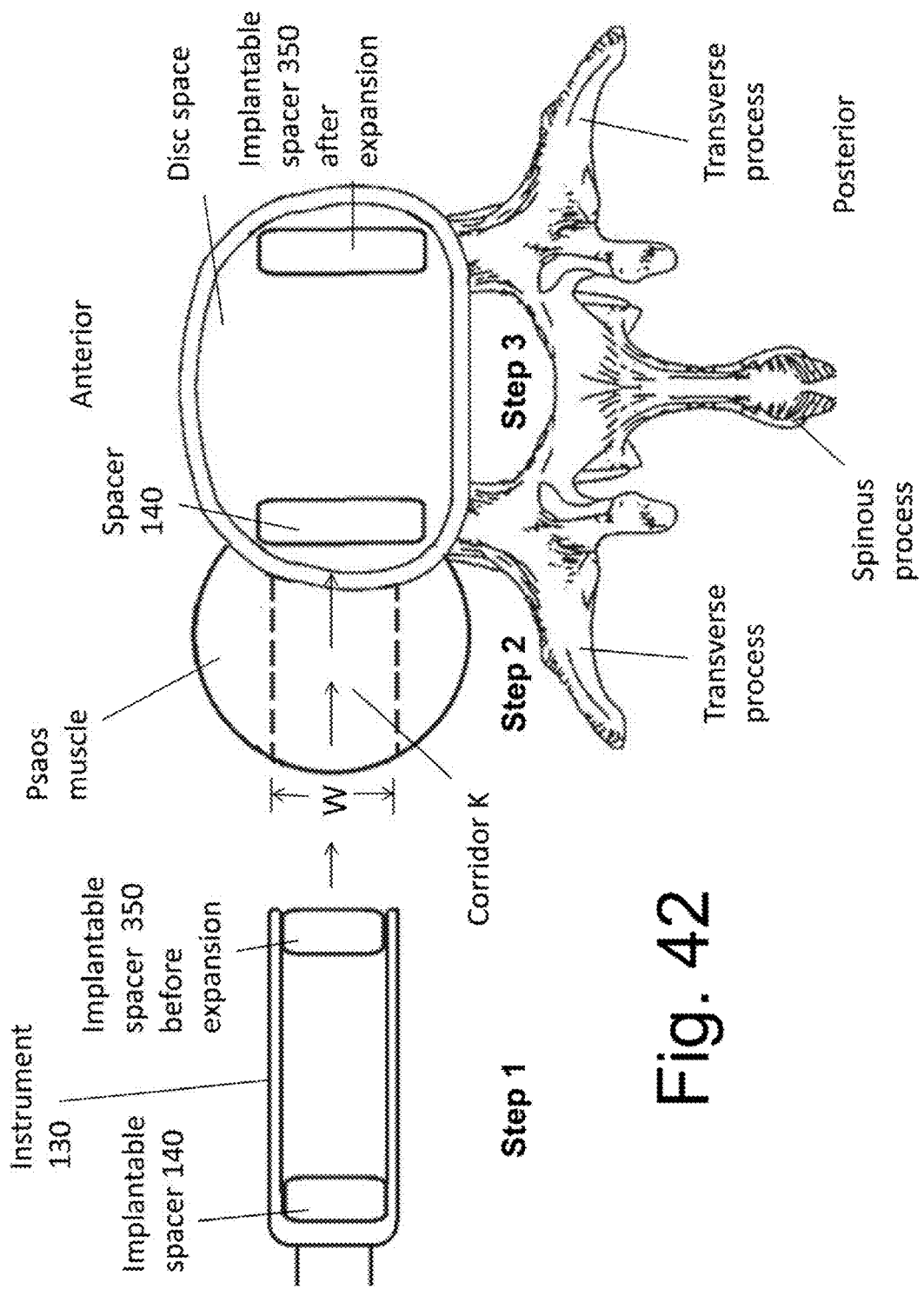
FIG. 42 illustrates an exemplary procedure for using the instrument 130 to attach the implantable spacer 350 prior to expansion.

FIG. 42 schematically illustrates the exemplary procedure, wherein instrument 130 attaches implantable spacer 350 prior to expansion (as shown in FIG. 37A) and then guides said spacer 350 through Corridor K of the psoas muscle. After spacer 350 is positioned within the target disc space, it is transitioned into the second configuration (as shown in FIG. 37B), wherein the second configuration is of greater length than the first spacer configuration. While spacer 350 is shown in both the expanded and non-expanded state in FIG. 42, it is to be understood that three different steps of the procedure are illustrated and not two separate spacers 350. That is, step 1 shows spacers 140 and 350 attached instrument 130 and positioned within the body cavity of the individual but outside of the spine and the psoas muscle. In step 2, spacers 140 and 350 traverse the psoas muscle thought corridor K (instrument not shown while in the muscle). In step 3, spacers 140 and 350 have been positioned at opposing side of implanted disc space (and sitting on the epiphyseal ring) and transitioned into the expanded state—with subsequent complete removal of instrument 130. Note that the length of spacer 350 (as measured in the anterior to posterior plane of the disc space) in the second configuration is greater than the width W of corridor K, through which spacer 350 traversed the psoas muscle while being implanted into the disc space.

Note that spacer 140 is also shows as having been expanded to a greater length after being positioned within the disc space. While not separately illustrated, it is understood that spacer 140 can be made to expand in a manner similar to that illustrated for spacer 350. It is recognized, however, that many other mechanisms can be used to produce implantable spacers of expandable length. In one embodiment, the width of the expandable spacer (as measured in the coronal plane of the spine) may be less or equal to the width of the non-expanded spacer. In another embodiment, the width my greater in the expanded state than in the non-expanded state. That is, the width may change with transition from the first to the second configuration or it may remain constant.

In the herein-described exemplary embodiment of the method of device use, at least two implantable spacers are coupled to an implantation instrument (such as, for example, instrument 130) wherein at least one of the implantable spacers is configured to have an expandable length. The spacer width may be changeable or it may remain constant. The spacers are not directly attached to one another but are at least partially separated by a cavity configured to house bone graft material. The bone graft material is positioned outside at least one of said implantable implants but within a cavity of the implantation instrument. A direct lateral corridor (such as corridor 105; FIG. 4) to the target disc space is used to implant the spacers. (Note that trajectories other than a direct lateral approach may be alternatively used.) In the lumbar spine, the psoas muscle must be traversed in order to position the spacers in the target disc space. After placement of the spacers in the disc space, the at least one expandable spacer is increased in length and the placement instrument is removed from the disc space. In this way, a spacer is positioned on opposing lateral ends of the disc space with the bone graft material positioned there between. At least one of the implanted spacers has a length greater than the trans-psoas corridor used to deliver said spacer to the target disc space in one embodiment. At least one of the implanted spacers does not contain an internal cavity that also contains or is configured to contain bone graft material.

The disclosed devices or any of their components can be made for example of any biologically adaptable or compatible materials. Materials considered acceptable for biological implantation are well known and include, but are not limited to, stainless steel, titanium, tantalum, combination metallic alloys, various plastics, resins, ceramics, biologically absorbable materials and the like. Any components may be also coated/made with nanotube materials to further impart unique mechanical or biological properties. In addition, any components may be also coated/made with osteo-conductive (such as deminerized bone matrix, hydroxyapatite, and the like) and/or osteo-inductive (such as Transforming Growth Factor "TGF-B," Platelet-Derived Growth Factor "PDGF," Bone-Morphogenic Protein "BMP," and the like) bio-active materials that promote bone formation. Further, any surface may be made with a porous ingrowth surface (such as titanium wire mesh, plasma-sprayed titanium, tantalum, porous CoCr, and the like), provided with a bioactive coating, made using tantalum, and/or helical rosette carbon nanotubes (or other carbon nanotube-based coating) in order to promote bone in-growth or establish a mineralized connection between the bone and the implant, and reduce the likelihood of implant loosening. The system or any of its components can also be entirely or partially made of a shape memory material or other deformable material. Lastly, any of the implanted spaces that are disclosed may be partially or completely made out of bone and/or bone graft material.

It will be recognized that while certain aspects of the disclosure are described in terms of a specific sequence of steps of a method, these descriptions are only illustrative of the broader methods thereof, and may be modified as required by the particular application. Certain steps may be rendered unnecessary or optional under certain circumstances. Additionally, certain steps or functionality may be added to the disclosed embodiments, or the order of performance of two or more steps permuted. All such variations are considered to be encompassed within the present disclosure and claimed herein.

While the above detailed description has shown, described, and pointed out novel features of the disclosure as applied to various embodiments, it will be understood that various omissions, substitutions, and changes in the form and details of the device or process illustrated may be made by those skilled in the art without departing from the disclosure. The foregoing description is of the best mode presently contemplated. This description is in no way meant to be limiting, but rather should be taken as illustrative of the general principles. The scope of the present disclosure should be determined with reference to the claims.

What is claimed is:

1. An orthopedic device assembly configured for delivery of a first implantable device and a second implantable device to an intervertebral disc space, said intervertebral disc space disposed between a superior vertebral bone and an inferior vertebral bone, the orthopedic device assembly comprising:
    said first implantable device comprising: (i) a first surface configured to abut said superior intervertebral bone, and (ii) a second surface configured to abut said inferior vertebral bone;
    said second implantable device being a separate component from the first implantable device and comprising at least one member having a first aperture configured to receive a fastener, said fastener configured to be advanced at least partially through said first aperture and into one of said superior vertebral bone or said inferior vertebral bone; and
    a non-implantable placement instrument comprising an intermediate segment, a proximal segment and a distal segment, said placement instrument extended along a longitudinal axis from a proximal end of said proximal segment to said distal segment;
    wherein:
        said proximal segment comprises a handle;
        said distal segment comprises a first surface configured to engage with said first implantable device; and
        said intermediate segment comprises a second surface configured to engage with said second implantable device; and
    wherein said non-implantable placement instrument is configured such that, as measured along said longitudinal axis, a distance between said first surface and said proximal end is greater than a distance between said second surface and said proximal end.

2. The orthopedic device assembly of claim 1, wherein said first implantable device further comprises a cavity configured to house a bone forming material.

3. The orthopedic device assembly of claim 1, wherein said intermediate segment comprises at least a pair of extension elements configured to straddle at least a portion of said second implantable device, said second surface of said intermediate segment comprising a surface of at least one of said pair of extension elements that is configured to engage said second implantable device.

4. The orthopedic device assembly of claim 3, wherein:
    said distal segment comprises a distal end of each of said pair of extension elements; and
    said first surface of said distal segment comprises a first pair of engagement features, each of said first pair of engagement features being (i) disposed on one of said pair of extension elements and (ii) configured to engage with said first implantable device.

5. The orthopedic device assembly of claim 4, wherein said first implantable device further comprises a pair of outer side surfaces and a second pair of engagement features having a complementary configuration to said first pair of engagement features.

6. The orthopedic device assembly of claim 1, further comprising a second aperture formed within said second implantable device; and
    wherein said placement instrument further comprises a retention apparatus, said retention apparatus comprising at least one elongate member configured to enable coupling of a distal end of said retention apparatus to said first implantable device, said distal end of said retention apparatus configured to extend through said second aperture of said second implantable device to couple to said first implantable device.

7. The orthopedic device assembly of claim 1, further comprising a second aperture centrally formed within said second implantable device; and
    wherein said second aperture is configured to receive a locking feature, said locking feature configured to limit backing out of said fastener after said fastener is received within said first aperture.

8. An orthopedic device assembly configured for delivery of a first implantable device and a second implantable device to an intervertebral disc space, said intervertebral disc space disposed at least partly between a superior vertebral bone and an inferior vertebral bone, the orthopedic device assembly comprising:
    said first implantable device comprising: (i) a first surface configured to abut said superior intervertebral bone, and (ii) a second surface configured to abut said inferior vertebral bone;
    said second implantable device being non-integrally formed with said first implantable device and comprising: (i) a first aperture, and (ii) at least one side member disposed adjacent to said first aperture, said at least one side member having a second aperture configured to receive a fastener that is sized to be at least partially advanced through said second aperture and into one of said superior vertebral bone or said inferior vertebral bone; and a non-implantable placement instrument configured to position said first implantable device and said second implantable device, said placement instrument extending along a longitudinal axis from a proximal end to a distal segment and comprising:
  a proximal segment comprising a handle;
  said distal segment configured to engage said first implantable device;
  an intermediate segment positioned at least partially between said proximal segment and said distal segment, said intermediate segment comprising a second surface configured to engage said second implantable device; and
  a retention apparatus comprising at least one elongated member capable of alignment with said longitudinal axis of said placement instrument, a distal end of said retention apparatus configured to extend through said first aperture of said second implantable device and couple to said first implantable device.

9. The orthopedic device assembly of claim 8, wherein said distal end of said retention apparatus is configured to threadedly couple with said first implantable device.

10. The orthopedic device assembly of claim 8, wherein said non-implantable placement instrument is configured such that a distance between said first surface and said proximal end is greater than a distance between said second surface and said proximal end, as measured along said longitudinal axis.

11. The orthopedic device assembly of claim 8, wherein the at least one elongated member of the retention apparatus is sized to be at least partially seated within an internal channel of said handle.

12. The orthopedic device assembly of claim 8, wherein said intermediate segment comprises at least a pair of extension elements configured to straddle at least a portion of said second implantable device.

13. The orthopedic device assembly of claim 8, wherein said first aperture of said second implantable device is configured to receive a locking feature; and
  said locking feature is configured to limit back-out of said fastener from a seated position within said second aperture of said second implantable device.

14. The orthopedic device assembly of claim 8, wherein said first implantable device further comprises a cavity configured to seat a bone forming material.

15. An orthopedic device assembly configured for delivery of implants to an intervertebral disc space, said intervertebral disc space disposed between a superior vertebral bone and an inferior vertebral bone, the orthopedic device assembly comprising:
  a first implantable device comprising (i) a first surface configured to abut said superior intervertebral bone and (ii) a second surface configured to abut said inferior vertebral bone;
  a second implantable device separately formed from the first implantable segment and comprising (i) a pair of outer side surfaces and (ii) at least one segment having a first aperture configured to receive a fastener, said fastener configured to be advanced at least partially through said first aperture and into one of said superior vertebral bone or said inferior vertebral bone; and a non-implantable placement instrument configured to position said first implantable device and said second implantable device, said placement instrument comprising:
  a proximal segment comprising a handle;
  a distal segment comprising a first surface, said first surface configured to engage with said first implantable device;
  an intermediate segment comprising at least a pair of extension elements configured to straddle at least a portion of said second implantable device, at least one of said pair of side extension elements comprising a second surface configured to engage with one of said pair of outer side surfaces of said second member;
  wherein said non-implantable placement instrument is extended from a proximal end of said proximal segment to said distal segment along a longitudinal axis; and
  wherein, said non-implantable placement instrument is configured such that said first surface of the distal segment is a greater distance from said proximal end, as measured along said longitudinal axis, than said second surface of the intermediate segment.

16. The orthopedic device assembly of claim 15, wherein said first implantable device further comprises a cavity configured to house a bone forming material.

17. The orthopedic device assembly of claim 15, wherein said first implantable device is sized so as to be at least partially inserted within said intervertebral disc space.

18. The orthopedic device assembly of claim 15, wherein:
  said second implantable device further comprises a second aperture; and
  said placement instrument further comprises a retention apparatus, said retention apparatus comprising a distal portion configured to (i) extend through said second aperture and (ii) couple with said first implantable device.

19. The orthopedic device assembly of claim 18, wherein said first surface of said distal segment of the non-implantable placement instrument is at least partially comprised of an end segment of said distal portion of the retention member.

20. The orthopedic device assembly of claim 19, wherein said end segment of said distal portion of said retention member is configured to threadedly engage with said first implantable device.

21. The orthopedic device assembly of claim 18, wherein said distal portion of the retention member is configured to be positioned collinear with said longitudinal axis of said non-implantable placement instrument.

22. The orthopedic device assembly of claim 18, wherein said second aperture is configured to receive a locking feature; and
  said locking feature is configured to restrict unintended retraction of said fastener from the first aperture when the fastener is seated therein.

23. The orthopedic device assembly of claim 15, wherein:
  (i) said distal segment of the non-implantable placement instrument comprises a distal end of at least one of said pair of extension elements; and
  (ii) said first surface of said distal segment comprises an engagement feature that is disposed on said distal end of the at least one of said pair of extension elements and is configured to engage with said first member.

24. The orthopedic device assembly of claim 15, wherein said second implantable device further comprises a spacer segment that is sized to be inserted within said intervertebral disc space.

25. An orthopedic device assembly, comprising:
a first implantable device sized to be positioned at least partly within an intervertebral disc space that is disposed between a superior vertebral bone and an inferior vertebral bone, the first implantable device comprising:
  (i) a superior surface configured to abut said superior intervertebral bone, and
  (ii) an inferior surface configured to abut said inferior vertebral bone;
a second implantable device, separately formed from the first implantable device and configured to be positioned at least partly on an outer surface of one or more of said superior vertebral bone and said inferior vertebral bone, said second implantable device comprising:
  (i) a first aperture configured to seat a first fastener, a shank portion of said first fastener configured to be at least partially advanced through said first aperture and into said superior vertebral bone when said first fastener is an a first seated position;
  (ii) a second aperture configured to seat a second fastener, a shank portion of said second fastener configured to be at least partially advanced through said second aperture and into said inferior vertebral bone when said second fastener is a second seated position;
  (iii) a third aperture disposed between said first aperture and said second aperture, said third aperture configured to seat a locking feature that is adapted to limit undesired back out of at least one of said first and second fasteners from a respective seated position within said first and second apertures; and
a non-implantable placement instrument configured to position said first implantable device and said second implantable device at said intervertebral disc space, said placement instrument comprising:
a proximal segment comprising a handle;
a distal segment comprising a first surface, said first surface configured to engage with said first implantable device; and
an intermediate segment between said proximal segment and said distal segment, said intermediate segment comprising a second surface configured to engage with said second implantable device;
wherein said non-implantable placement instrument extends from said proximal segment to said distal segment along a longitudinal axis; and
wherein, said non-implantable placement instrument and said first and second implantable devices are configured such that, when engaged, said first implantable device and said second implantable are consecutively arranged along said longitudinal axis.

26. The orthopedic device assembly of claim 25, wherein said intermediate segment of said non-implantable placement instrument comprises at least a pair of extensions configured to straddle said second implantable device, said second surface of said intermediate segment comprising an inner surface of each of said pair of extensions.

27. The orthopedic device assembly of claim 26, wherein:
said distal segment of the non-implantable placement instrument comprises a distal end of at least one of said pair of extension elements; and
said first surface of said distal segment comprises an engagement feature that is disposed on said distal end of said at least one of said pair of extension elements, said engagement feature configured to engage with said first member.

28. The orthopedic device assembly of claim 25, wherein said non-implantable placement instrument further comprises a retention apparatus, the retention apparatus comprising a distal end that is (i) sized to extend through said third aperture of the second implantable device and (ii) configured to couple to said first implantable device.

29. The orthopedic device assembly of claim 28, wherein said first surface of said distal segment of said non-implantable placement instrument is at least partially comprised of said distal end of said retention member.

30. The orthopedic device assembly of claim 25, wherein said second implantable device further comprises a spacer segment that is sized to be inserted within said intervertebral disc space.

* * * * *

UNITED STATES PATENT AND TRADEMARK OFFICE
CERTIFICATE OF CORRECTION

PATENT NO. : 9,901,458 B1
APPLICATION NO. : 15/599315
DATED : February 27, 2018
INVENTOR(S) : Samy Abdou Page 1 of 2

It is certified that error appears in the above-identified patent and that said Letters Patent is hereby corrected as shown below:

In the Claims (Column 18, Lines 9 – 15 – Claim 15):
Currently Reads:
"an intermediate segment comprising at least a pair of extension elements configured to straddle at least a portion of said second implantable device, at least one of said pair of side extension elements comprising a second surface configured to engage with one of said pair of outer side surfaces of said second member;"

Should Read:
-- an intermediate segment comprising at least a pair of extension elements configured to straddle at least a portion of said second implantable device, at least one of said pair of side extension elements comprising a second surface configured to engage with one of said pair of outer side surfaces of said second implantable device; --

(Column 19, Lines 19 – 29 – Claim 25):
Currently Reads:
"(i) a first aperture configured to seat a first fastener, a shank portion of said first fastener configured to be at least partially advanced through said first aperture and into said superior vertebral bone when said first fastener is an a first seated position;
(ii) a second aperture configured to seat a second fastener, a shank portion of said second fastener configured to be at least partially advanced through said second aperture and into said inferior vertebral bone when said second fastener is a second seated position;"

Should Read:
-- (i) a first aperture configured to seat a first fastener, a shank portion of said first fastener configured to be at least partially advanced through said first aperture and into said superior vertebral bone when said first fastener is in a first seated position;

Signed and Sealed this
Thirty-first Day of October, 2023

Katherine Kelly Vidal
*Director of the United States Patent and Trademark Office*

(ii) a second aperture configured to seat a second fastener, a shank portion of said second fastener configured to be at least partially advanced through said second aperture and into said inferior vertebral bone when said second fastener is in a second seated position; --

(Column 20, Lines 8 – 12 – Claim 25):
Currently Reads:
"wherein, said non-implantable placement instrument and said first and second implantable devices are configured such that, when engaged, said first implantable device and said second implantable are consecutively arranged along said longitudinal axis."

Should Read:
-- wherein, said non-implantable placement instrument and said first and second implantable devices are configured such that, when engaged, said first implantable device and said second implantable device are consecutively arranged along said longitudinal axis. --